United States Patent
Han et al.

(10) Patent No.: US 12,421,215 B2
(45) Date of Patent: *Sep. 23, 2025

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Mi Yeon Han, Daejeon (KR); Dong Hoon Lee, Daejeon (KR); Jung Oh Huh, Daejeon (KR); Boon Jae Jang, Daejeon (KR); Dong Uk Heo, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 403 days.

This patent is subject to a terminal disclaimer.

(21) Appl. No.: 16/480,651

(22) PCT Filed: Apr. 3, 2018

(86) PCT No.: PCT/KR2018/003927
§ 371 (c)(1),
(2) Date: Jul. 24, 2019

(87) PCT Pub. No.: WO2018/225940
PCT Pub. Date: Dec. 13, 2018

(65) Prior Publication Data
US 2019/0363260 A1    Nov. 28, 2019

(30) Foreign Application Priority Data

Jun. 7, 2017    (KR) .......................... 10-2017-0070988
Nov. 28, 2017   (KR) .......................... 10-2017-0160633

(51) Int. Cl.
*C07D 405/04*    (2006.01)
*C07D 405/10*    (2006.01)
(Continued)

(52) U.S. Cl.
CPC ......... *C07D 405/04* (2013.01); *C07D 405/10* (2013.01); *C07D 409/04* (2013.01);
(Continued)

(58) Field of Classification Search
CPC ............. H01L 51/0067; H01L 51/0052; H01L 51/0054; H01L 51/0056; H01L 51/0058;
(Continued)

(56) References Cited

U.S. PATENT DOCUMENTS

2004/0251816 A1    12/2004    Leo et al.
2006/0273714 A1*   12/2006    Forrest .................. H10K 50/11
                                                      313/506
(Continued)

FOREIGN PATENT DOCUMENTS

CN    101331626 A      12/2008
CN    102911145 A  *    2/2013
(Continued)

OTHER PUBLICATIONS

English translation of WO 2007069569 A1 (Year: 2007).*
(Continued)

*Primary Examiner* — Jennifer A Boyd
*Assistant Examiner* — Braelyn R Watson
(74) *Attorney, Agent, or Firm* — Bryan Cave Leighton Paisner LLP

(57) ABSTRACT

Provided is a heterocyclic compound of Chemical Formula 1:

(Continued)

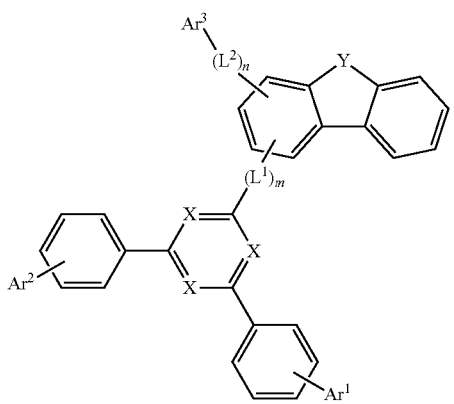

and an organic electroluminescent device including the same.

6 Claims, 1 Drawing Sheet

(51) Int. Cl.
$C07D\ 409/04$ (2006.01)
$C07D\ 409/10$ (2006.01)
$C09K\ 11/06$ (2006.01)
$H10K\ 50/11$ (2023.01)
$H10K\ 50/15$ (2023.01)
$H10K\ 50/16$ (2023.01)
$H10K\ 50/17$ (2023.01)
$H10K\ 85/60$ (2023.01)
$H10K\ 101/10$ (2023.01)

(52) U.S. Cl.
CPC ............ $C07D\ 409/10$ (2013.01); $C09K\ 11/06$ (2013.01); $H10K\ 85/615$ (2023.02); $H10K\ 85/622$ (2023.02); $H10K\ 85/624$ (2023.02); $H10K\ 85/626$ (2023.02); $H10K\ 85/654$ (2023.02); $H10K\ 85/6574$ (2023.02); $H10K\ 85/6576$ (2023.02); $C09K\ 2211/1018$ (2013.01); $H10K\ 50/11$ (2023.02); $H10K\ 50/15$ (2023.02); $H10K\ 50/16$ (2023.02); $H10K\ 50/17$ (2023.02); $H10K\ 50/171$ (2023.02); $H10K\ 2101/10$ (2023.02)

(58) Field of Classification Search
CPC ............ H01L 51/0073; H01L 51/0074; H01L 51/5012; H01L 51/5016; H01L 51/5056; H01L 51/5072; H01L 51/5088; H01L 51/5092; H01L 51/5076; H01L 51/5096; H01L 51/0055; C07D 405/04; C07D 409/04; C07D 409/02–06; C07D 409/10–12; C07D 405/02–06; C07D 405/10–12; C09K 11/06; C09K 2211/1018; H10K 85/654; H10K 85/615; H10K 85/622; H10K 85/624; H10K 85/626; H10K 85/6574; H10K 85/6576; H10K 50/11; H10K 50/15; H10K 50/16; H10K 50/17; H10K 50/171; H10K 2101/10; H10K 50/165; H10K 85/30; H10K 85/623

See application file for complete search history.

(56) References Cited

U.S. PATENT DOCUMENTS

| | | | |
|---|---|---|---|
| 2010/0038634 A1* | 2/2010 | Nagao | C09B 57/001 257/40 |
| 2011/0297923 A1* | 12/2011 | Mizuki | C09K 11/025 556/415 |
| 2012/0104369 A1* | 5/2012 | Kawata | H01L 51/0074 257/E51.024 |
| 2013/0270524 A1 | 10/2013 | Park et al. | |
| 2013/0328021 A1 | 12/2013 | Lim et al. | |
| 2014/0014925 A1 | 1/2014 | Jung et al. | |
| 2014/0014927 A1* | 1/2014 | Kim | H10K 85/626 257/40 |
| 2014/0034931 A1 | 2/2014 | Inoue et al. | |
| 2014/0073784 A1* | 3/2014 | Mizutani | H01L 51/0054 544/216 |
| 2014/0231769 A1* | 8/2014 | Nishimura | H01L 51/0056 257/40 |
| 2014/0367654 A1* | 12/2014 | Kim | H01L 51/0052 257/40 |
| 2015/0069342 A1 | 3/2015 | Lee et al. | |
| 2015/0069347 A1 | 3/2015 | Kim et al. | |
| 2015/0069355 A1 | 3/2015 | Hwang et al. | |
| 2015/0249221 A1 | 9/2015 | Zeng et al. | |
| 2015/0336937 A1 | 11/2015 | Lee et al. | |
| 2015/0357586 A1* | 12/2015 | Horiuchi | H10K 50/81 257/40 |
| 2016/0028021 A1* | 1/2016 | Zeng | C07D 421/10 257/40 |
| 2016/0093808 A1 | 3/2016 | Adamovich et al. | |
| 2016/0111657 A1 | 4/2016 | Lee et al. | |
| 2016/0197285 A1* | 7/2016 | Zeng | C07D 409/10 257/40 |
| 2016/0204356 A1 | 7/2016 | Yang et al. | |
| 2016/0268516 A1* | 9/2016 | Tanaka | H10K 85/653 |
| 2017/0025618 A1 | 1/2017 | Zheng et al. | |
| 2017/0054087 A1 | 2/2017 | Zeng et al. | |
| 2017/0186965 A1* | 6/2017 | Parham | H01L 51/0074 |
| 2017/0213983 A1 | 7/2017 | Hayama et al. | |
| 2018/0037546 A1 | 2/2018 | Sugino et al. | |
| 2018/0053900 A1* | 2/2018 | Eum | H10K 85/6572 |
| 2018/0093962 A1* | 4/2018 | Choi | C07D 409/12 |
| 2018/0123055 A1* | 5/2018 | Park | C07D 409/14 |
| 2019/0106391 A1* | 4/2019 | Wucherer-Plietker | H01L 51/0058 |
| 2019/0140187 A1* | 5/2019 | Schulze | H10K 85/6574 |
| 2020/0039971 A1* | 2/2020 | Kang | C07D 405/14 |
| 2021/0257554 A1 | 8/2021 | Zeng et al. | |

FOREIGN PATENT DOCUMENTS

| | | | | |
|---|---|---|---|---|
| CN | 105315265 A | | 2/2016 | |
| CN | 106459018 A | | 2/2017 | |
| CN | 106565705 | | 4/2017 | |
| CN | 106565705 A | * | 4/2017 | |
| CN | 110520419 | | 11/2019 | |
| EP | 1962354 A1 | * | 8/2008 | ........... C07D 307/91 |
| EP | 2966706 A2 | | 1/2016 | |
| EP | 2991128 A1 | | 3/2016 | |
| JP | 5831654 | | 12/2015 | |
| JP | 2016-185914 | | 10/2016 | |
| KR | 10-2000-0051826 | | 8/2000 | |
| KR | 2011105228 A | * | 9/2011 | ......... H01L 51/0052 |
| KR | 2013010633 A | * | 1/2013 | ............ C07C 15/14 |
| KR | 10-2014-0013351 | | 2/2014 | |
| KR | 10-2014-0014956 | | 2/2014 | |
| KR | 10-2014-0014959 | | 2/2014 | |
| KR | 10-2014-0017233 | | 2/2014 | |
| KR | 10-2014-0099082 | | 8/2014 | |
| KR | 10-2016-0028524 | | 3/2016 | |
| KR | 10-2016-0046077 | | 4/2016 | |
| KR | 10-2016-0046078 | | 4/2016 | |
| KR | 10-2016-0080090 | | 7/2016 | |
| KR | 20160080090 A | * | 7/2016 | ............ C09K 11/06 |
| KR | 10-2016-0107975 | | 9/2016 | |
| KR | 10-2016-0126873 | | 11/2016 | |

(56) References Cited

FOREIGN PATENT DOCUMENTS

| KR | 10-2017-0057660 | | 5/2017 | | |
|----|-----------------|---|--------|---|---|
| KR | 10-2017-0058619 | | 5/2017 | | |
| KR | 10-2017-0086211 | | 7/2017 | | |
| WO | 2003-012890 | | 2/2003 | | |
| WO | WO-2007069569 | A1 * | 6/2007 | ........... | C07D 405/10 |
| WO | 2011-126224 | | 10/2011 | | |
| WO | 2013-027846 | | 2/2013 | | |
| WO | 2016-108596 | | 7/2016 | | |
| WO | WO-2016108596 | A2 * | 7/2016 | ........... | C07D 405/04 |
| WO | 2016-129672 | | 8/2016 | | |
| WO | 2016-084962 | | 9/2017 | | |

OTHER PUBLICATIONS

English translation of WO 2016108596 A2 obtained from Global Dossier (Year: 2016).*
English translation of CN 106565705 A obtained from Global Dossier (Year: 2017).*
English translation of KR 20130010633 A provided by Google Patents (Year: 2013).*
English translation of CN 102911145 obtained by Global Dossier (Year: 2013).*
English translation of KR 20110105228 A obtained from Global Dossier (Year: 2011).*
International Search Report and the Written Opinion of PCT/KR2018/003927, mailed Jul. 13, 2018.
Office Action of Chinese Patent Office in Appl'n No. 201880008609.X, dated Mar. 23, 2022.

* cited by examiner

[FIG. 1]
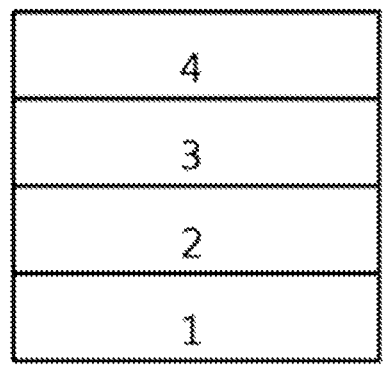
[FIG. 2]
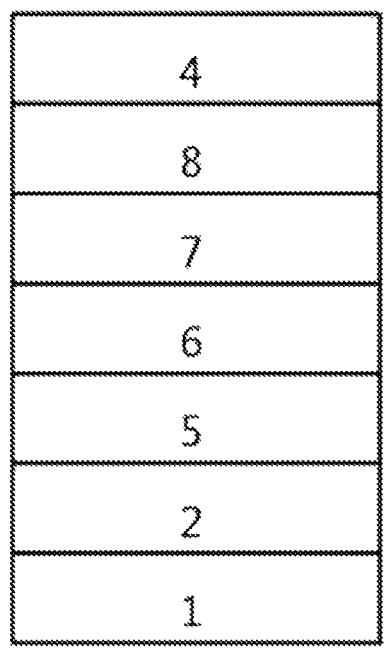

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2018/003927 filed on Apr. 3, 2018, which claims the benefits of the filing dates of Korean Patent Application No. 10-2017-0070988 filed with Korean Intellectual Property Office on Jun. 7, 2017, and Korean Patent Application No. 10-2017-0160633 filed with Korean Intellectual Property Office on Nov. 28, 2017, the entire contents of which are incorporated herein by reference.

TECHNICAL FIELD

The present disclosure relates to a novel heterocyclic compound and to an organic electroluminescent device including the same.

BACKGROUND

In general, an organic light emitting phenomenon refers to one in which electrical energy is converted into light energy by using an organic material. The organic electroluminescent device using the organic light emitting phenomenon has beneficial characteristics such as a wide viewing angle, excellent contrast, a fast response time, and excellent luminance, driving voltage, and response speed, and thus many studies have proceeded thereon.

The organic electroluminescent device generally has a structure which includes an anode, a cathode, and an organic material layer interposed between the anode and the cathode. The organic material layer frequently has a multilayered structure that includes different materials in order to enhance efficiency and stability of the organic electroluminescent device, and for example, the organic material layer can be formed of a hole injection layer, a hole transport layer, a light emitting layer, an electron transport layer, an electron injection layer, and the like.

In the structure of the organic electroluminescent device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state.

There is a continuing need for the development of new materials for the organic materials used in such organic electroluminescent devices.

PRIOR ART DOCUMENTS

Patent Document (Patent Document 0001) Korean Patent Laid-open Publication No. 10-2000-0051826 (Aug. 16, 2000)

DETAILED DESCRIPTION OF THE INVENTION

Technical Problem

It is an object of the present disclosure to provide a novel heterocyclic compound as an organic electroluminescent compound.

It is another object of the present disclosure to provide an organic electroluminescent device including the above-mentioned heterocyclic compound.

Technical Solution

According to one aspect of the present disclosure, a compound of Chemical Formula 1 is provided:

[Chemical Formula 1]

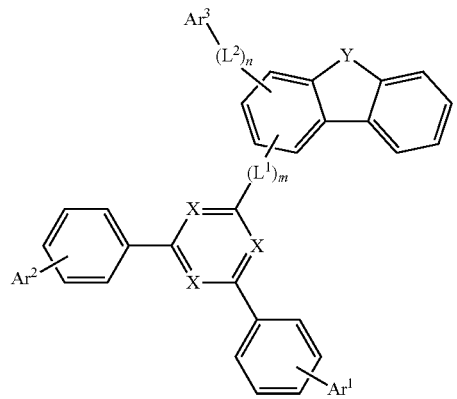

wherein, in Chemical Formula 1:
  each X is independently N or $CR^0$, in which at least two of X are N;
  $R^0$ is hydrogen, deuterium, a $C_{6-50}$ aryl group which is substituted or unsubstituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group, or a $C_{2-50}$ heteroaryl group which contains at least one heteroatom selected from the group consisting of N, O, and S, and which is substituted or unsubstituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group;
  Y is O or S;
  $L^1$ and $L^2$ are each independently a direct bond, or a $C_{6-20}$ arylene group which is unsubstituted or substituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group;
  m and n are each independently an integer of 0 to 2;
  $Ar^1$ and $Ar^2$ are each independently hydrogen, deuterium, a $C_{6-50}$ aryl group which is substituted or unsubstituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group, or a $C_{2-50}$ heteroaryl group which contains at least one heteroatom selected from the group consisting of N, O, and S, and which is substituted or unsubstituted by a $C_{6-30}$ aryloxy group; and
  $Ar^3$ is a $C_{6-60}$ aryl group.

According to another aspect of the present disclosure, an organic electroluminescent device is provided, including: a first electrode; a second electrode provided opposite to the first electrode; and one or more organic material layers provided between the first electrode and the second electrode, wherein at least one layer of the organic material layers includes the compound of Chemical Formula 1.

Advantageous Effects

The compound of Chemical Formula 1 can be used as a material of an organic material layer of an organic electroluminescent device, and can improve the efficiency, achieve a low driving voltage, and/or improve lifetime characteristics in the organic electroluminescent device. In particular, the compound of Chemical Formula 1 can be used as a material for hole injection, hole transport, hole injection and transport, light emitting, electron transport, or electron injection.

BRIEF DESCRIPTION OF THE DRAWINGS

FIG. 1 shows an example of an organic electroluminescent device including a substrate 1, an anode 2, a light emitting layer 3, and a cathode 4.

FIG. 2 shows an example of an organic electroluminescent device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

Unless otherwise specified throughout this specification, the technical terms used herein are only for describing specific embodiments, and are not intended to limit the present disclosure.

Further, the singular forms "a," "an," and "the" are intended to include plural forms, unless the context clearly indicates otherwise.

The term "including" or "comprising" used herein specifies a specific feature, region, integer, step, action, element, and/or component, but does not exclude the presence or addition of a different specific feature, area, integer, step, action, element, component, and/or group.

In the present disclosure, the notation "*" in a chemical formula indicates a portion in which a corresponding group is connected to another group.

In the present disclosure, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O, and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present disclosure, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to still another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group can be a straight chain or a branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples of the alkenyl group include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, the alkynyl group is a monovalent group in which one atom of hydrogen is removed from an alkyne having 2 to 30 carbon atoms, or a derivative thereof.

In the present disclosure, the aryl group is not particularly limited, but preferably has 6 to 60 carbon atoms, and can be a monocyclic aryl group or a polycyclic aryl group. According to one embodiment, the number of carbon atoms of the aryl group is 6 to 30. According to another embodiment, the number of carbon atoms of the aryl group is 6 to 20. The aryl group can be a phenyl group, a biphenyl group, a terphenyl group, or the like as the monocyclic aryl group, but is not limited thereto. The polycyclic aryl group can be a naphthyl group, an anthracenyl group, a phenanthryl group, a pyrenyl group, a perylenyl group, a chrycenyl group, a fluorenyl group, or the like, but is not limited thereto.

In the present disclosure, the fluorenyl group can be substituted, and two substituents can be linked with each other to form a spiro structure. In the case where the fluorenyl group is substituted,

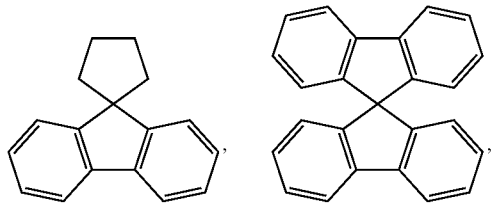

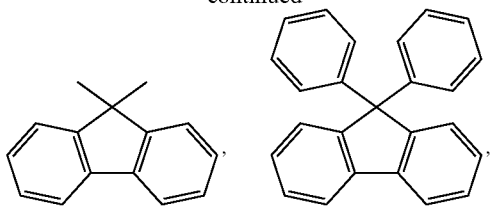

and the like can be formed. However, the structure is not limited thereto.

In the present disclosure, the heterocyclic group is a cyclic group containing at least one of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aforementioned description of the aryl group can be applied except that the arylene is a divalent group. Further, the aforementioned description of the heterocyclic group can be applied except that the heteroarylene is a divalent group.

Meanwhile, according to one embodiment of the present disclosure, a compound of Chemical Formula 1 is provided:

[Chemical Formula 1]

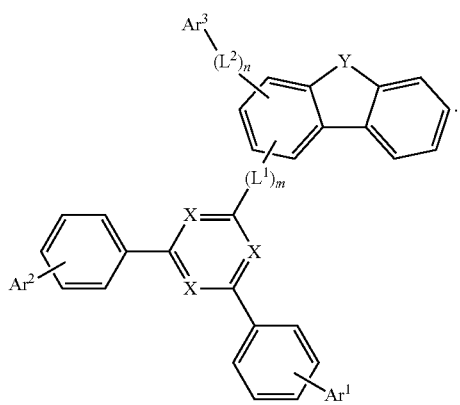

The present inventors conducted extensive studies and found that as the compound of Chemical Formula 1 has the structural features of the above-mentioned chemical formula in which two substituent groups are introduced into either benzene ring of two benzene rings forming dibenzofuran or dibenzothiophene groups, it enables the improvement of the efficiency and the lifetime characteristic of the organic electroluminescent device.

In Chemical Formula 1, each X is independently N or $CR^0$, in which at least two of X are N.

Here, the $R^0$ is hydrogen; deuterium; a $C_{6-50}$ aryl group which is substituted or unsubstituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group; or a $C_{2-50}$ heteroaryl group which contains at least one heteroatom selected from the group consisting of N, O, and S, and which is substituted or unsubstituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group.

Preferably, each X is independently N or CH, in which at least two of X can be N.

In Chemical Formula 1, Y is O or S.

In Chemical Formula 1, $L^1$ and $L^2$ are each independently a direct bond, or a $C_{6-20}$ arylene group which is unsubstituted or substituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group.

In Chemical Formula 1, m and n are each independently an integer of 0 to 2. Specifically, m and n can each independently be 0 or 1.

In Chemical Formula 1, $Ar^1$ and $Ar^2$ are each independently hydrogen, deuterium, a $C_{6-50}$ aryl group which is substituted or unsubstituted by deuterium, a halogen, an amino group, a nitrile group, a nitro group, a $C_{1-30}$ alkyl group, a $C_{2-30}$ alkenyl group, a $C_{2-30}$ alkynyl group, a $C_{1-30}$ alkoxy group, a $C_{6-30}$ aryloxy group, or a $C_{6-30}$ aryl group, or a $C_{2-50}$ heteroaryl group which contains at least one heteroatom selected from the group consisting of N, O, and S, and which is substituted or unsubstituted by a $C_{6-30}$ aryloxy group.

Preferably, $Ar^1$ and $Ar^2$ are each independently hydrogen or a $C_{6-50}$ aryl group.

In Chemical Formula 1, $Ar^3$ is a $C_{6-60}$ aryl group.

Specifically, $Ar^3$ can be a phenyl group, a biphenyl group, a terphenyl group, a naphthyl group, an anthracenyl group, a phenanthryl group, a pyrenyl group, a perylenyl group, a chrycenyl group, or a substituted or unsubstituted fluorenyl group.

Specifically, Chemical Formula 1 is any one of the following Chemical Formulas 1-1 to 1-6:

[Chemical Formula 1-1]

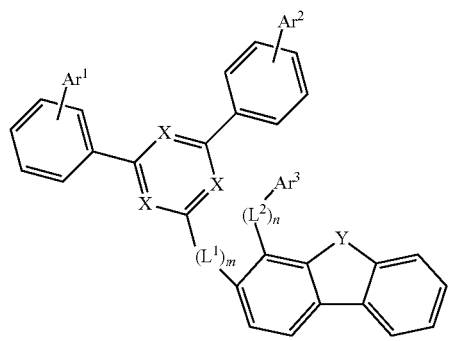

[Chemical Formula 1-2]
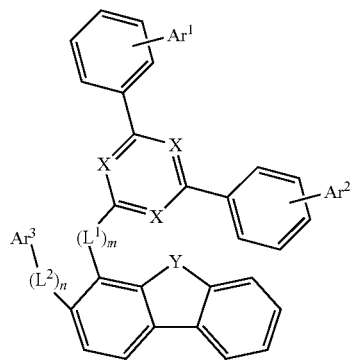
[Chemical Formula 1-3]
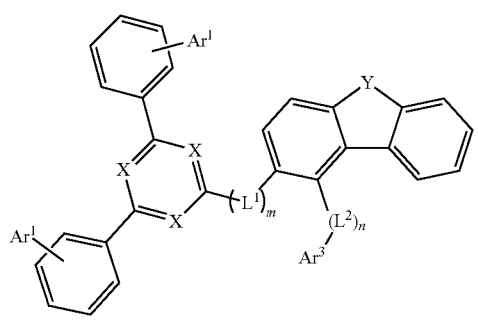
[Chemical Formula 1-4]
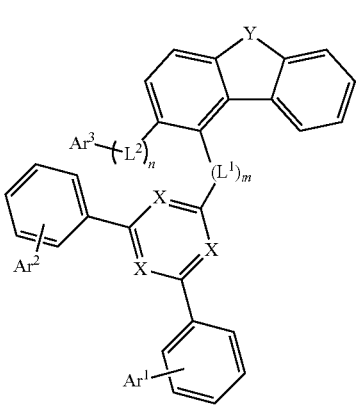
[Chemical Formula 1-5]
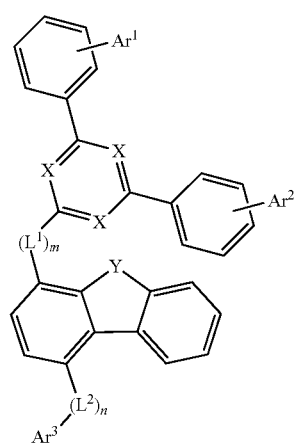
[Chemical Formula 1-6]
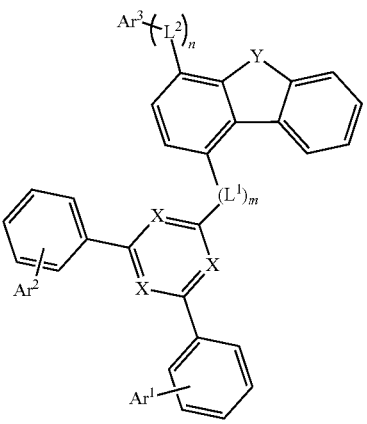
wherein, in Chemical Formulas 1-1 to 1-6:
X, Y, $L^1$, $L^2$, m, n, $Ar^1$, $Ar^2$, and $Ar^3$ are the same as those defined in Chemical Formula 1.
Representative examples of the compound of Chemical Formula 1 are as follows:
1-1-1
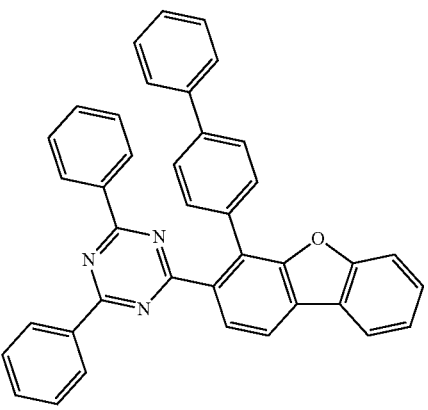
1-1-2
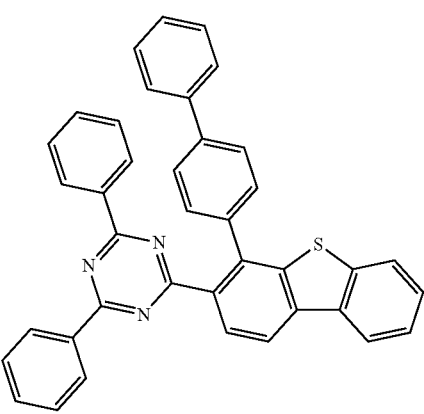

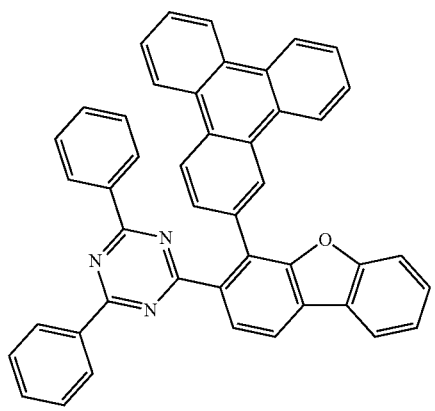
1-1-3
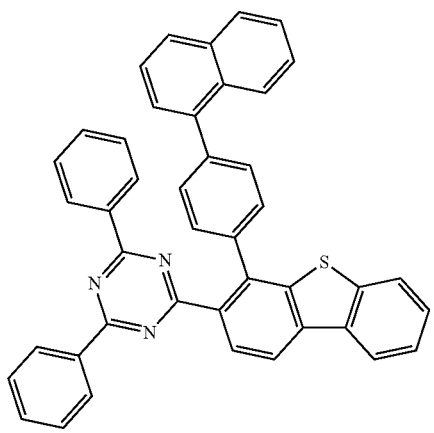
1-1-6
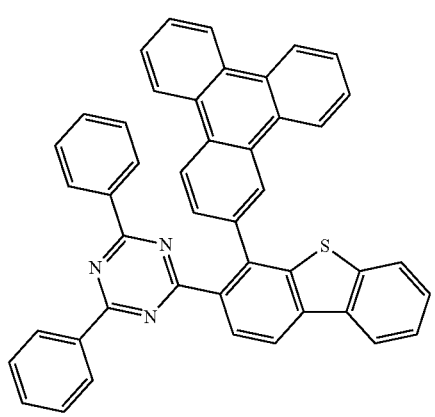
1-1-4
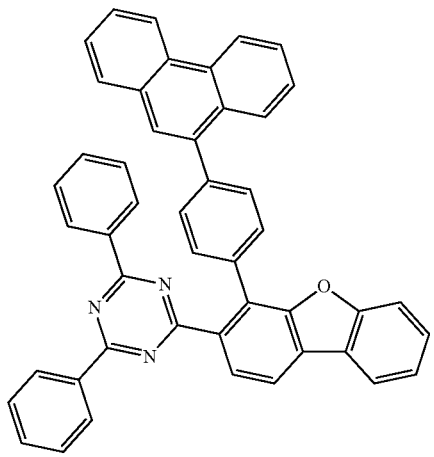
1-1-7
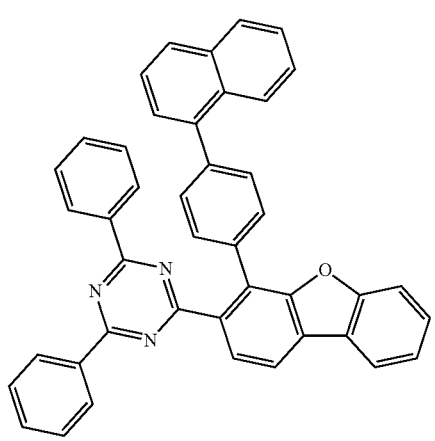
1-1-5
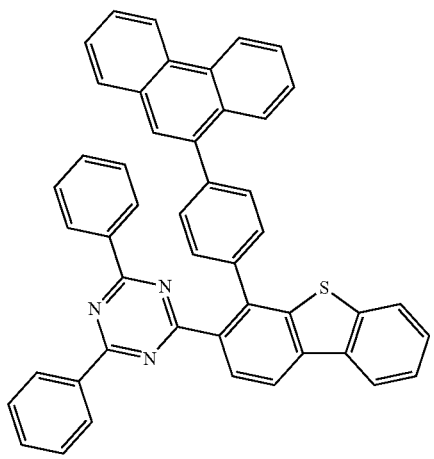
1-1-8

1-1-9
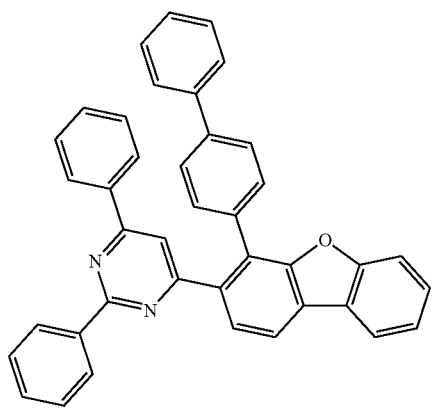
1-1-10
1-1-13
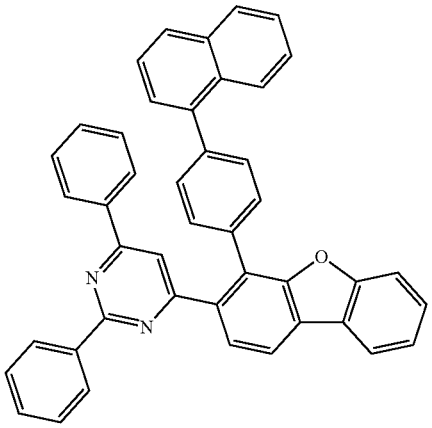
1-1-11
1-1-14
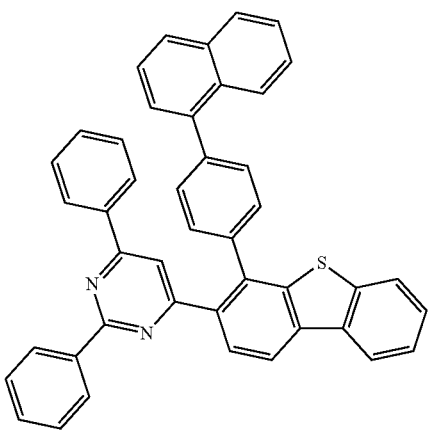
1-1-12
1-1-15
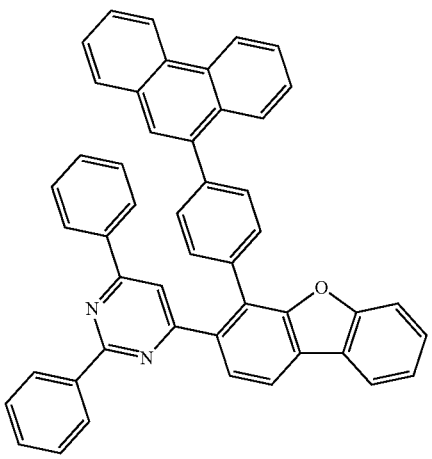

1-1-16
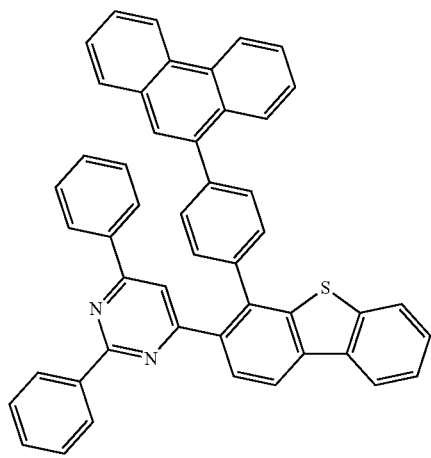
1-1-17
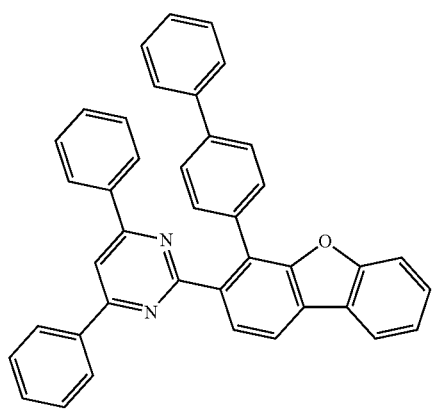
1-1-18
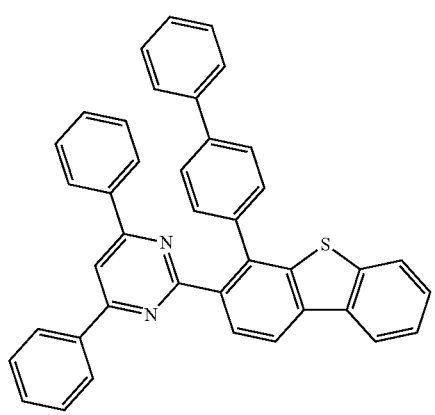
1-1-19
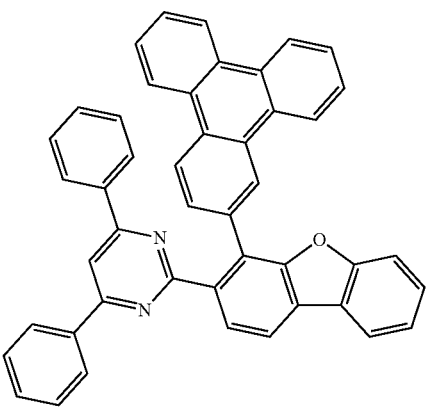
1-1-20
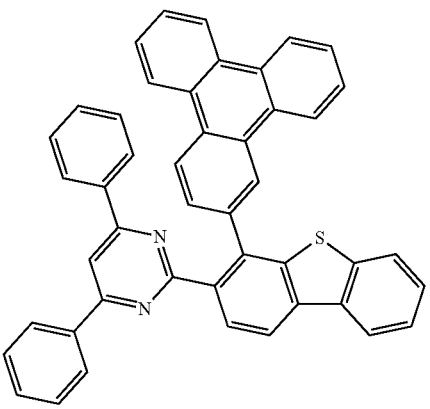
1-1-21
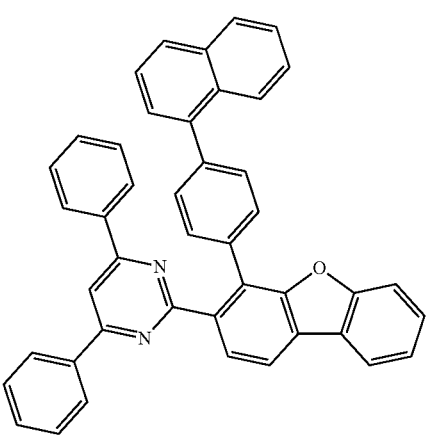

1-1-22
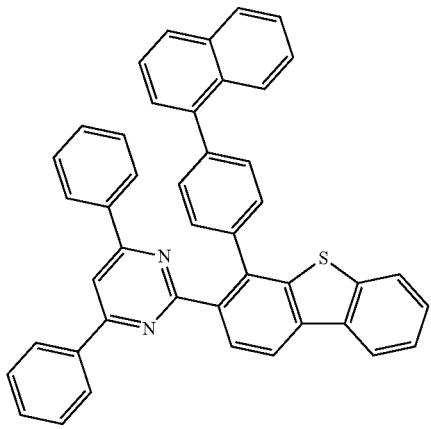
1-1-23
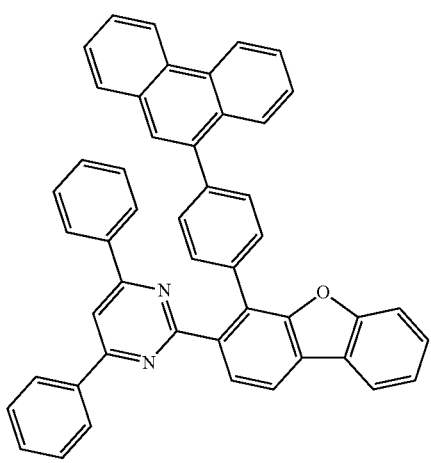
1-1-24
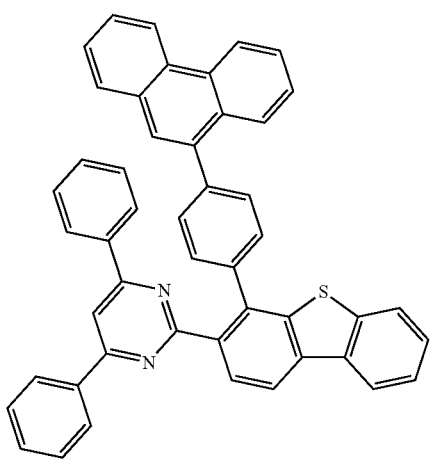
1-1-25
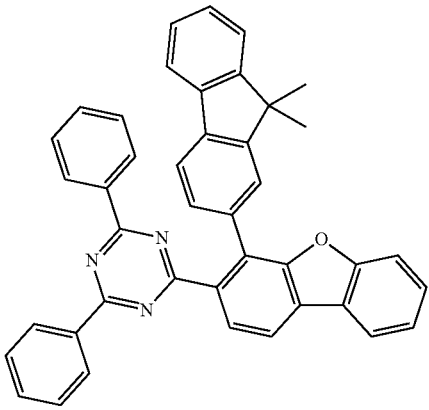
1-1-26
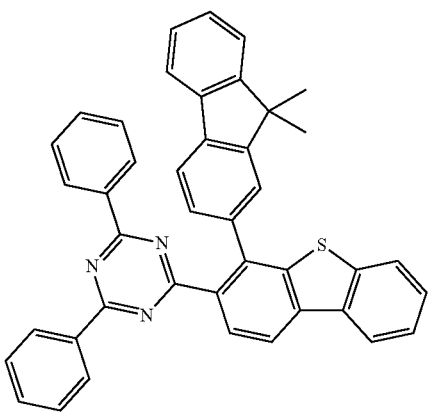
1-1-27
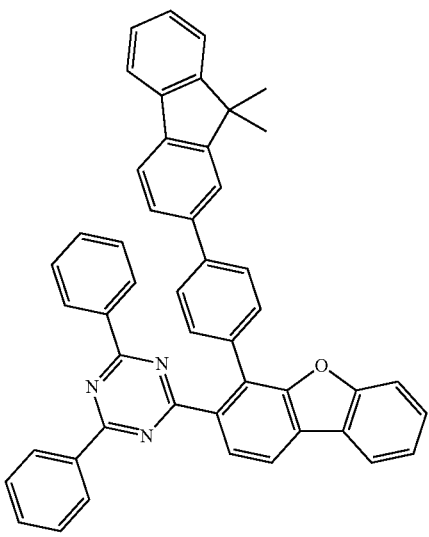

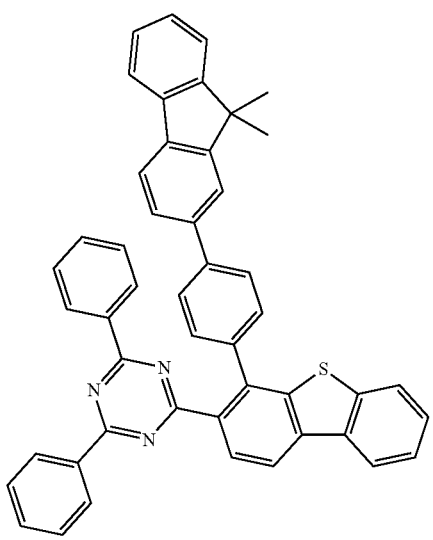
1-1-28
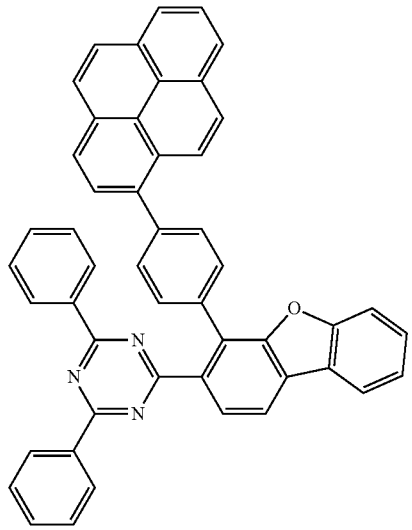
1-1-31
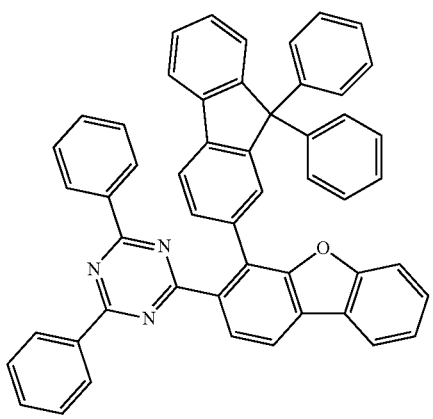
1-1-29
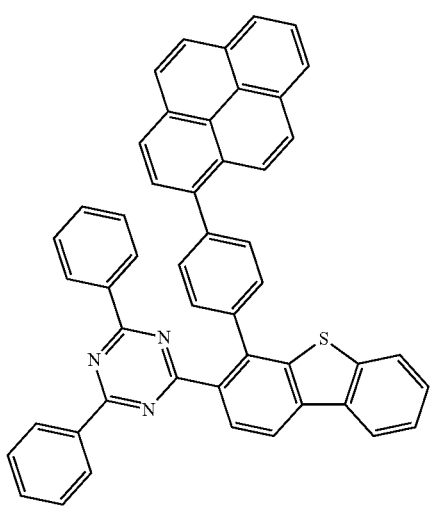
1-1-32
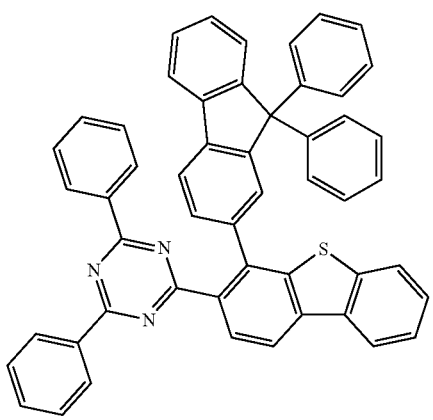
1-1-30
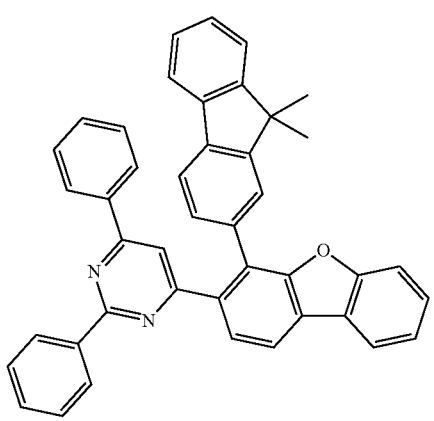
1-1-33

-continued
1-1-34
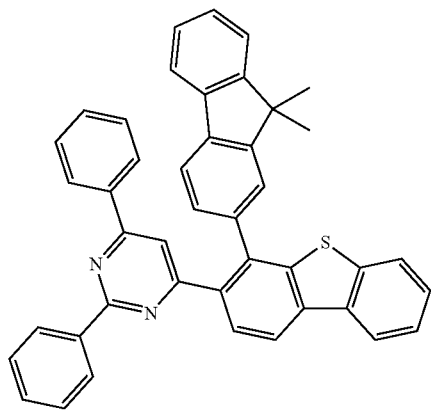
1-1-35
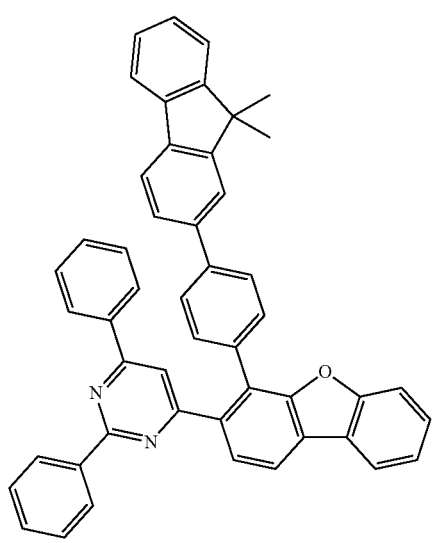
1-1-36
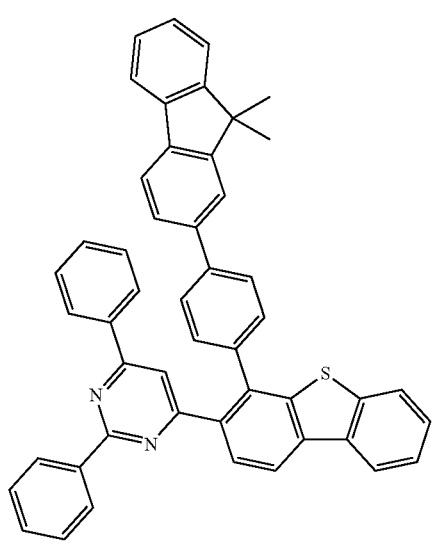
-continued
1-1-37
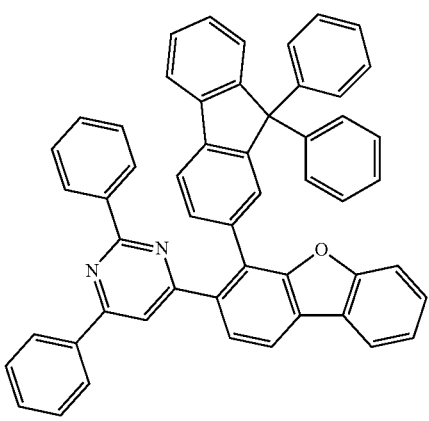
1-1-38
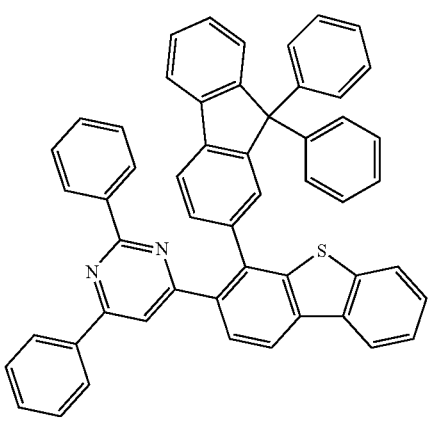
1-1-39
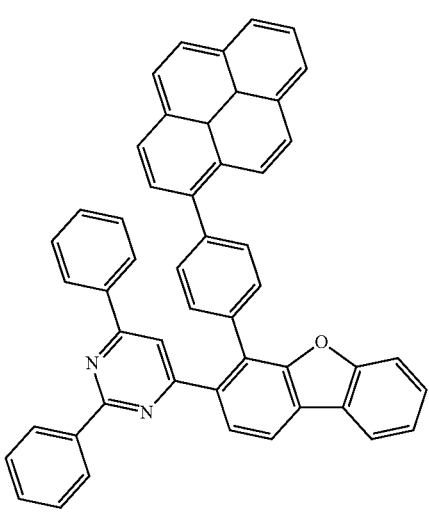

-continued
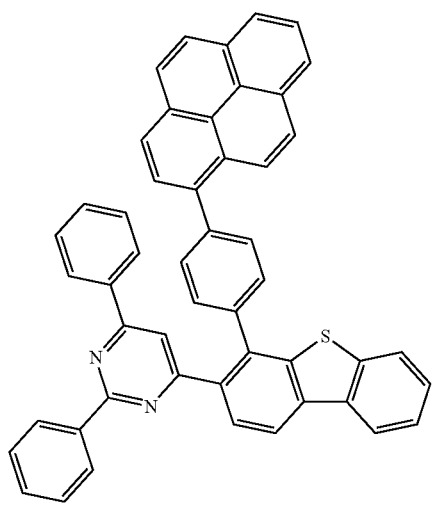
1-1-40
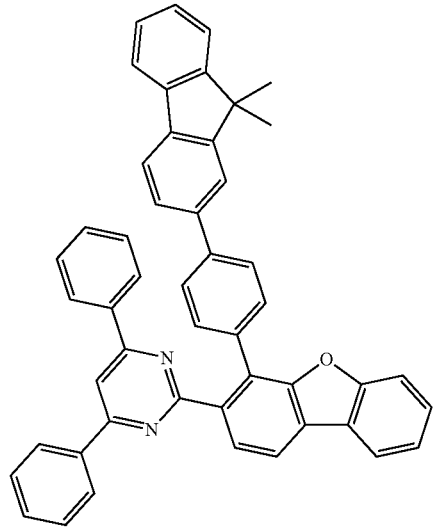
1-1-43
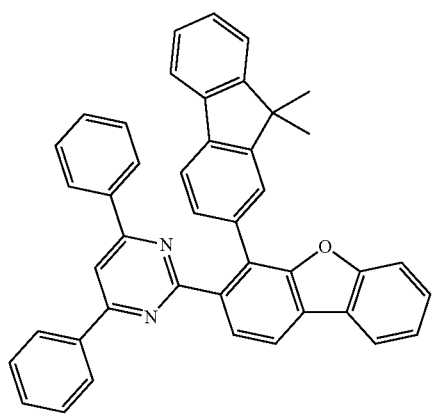
1-1-41
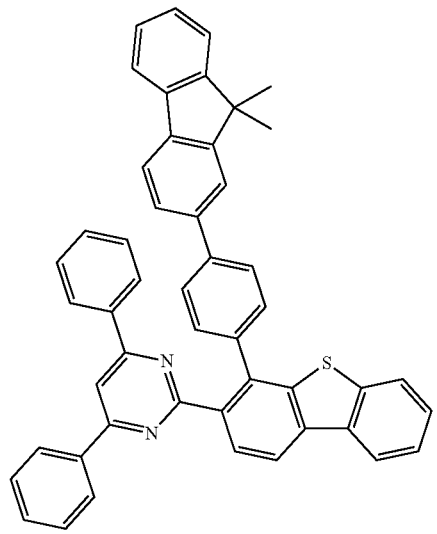
1-1-44
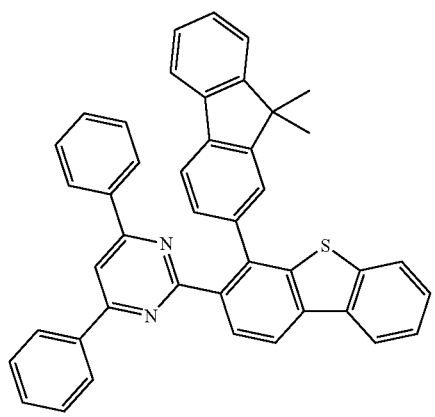
1-1-42
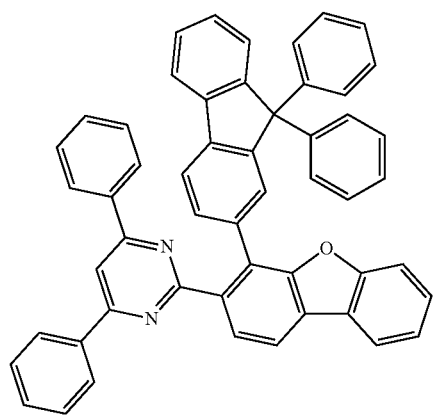
1-1-45

1-1-46
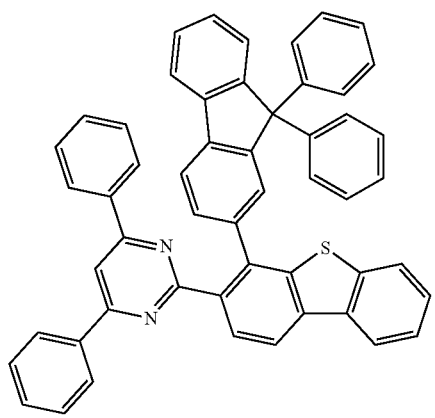
1-1-47
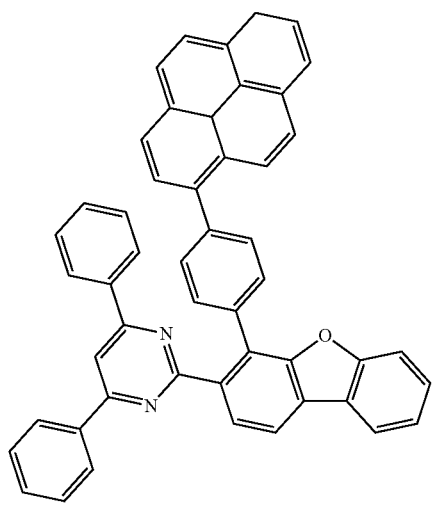
1-1-48
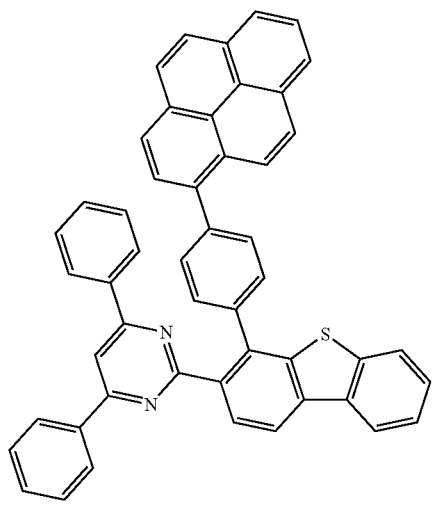
1-1-49
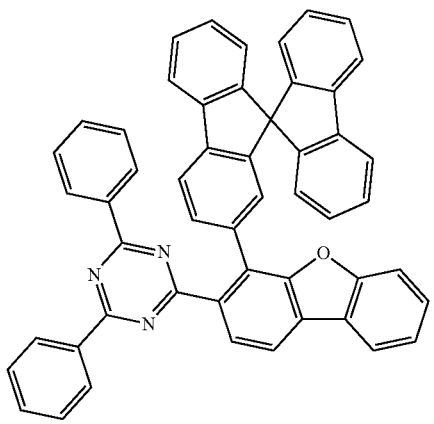
1-1-50
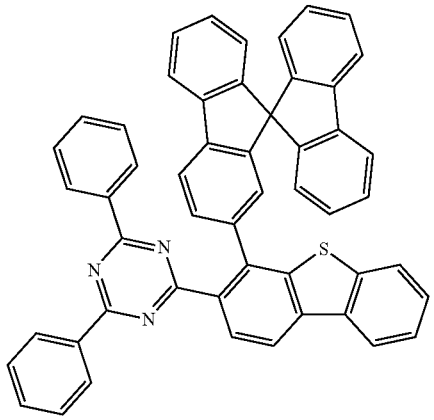
1-1-51
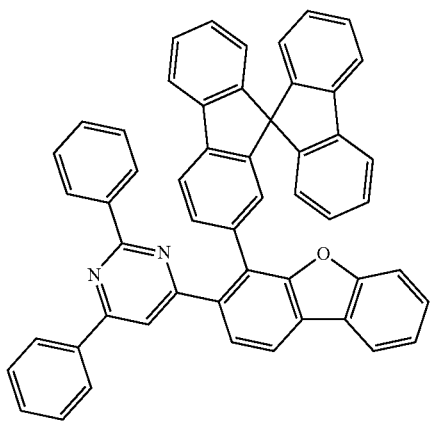

1-1-52
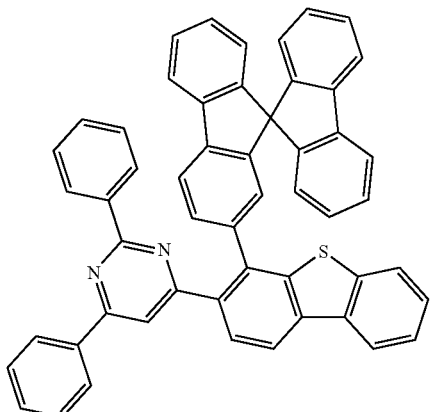
1-1-53
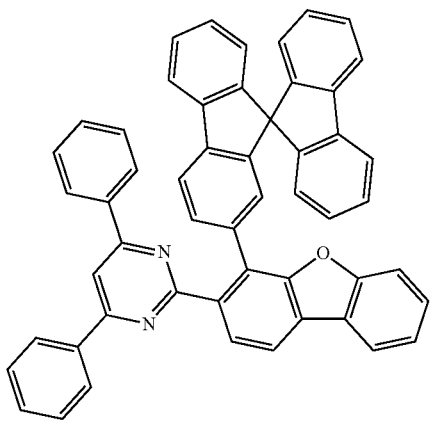
1-1-54
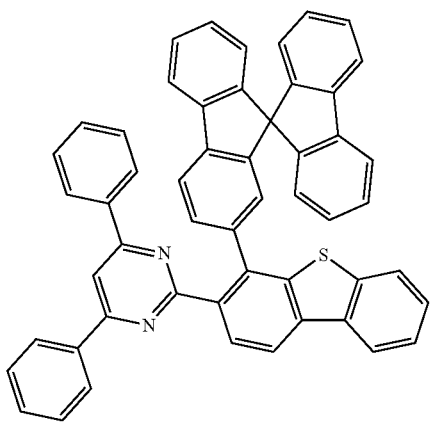
1-1-55
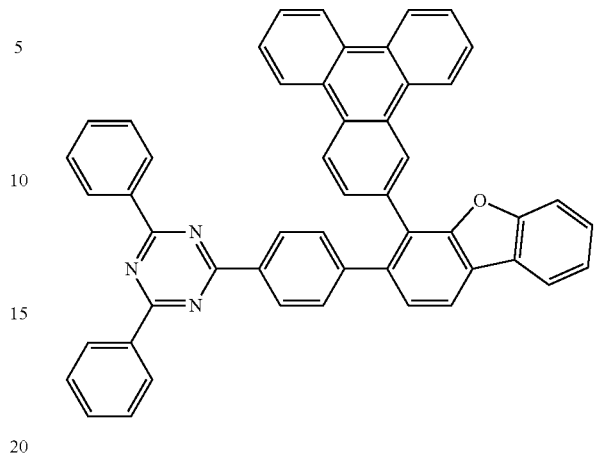
1-1-56
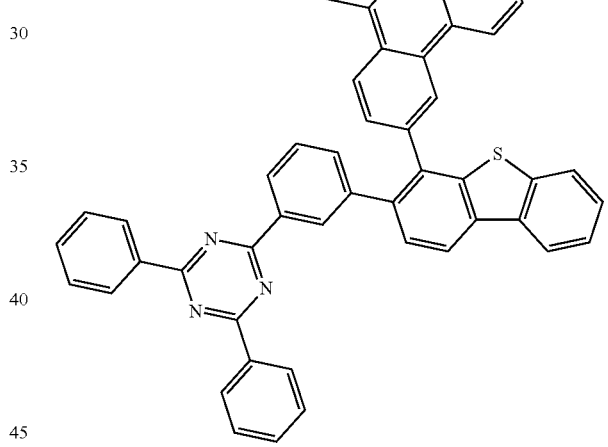
1-1-57
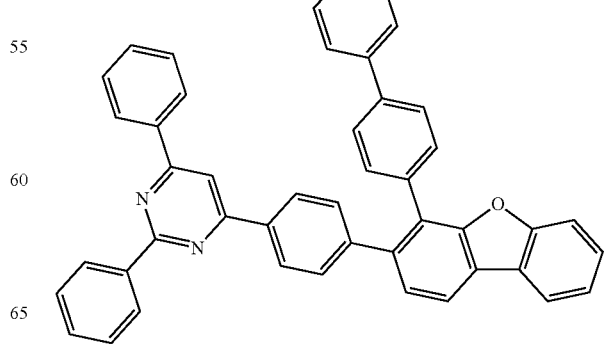

1-1-58
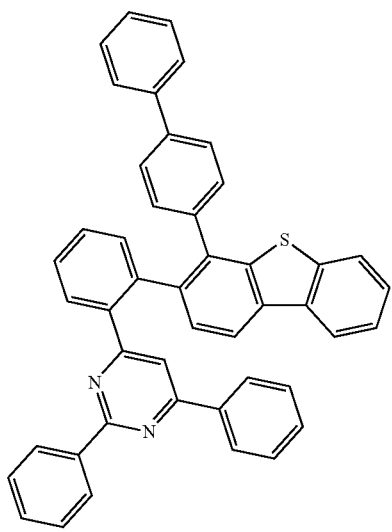
1-1-59
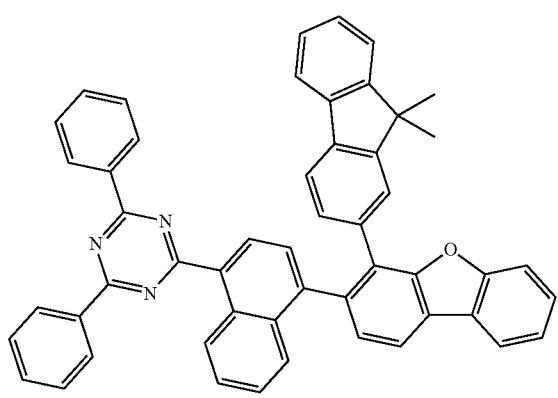
1-1-60
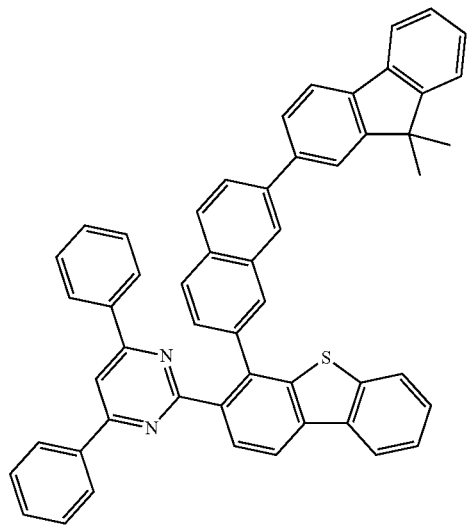
1-1-61
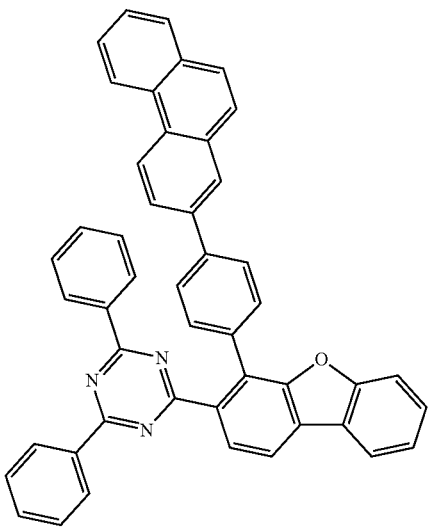
1-1-62
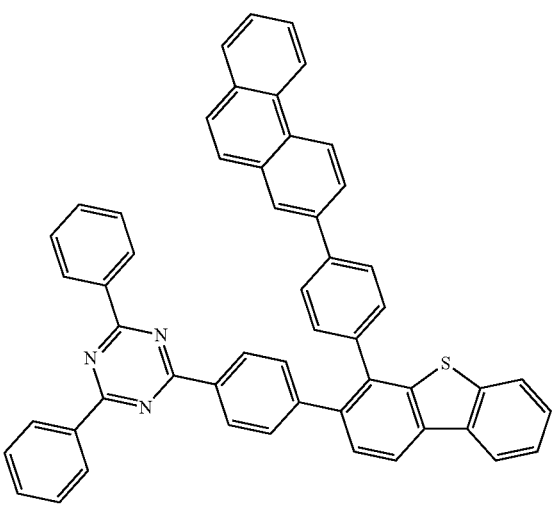
1-1-63
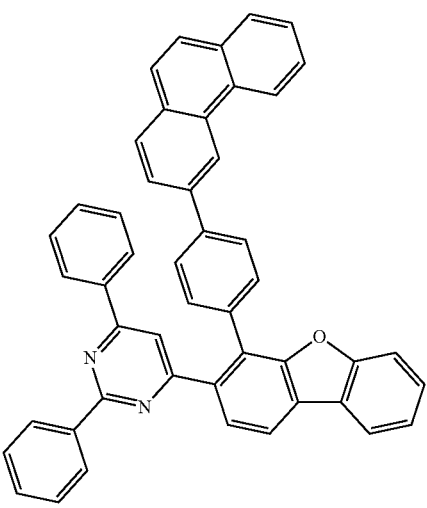

-continued
1-1-64
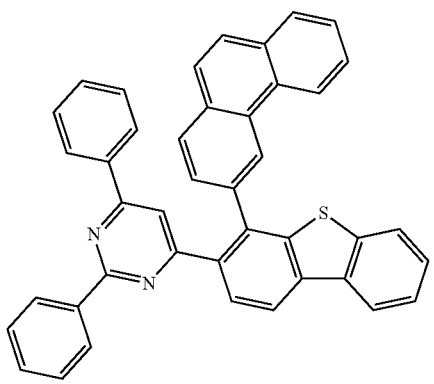
1-2-1
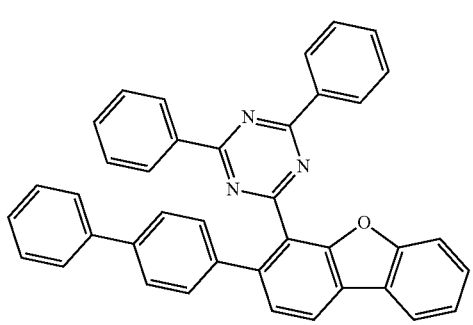
1-2-2
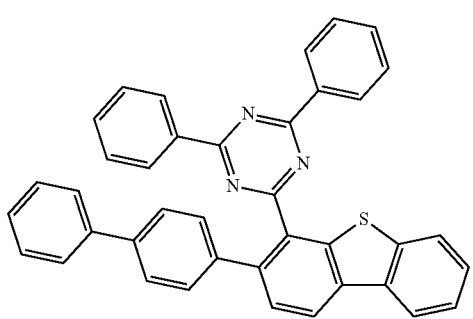
1-2-3
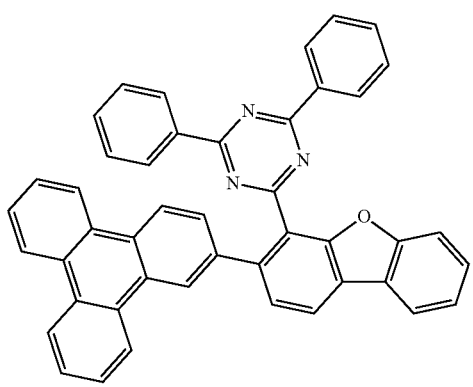
-continued
1-2-4
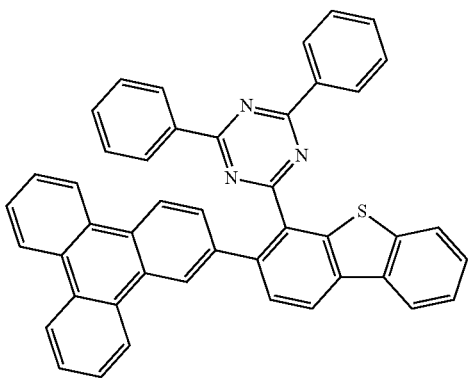
1-2-5
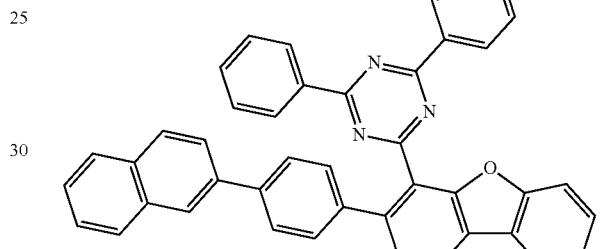
1-2-6
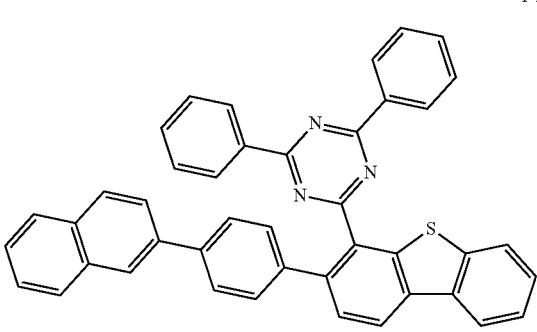
1-2-7
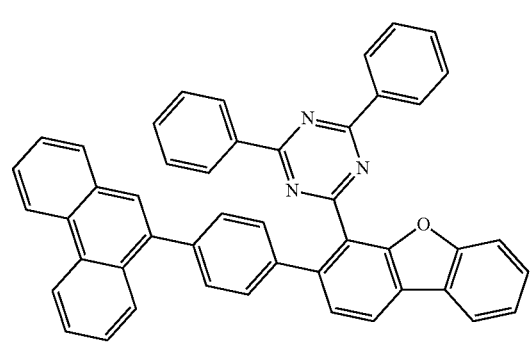

1-2-8
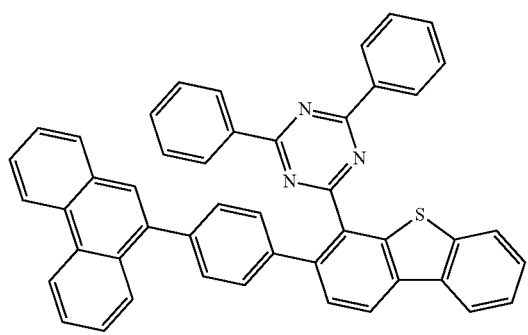
1-2-9
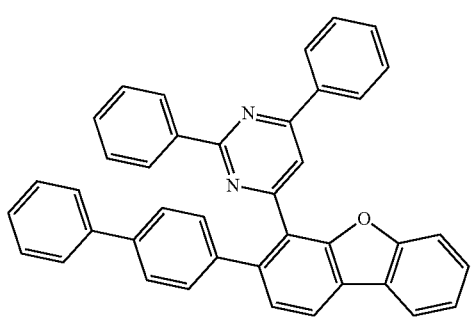
1-2-10
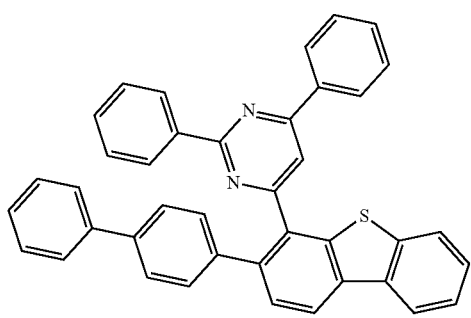
1-2-11
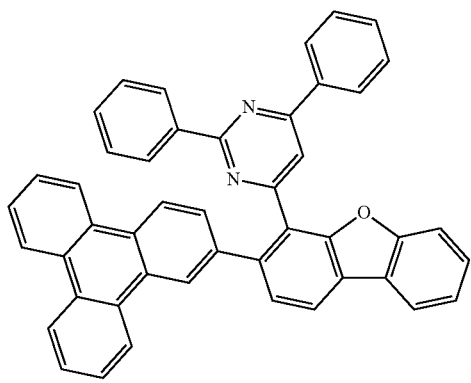
1-2-12
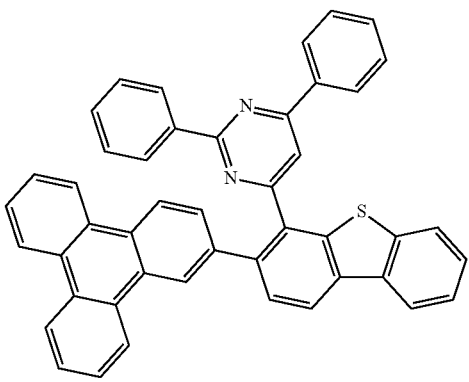
1-2-13
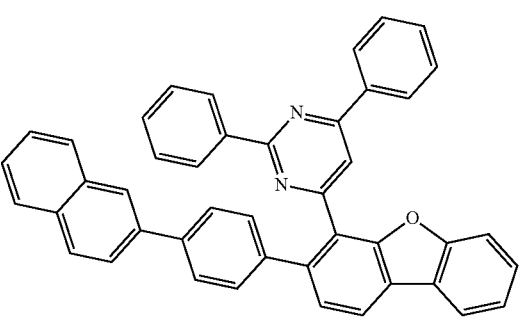
1-2-14
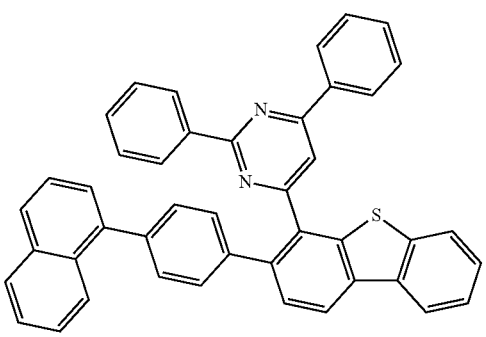
1-2-15
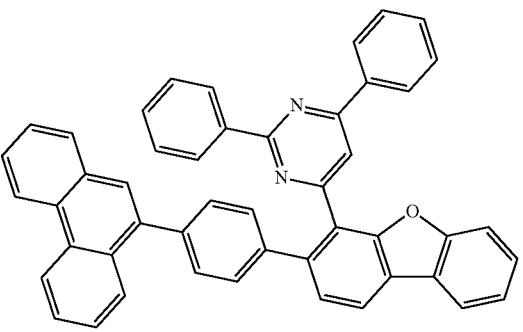

-continued
1-2-16
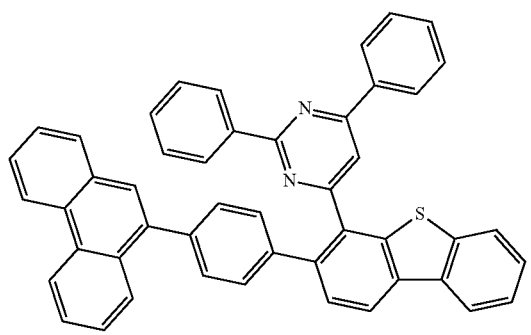
1-2-17
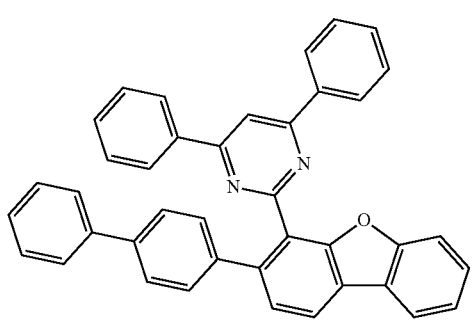
1-2-18
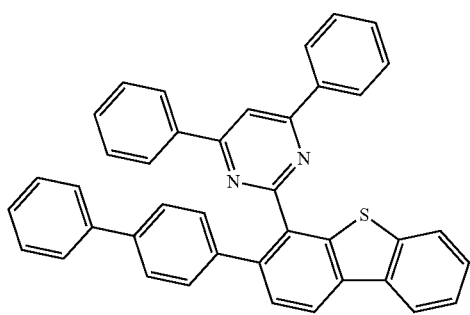
1-2-19
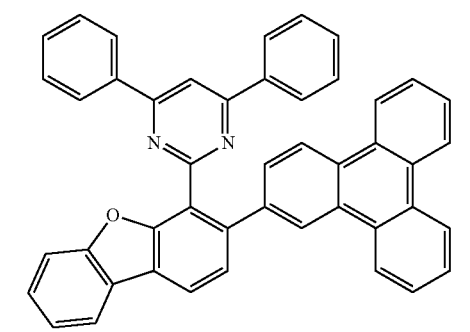
-continued
1-2-20
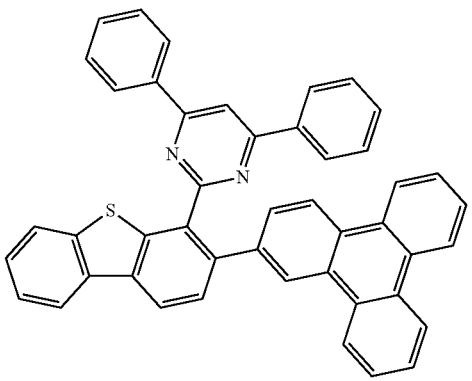
1-2-21
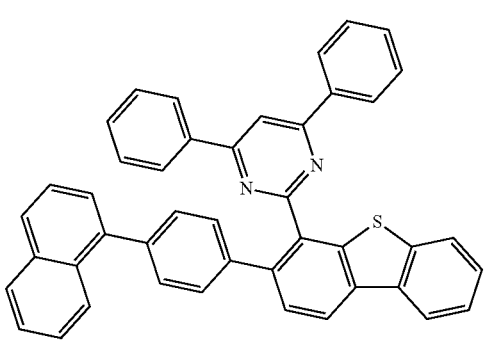
1-2-22
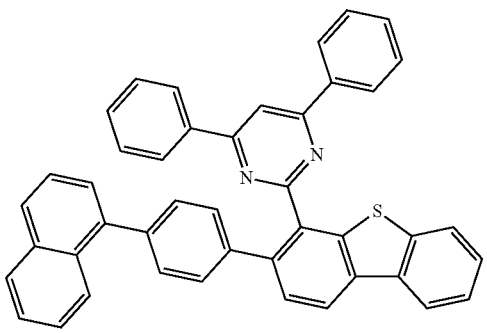
1-2-23
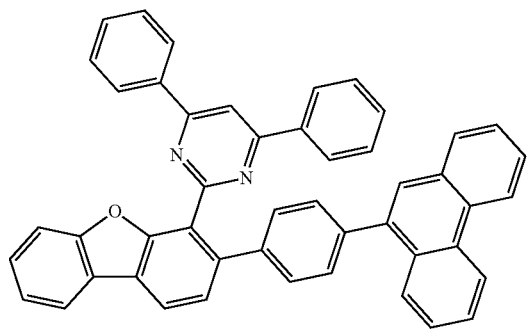

1-2-24
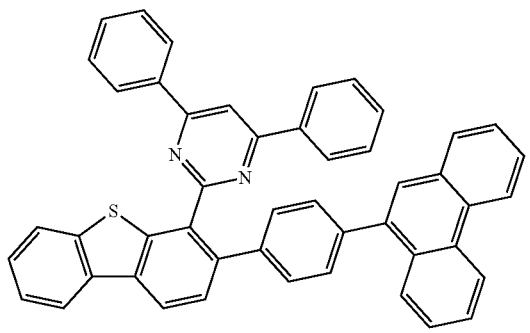
1-2-25
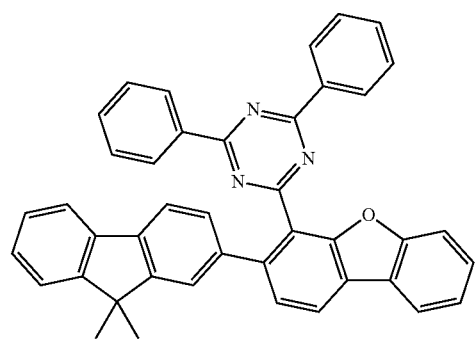
1-2-26
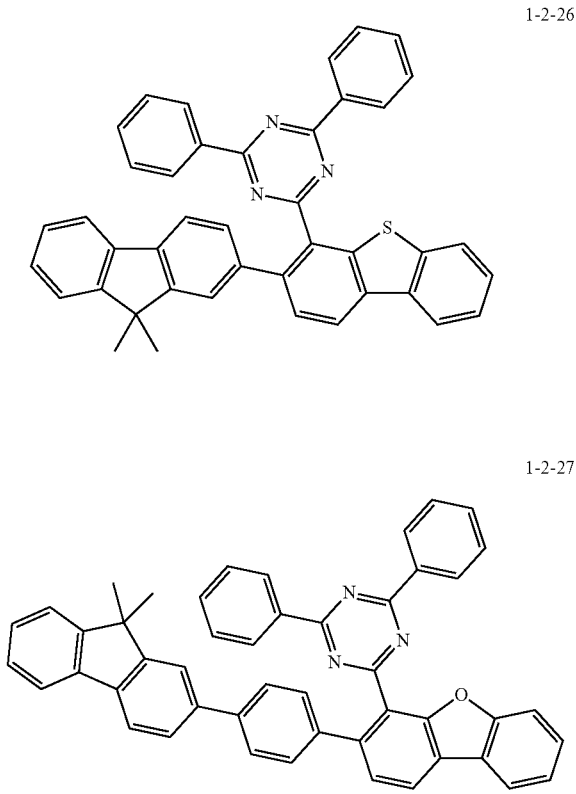
1-2-27
1-2-28
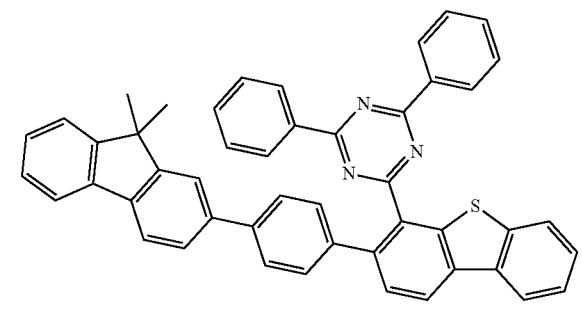
1-2-29
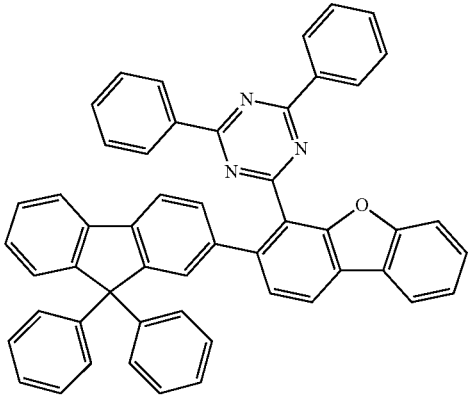
1-2-30
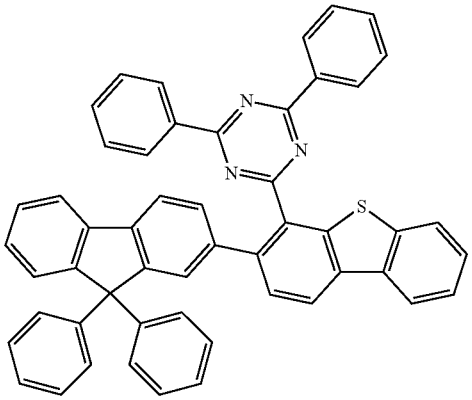
1-2-31

1-2-32
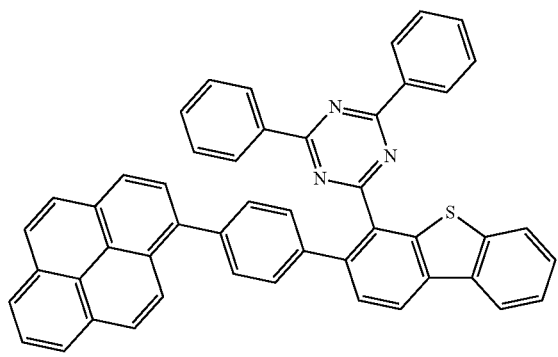
1-2-36
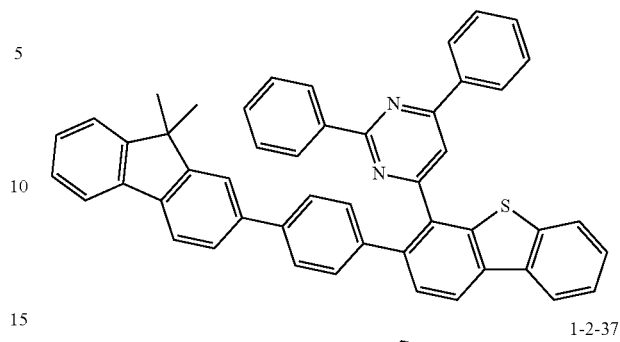
1-2-33
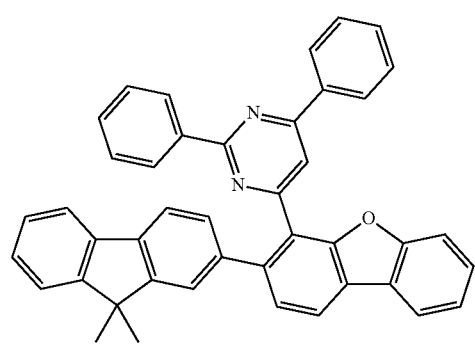
1-2-37
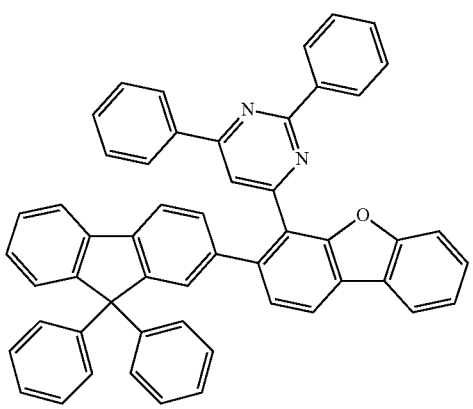
1-2-34
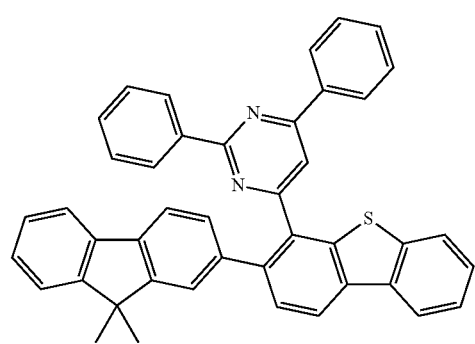
1-2-38
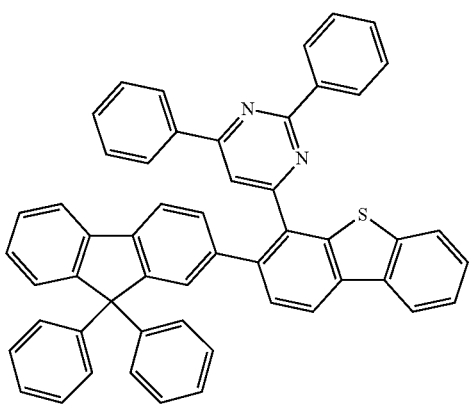
1-2-35
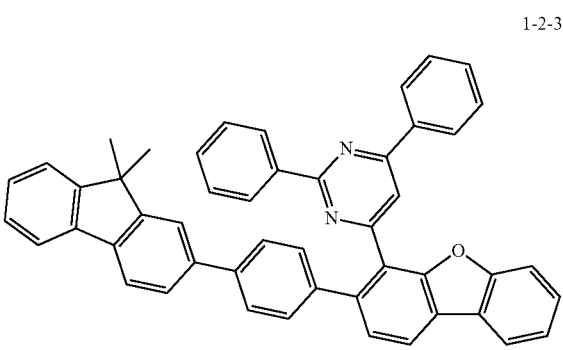
1-2-39
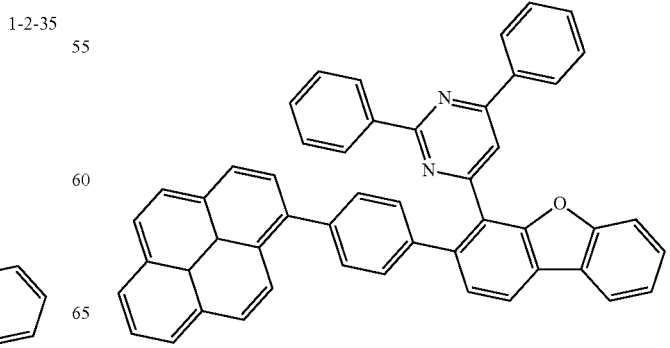

-continued
1-2-40
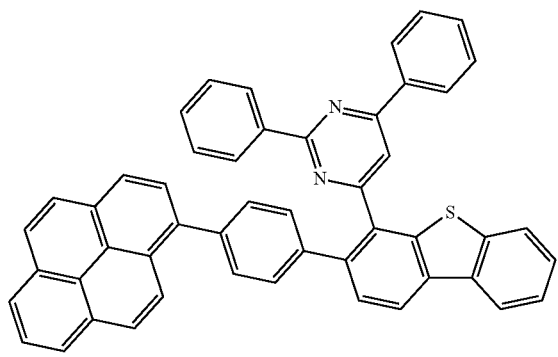
1-2-41
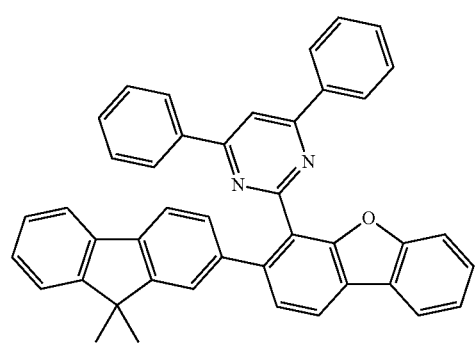
1-2-42
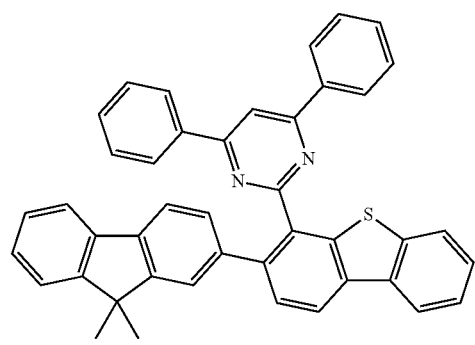
1-2-43
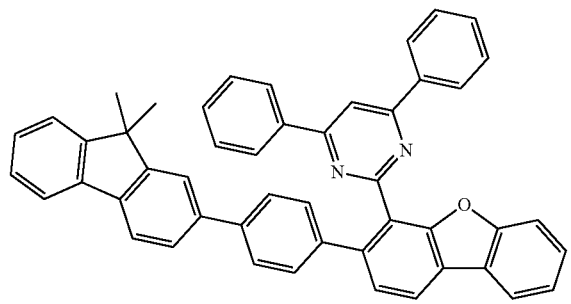
1-2-44
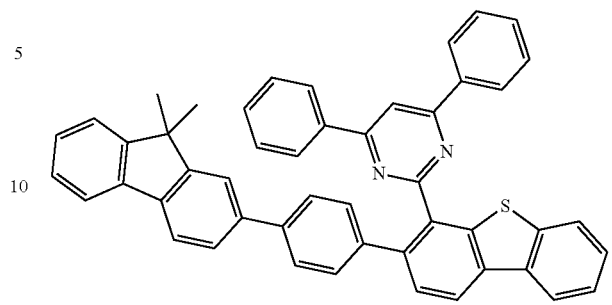
1-2-45
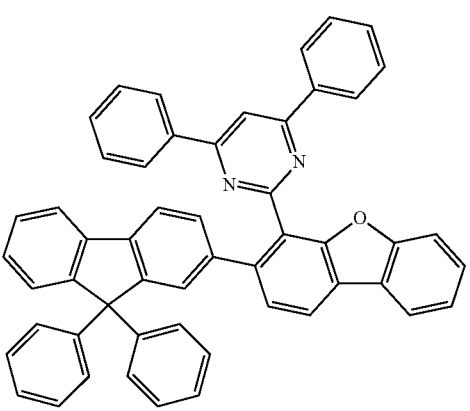
1-2-46
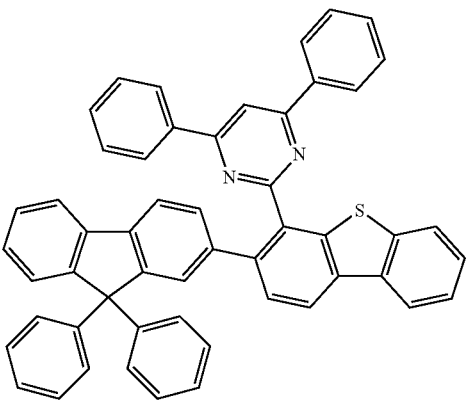
1-2-47
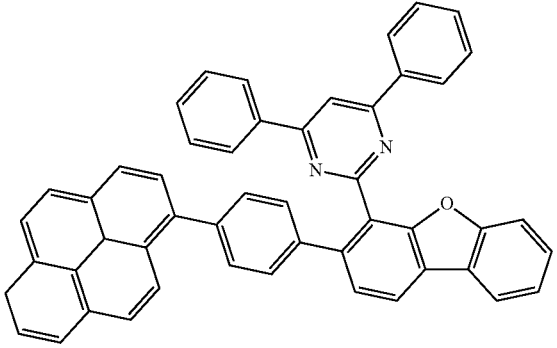

1-2-48
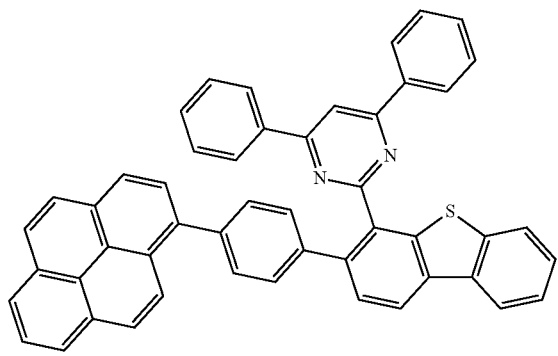
1-2-49
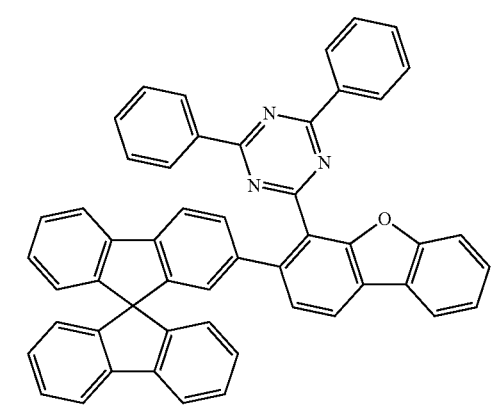
1-2-50
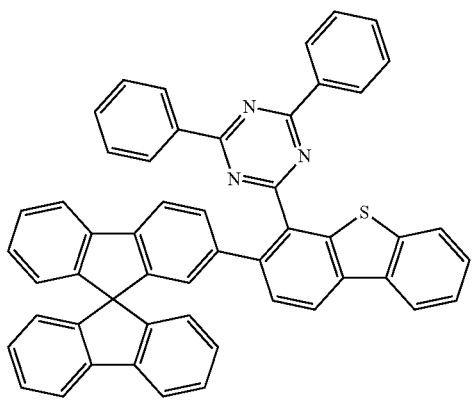
1-2-51
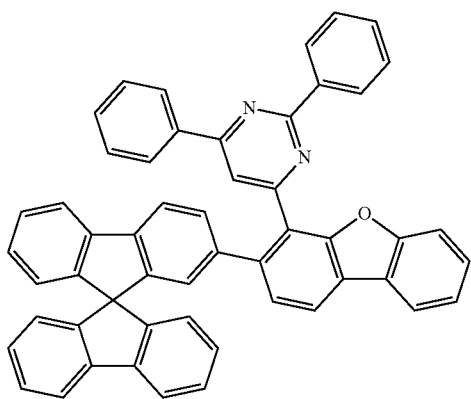
1-2-52
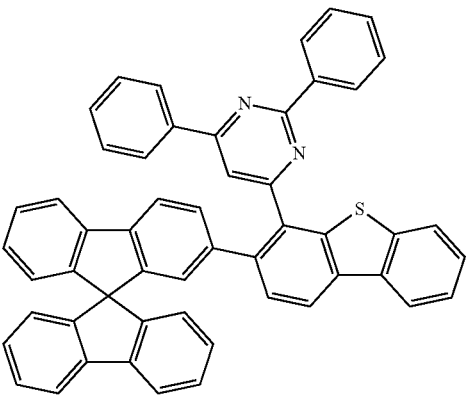
1-2-53
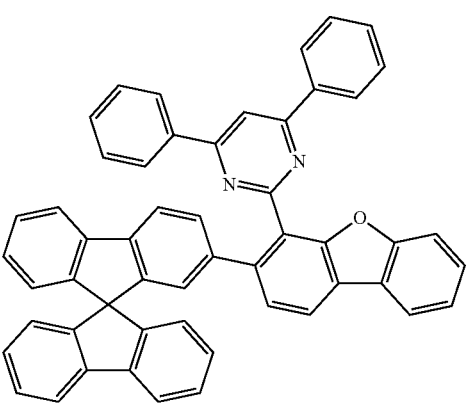
1-2-54
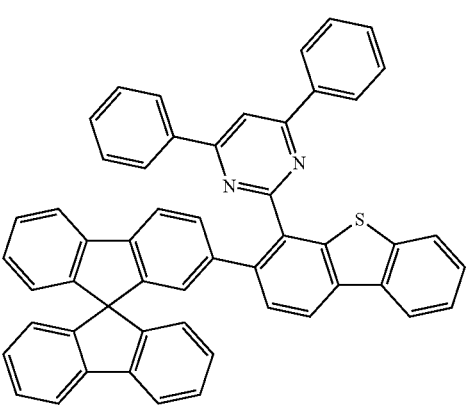
1-2-55
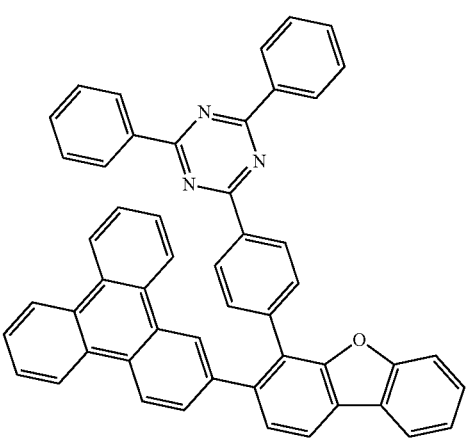

-continued
1-2-56
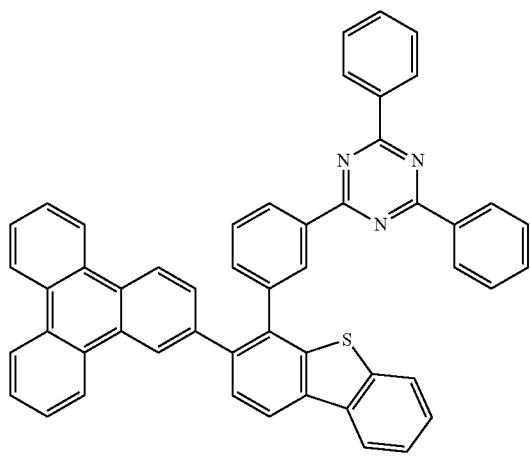
1-2-57
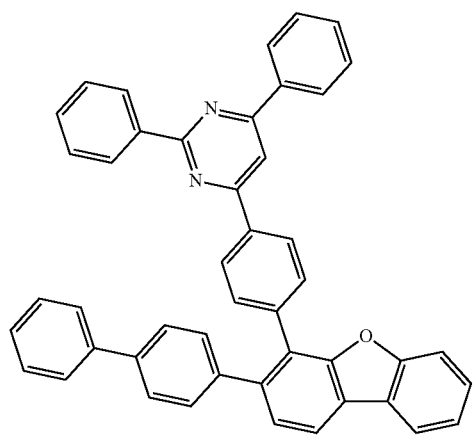
1-2-58
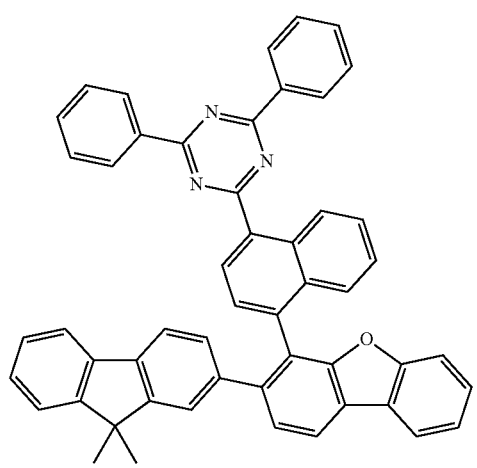
1-2-59
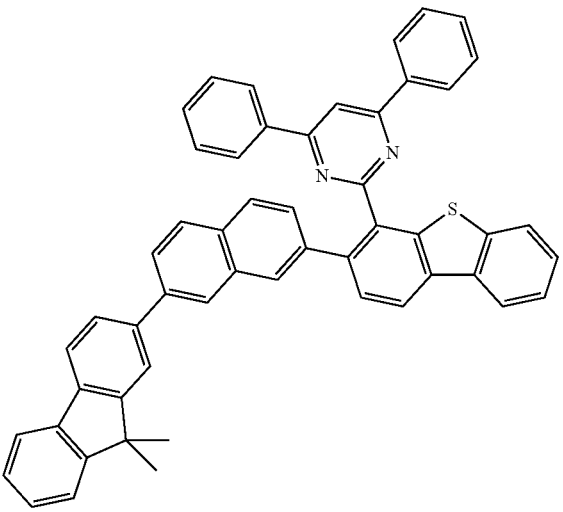
1-2-60
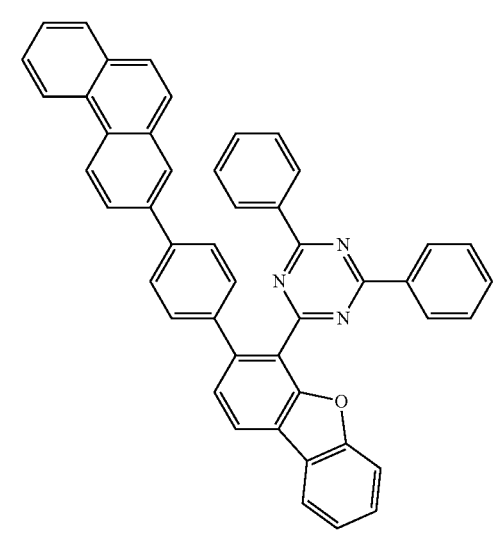
1-2-61
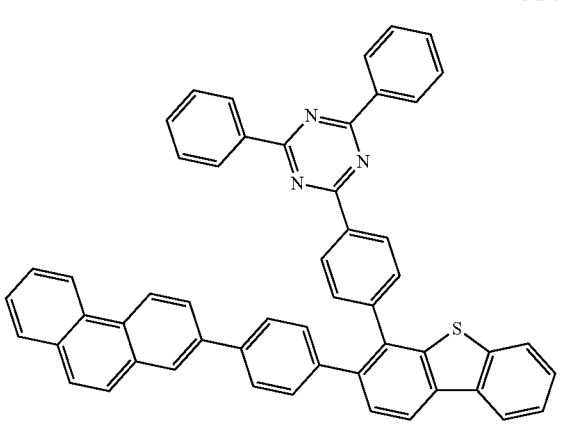

-continued
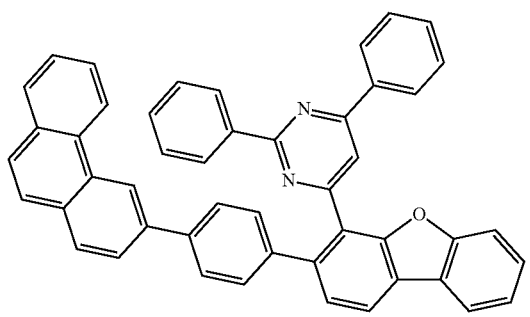
1-2-62
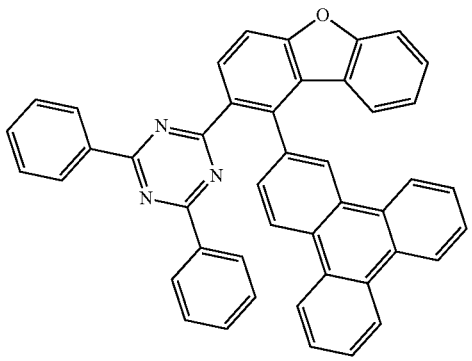
1-3-3
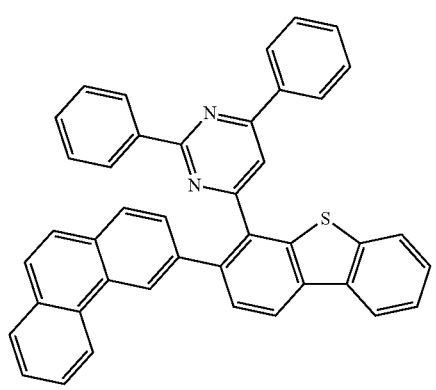
1-2-63
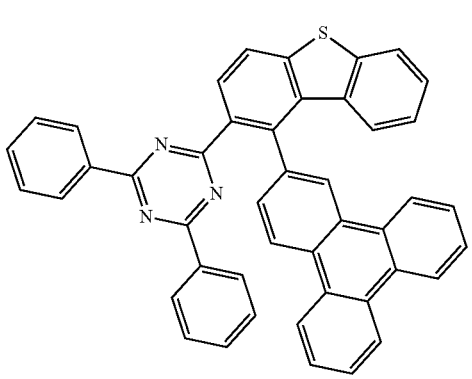
1-3-4
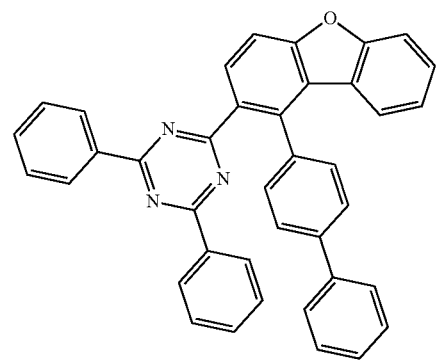
1-3-1
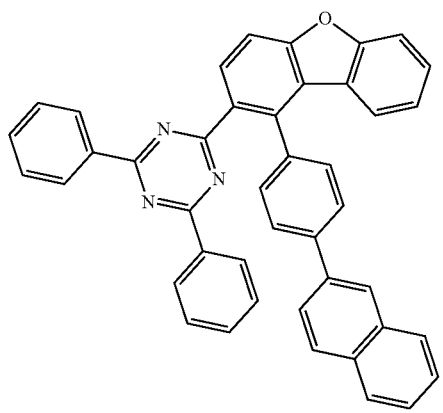
1-3-5
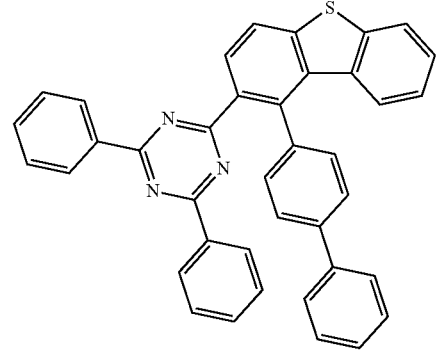
1-3-2
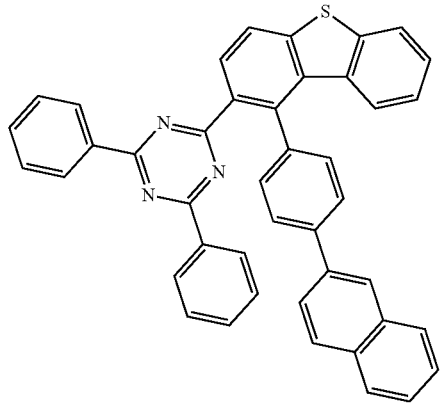
1-3-6

1-3-7
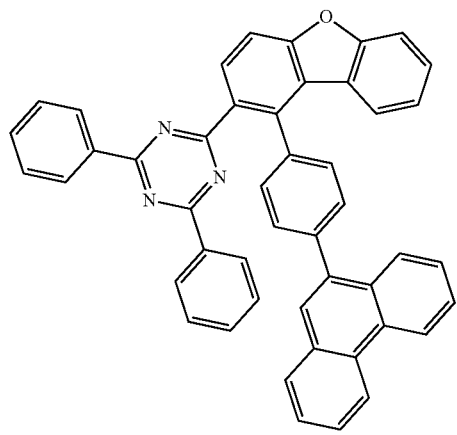
1-3-11
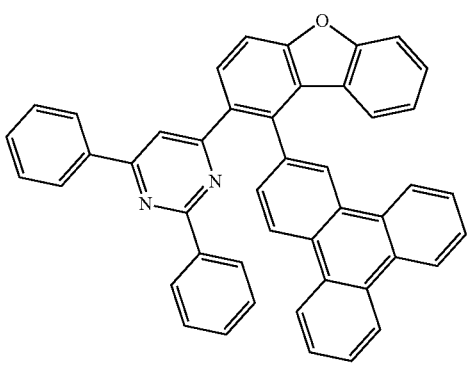
1-3-8
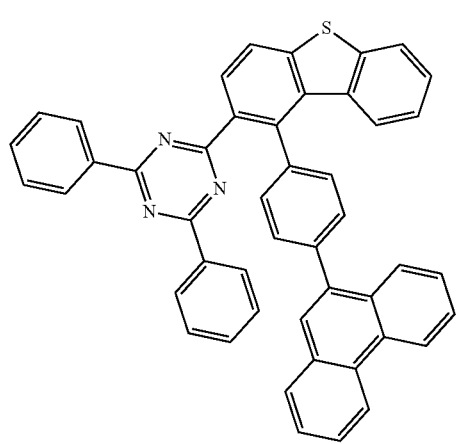
1-3-12
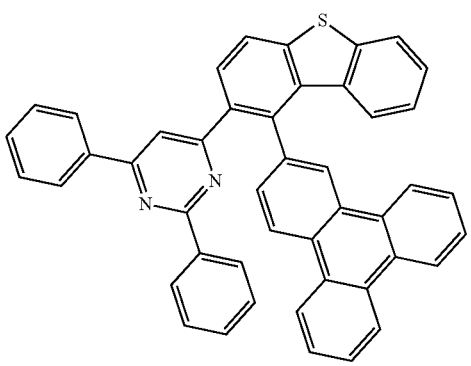
1-3-9
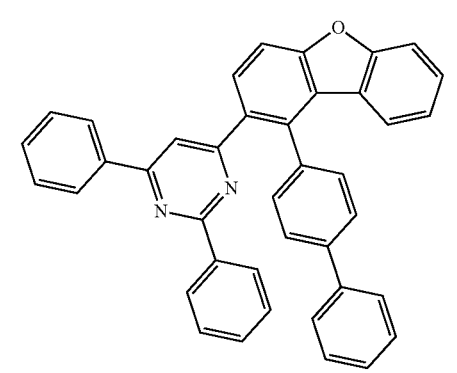
1-3-13
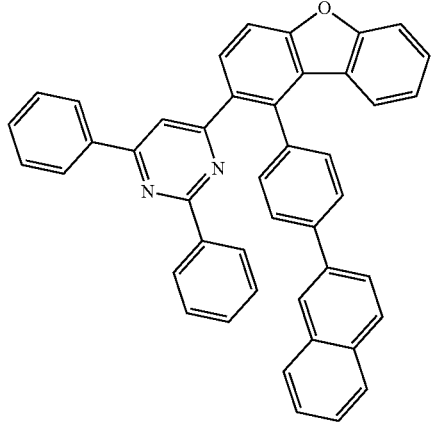
1-3-10
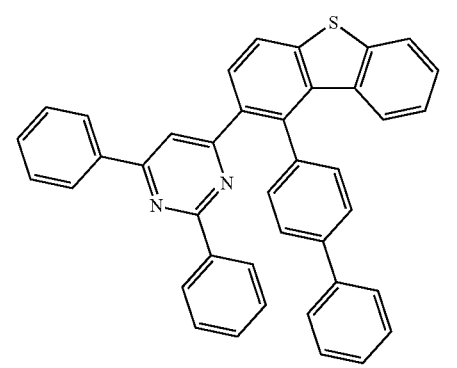
1-3-14
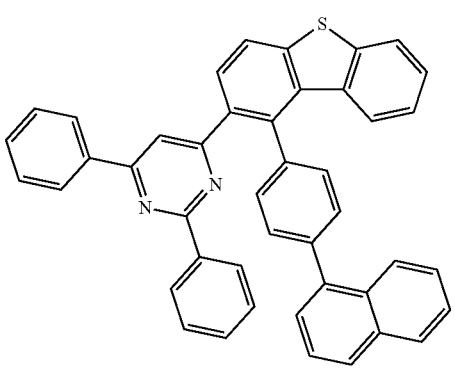

-continued
1-3-15
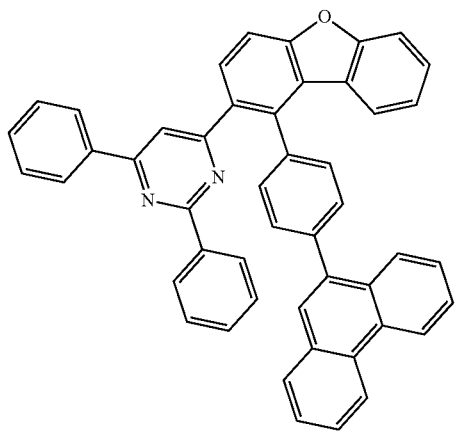
1-3-16
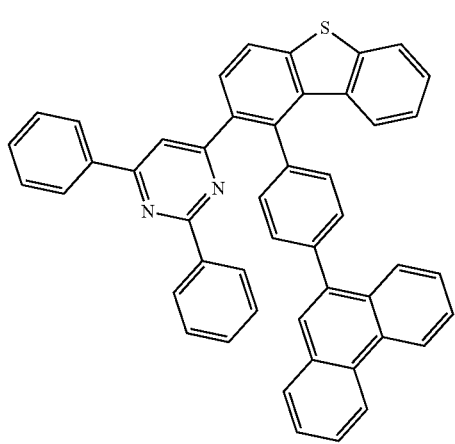
1-3-17
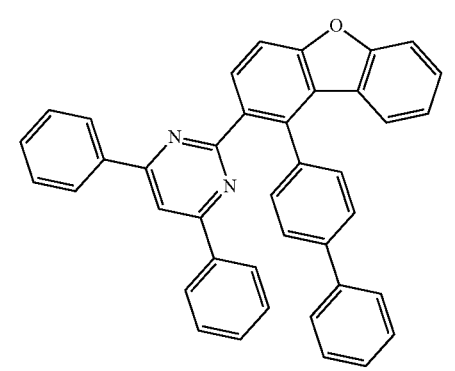
1-3-18
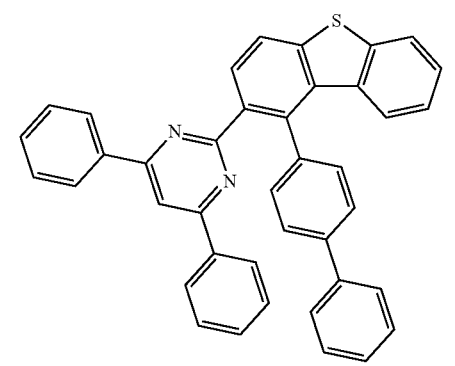
-continued
1-3-19
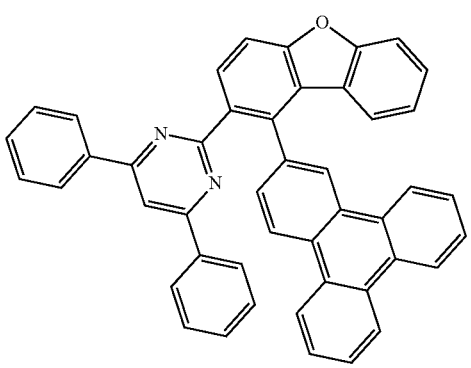
1-3-20
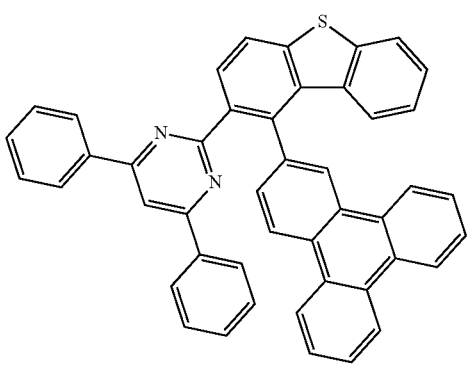
1-3-21
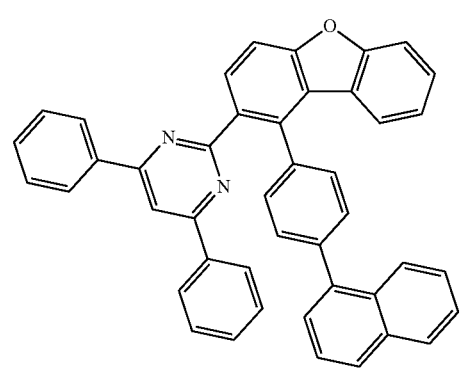
1-3-22
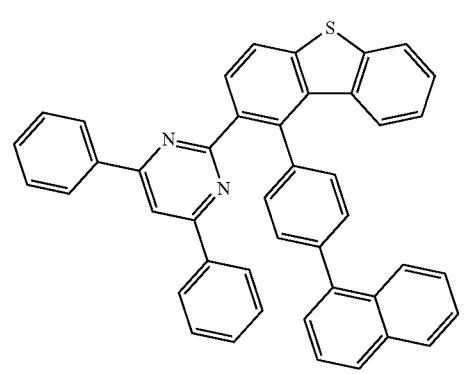

1-3-23
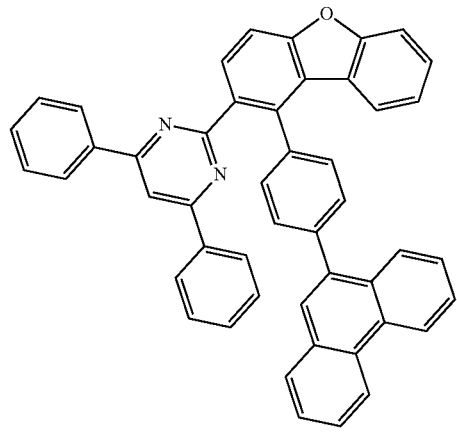
1-3-24
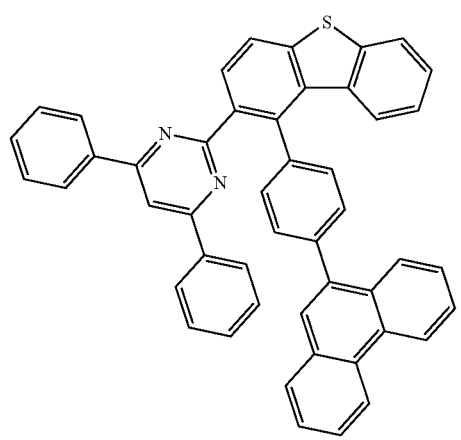
1-3-25
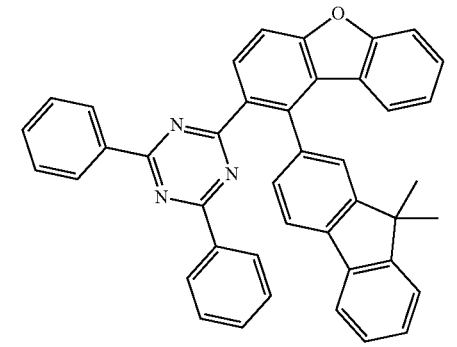
1-3-26
1-3-27
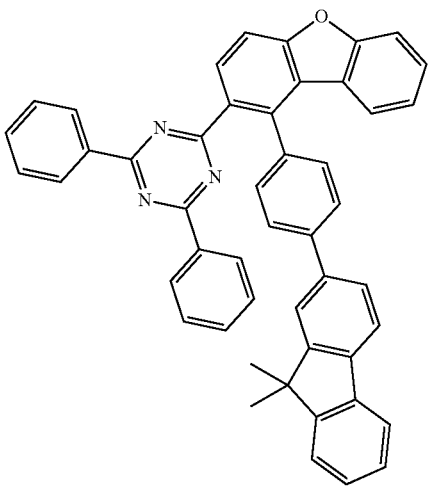
1-3-28
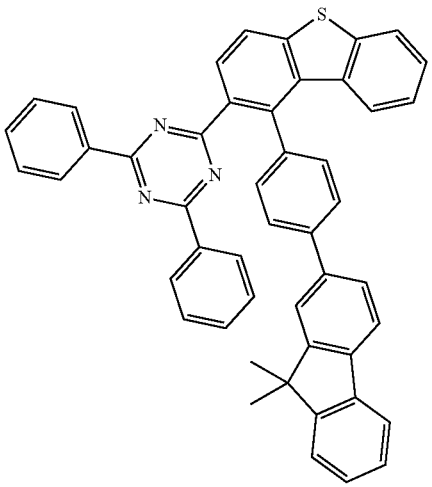
1-3-29
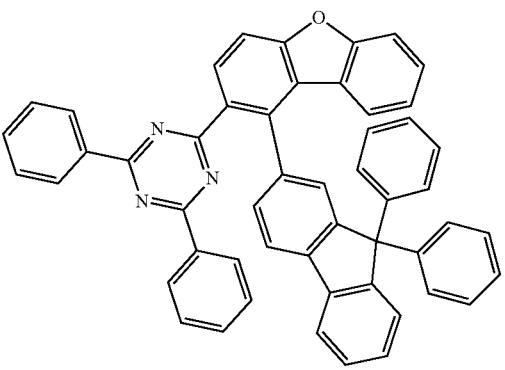

1-3-30
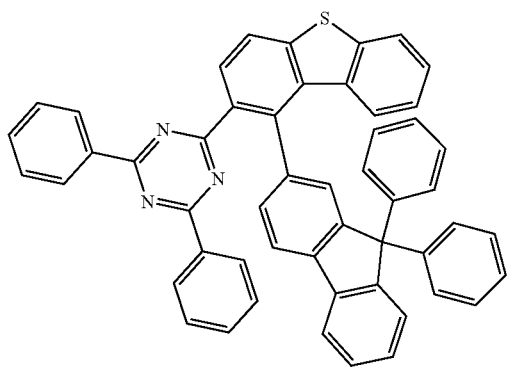
1-3-31
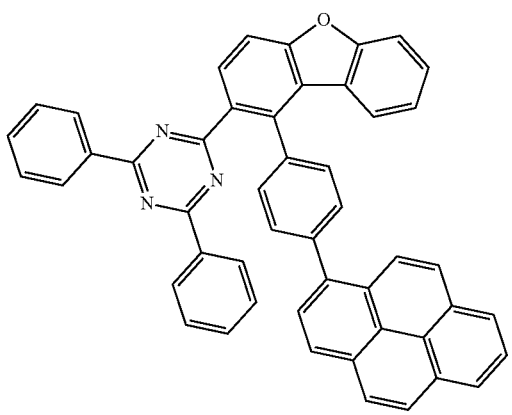
1-3-32
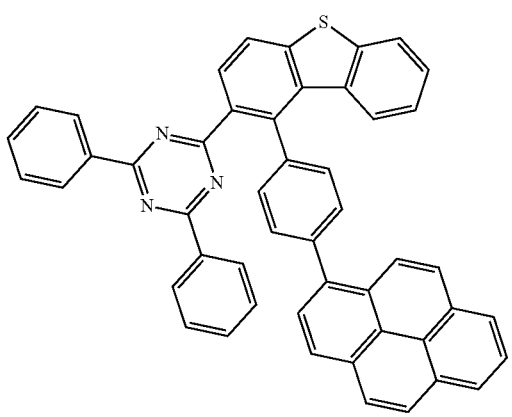
1-3-33
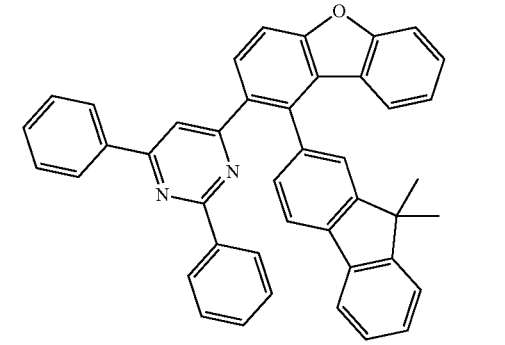
1-3-34
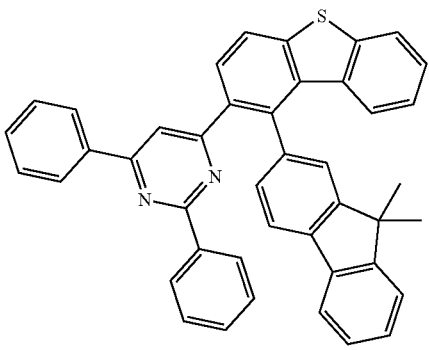
1-3-35
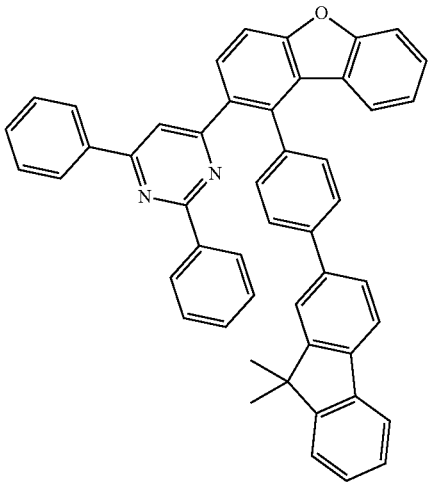
1-3-36
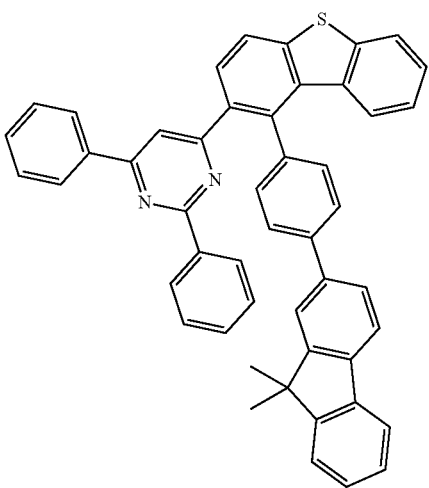

1-3-37
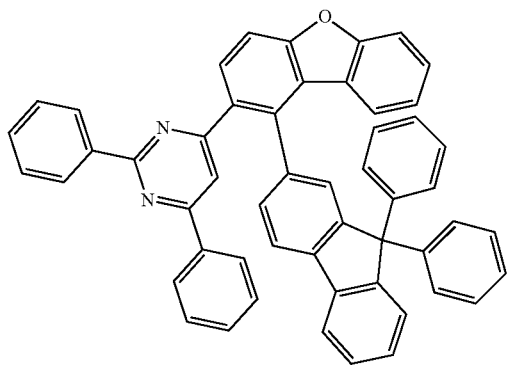
1-3-38
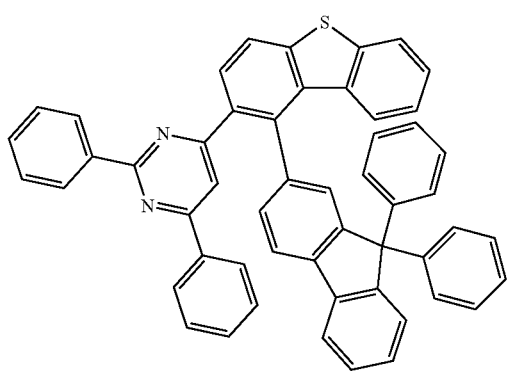
1-3-39
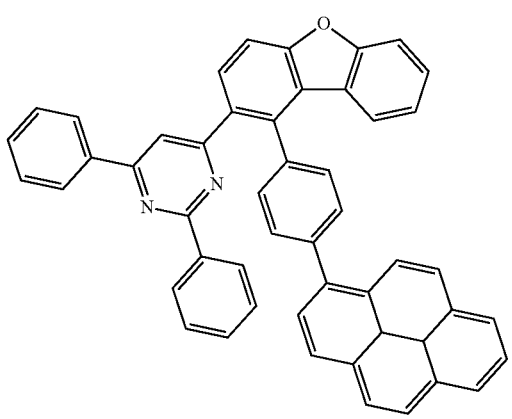
1-3-40
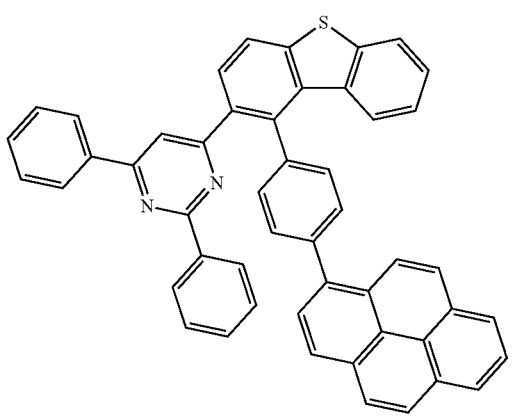
1-3-41
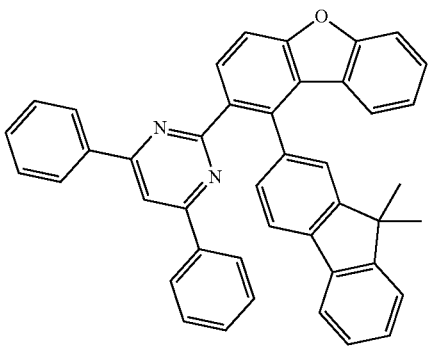
1-3-42
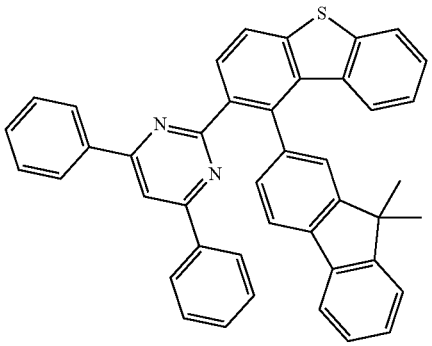
1-3-43
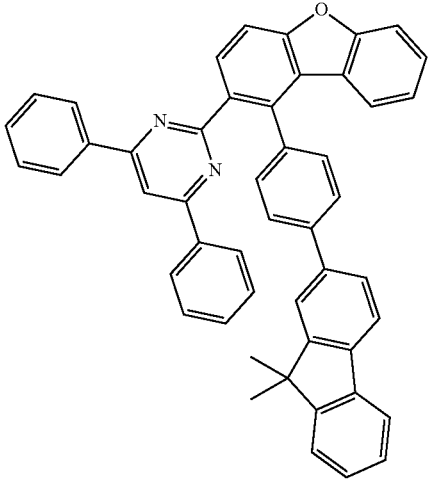

1-3-44
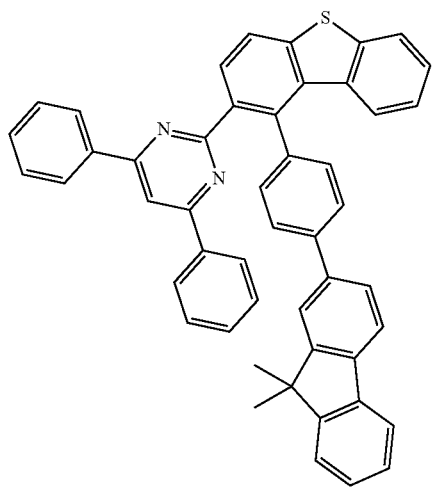
1-3-45
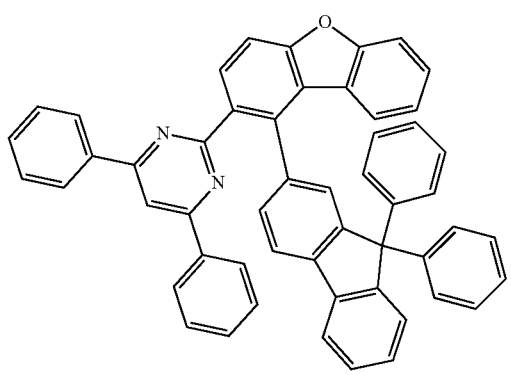
1-3-46
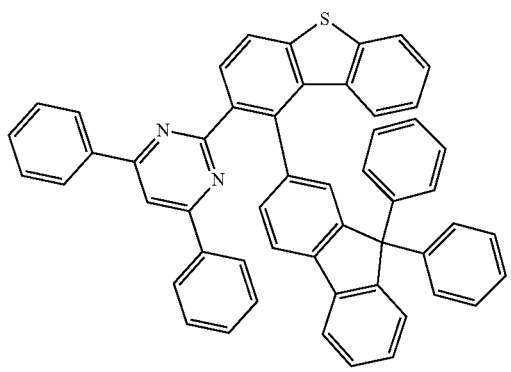
1-3-47
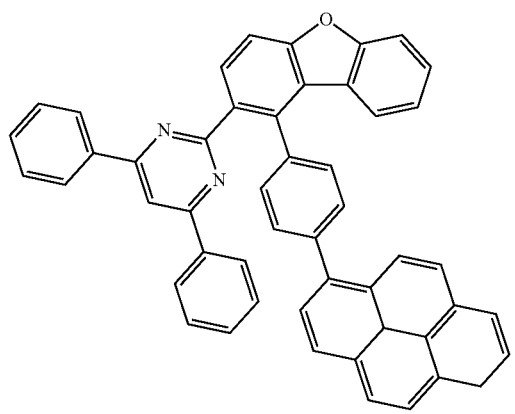
1-3-48
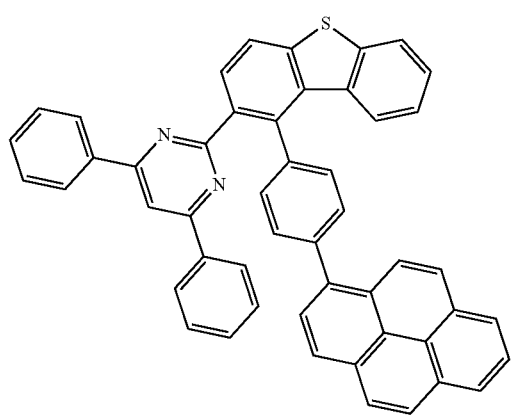
1-3-49
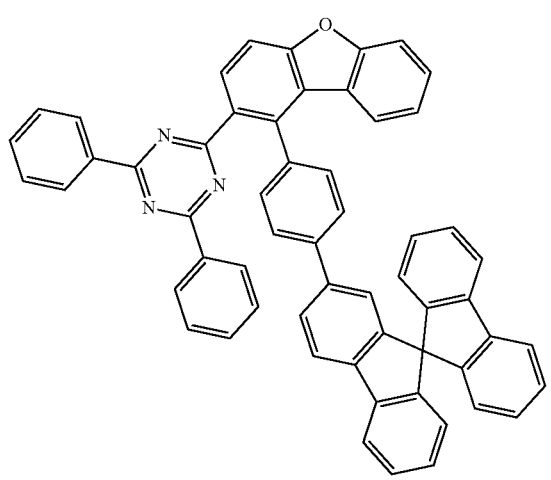

1-3-50
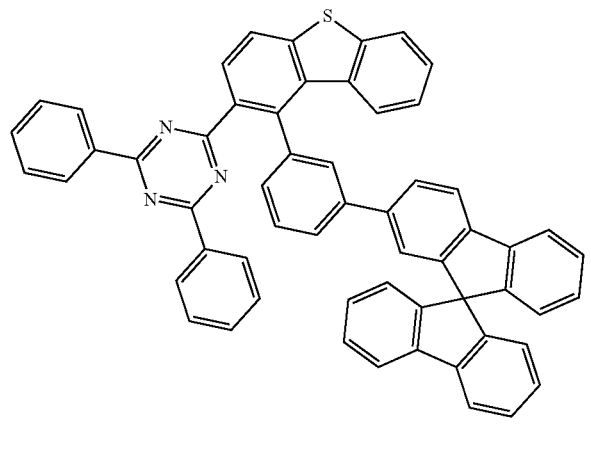
1-3-53
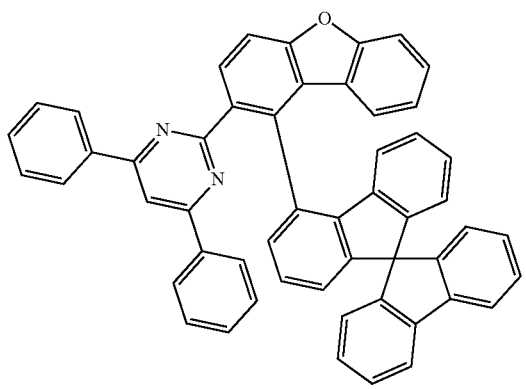
1-3-51
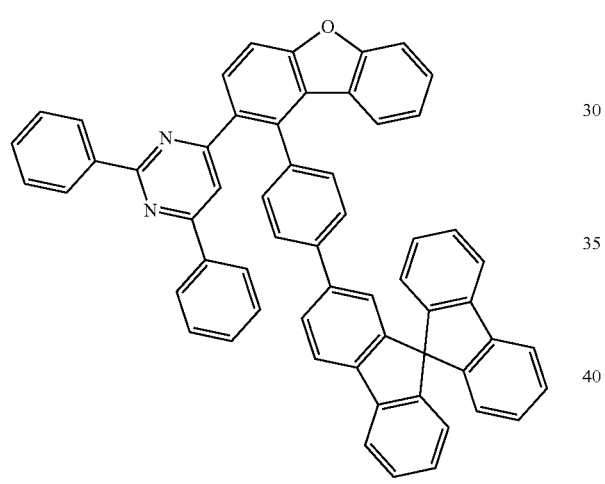
1-3-54
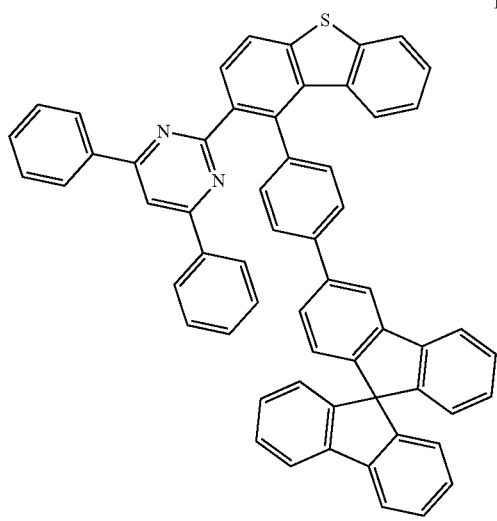
1-3-52
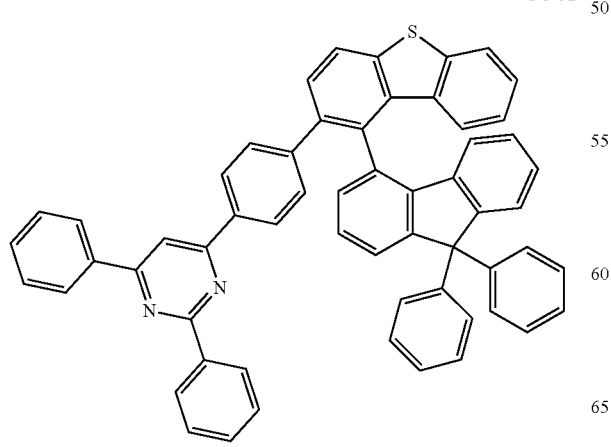
1-3-55
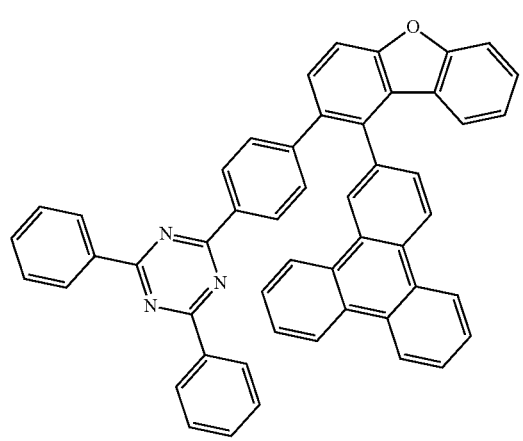

-continued
1-3-56
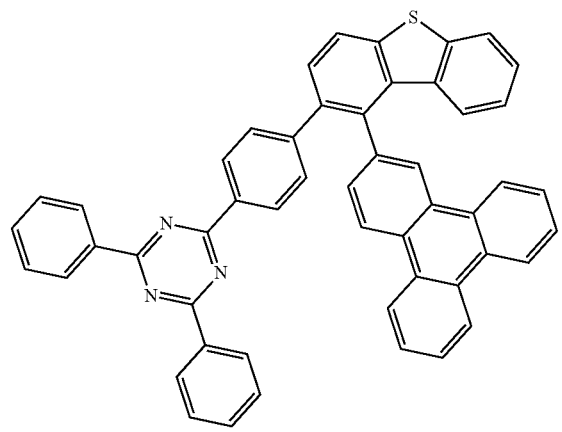
1-3-57
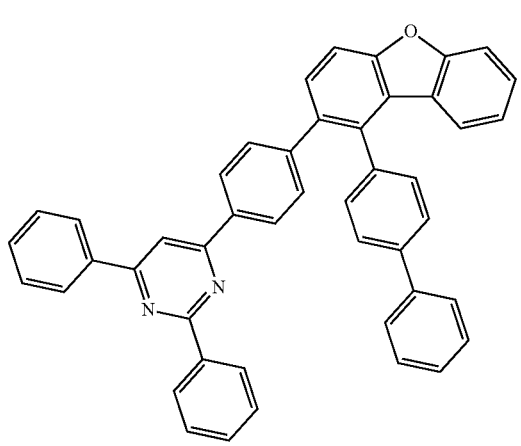
1-3-58
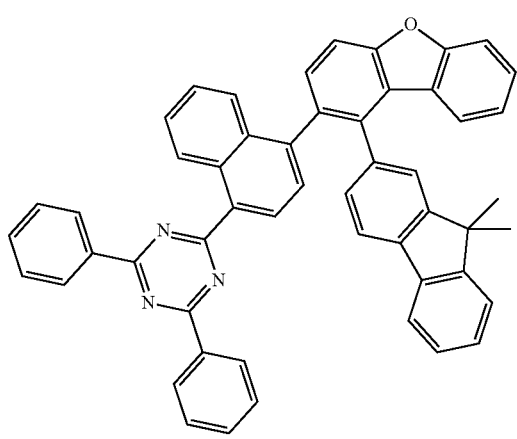
1-3-59
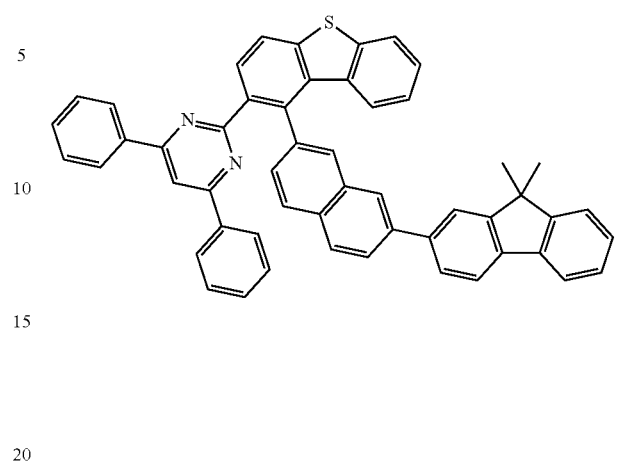
1-3-60
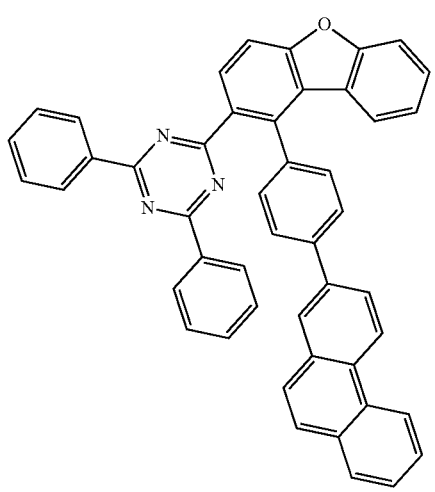
1-3-61
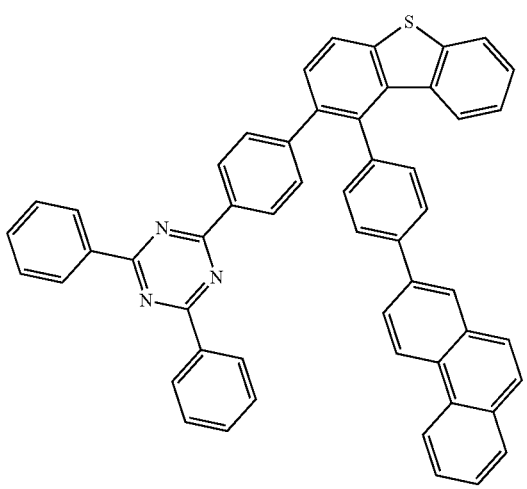

1-3-62
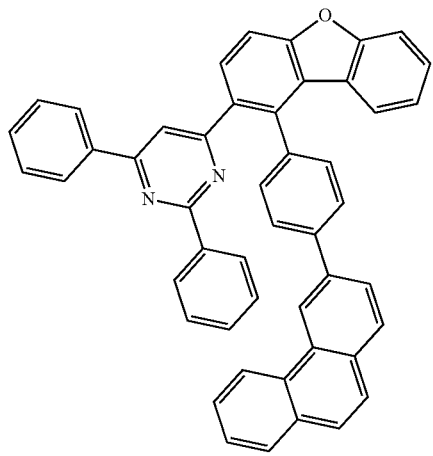
1-3-63
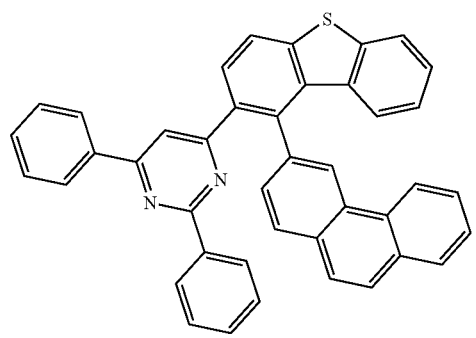
1-4-1
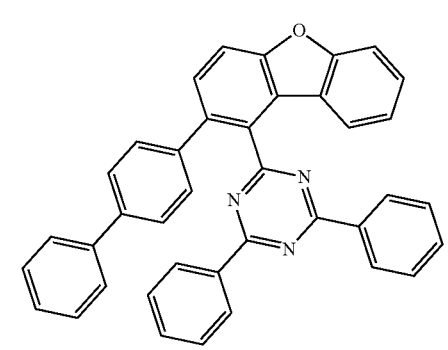
1-4-2
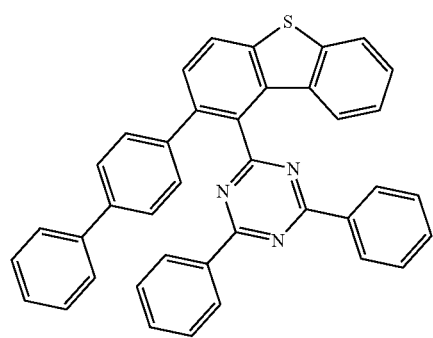
1-4-3
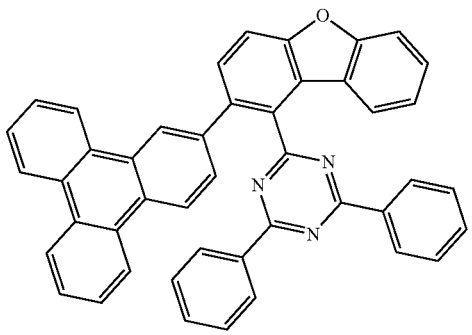
1-4-4
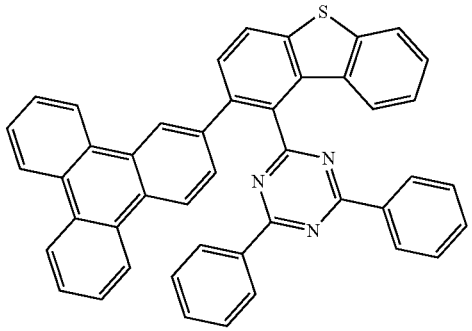
1-4-5
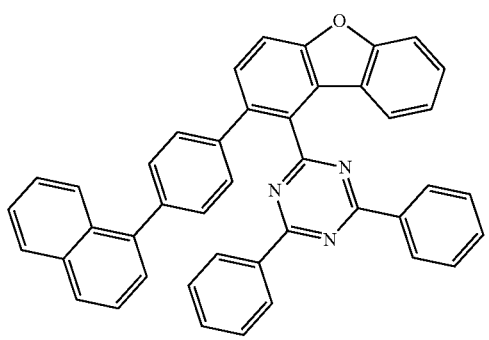
1-4-6
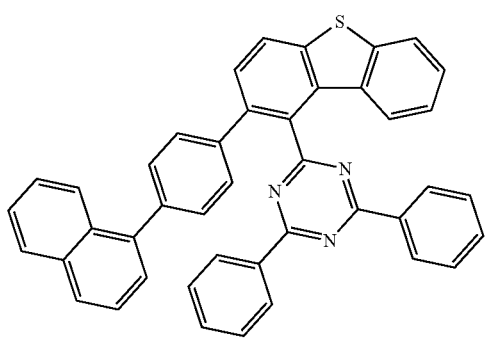

-continued
1-4-7
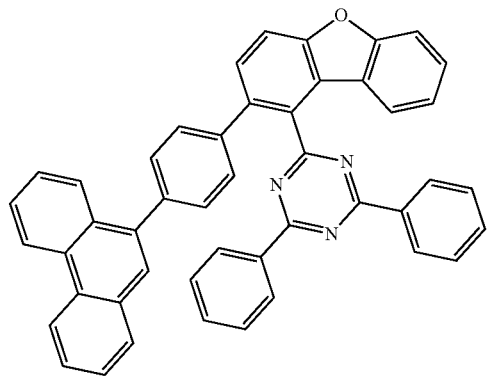
1-4-8
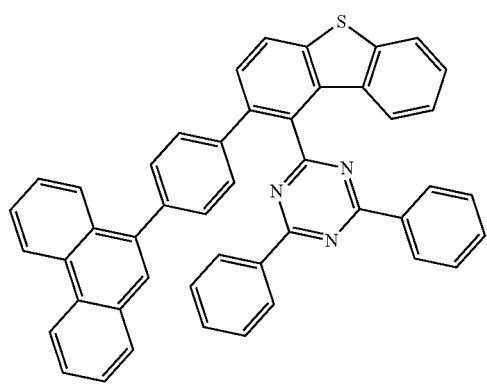
1-4-9
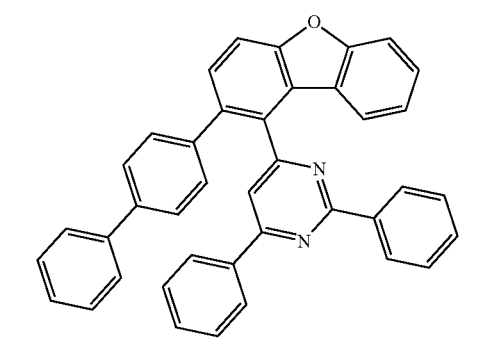
1-4-10
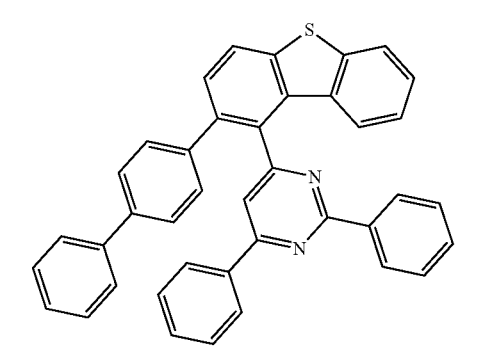
-continued
1-4-11
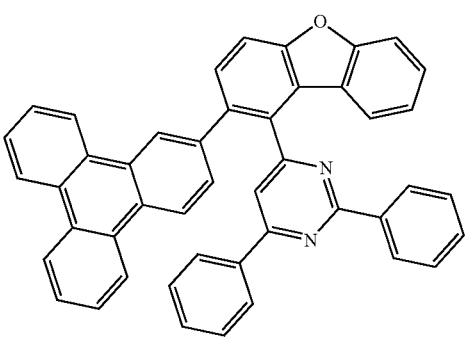
1-4-12
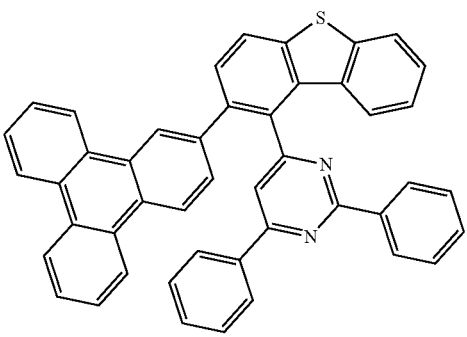
1-4-13
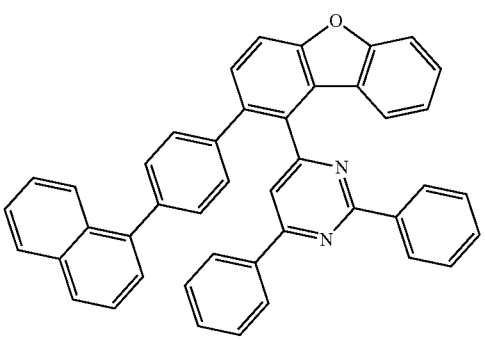
1-4-14
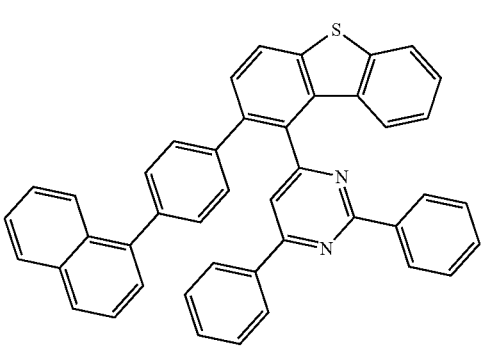

1-4-15
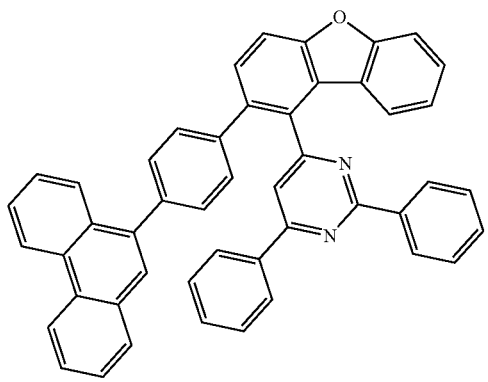
1-4-16
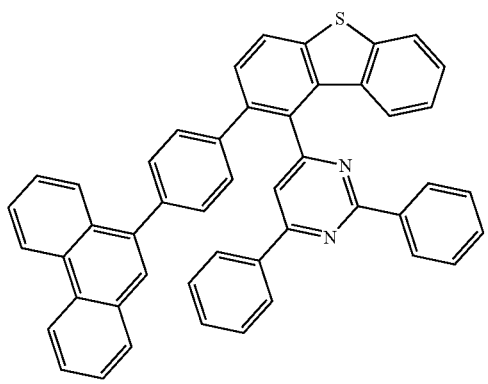
1-4-17
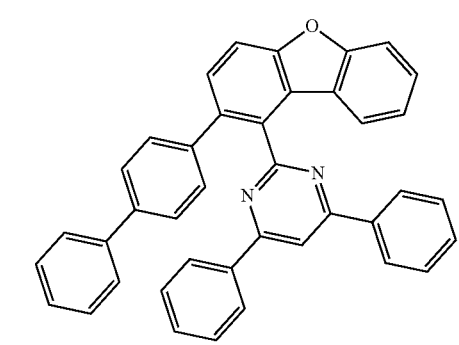
1-4-18
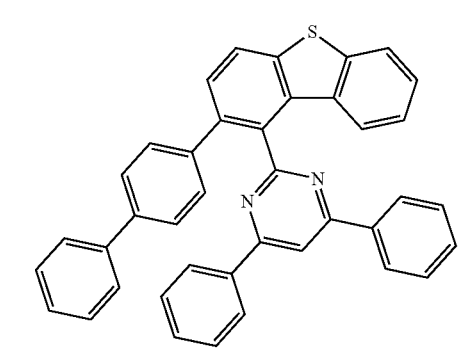
1-4-19
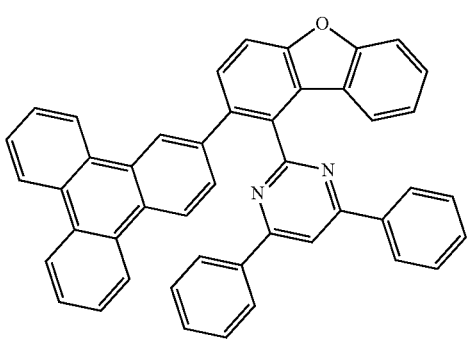
1-4-20
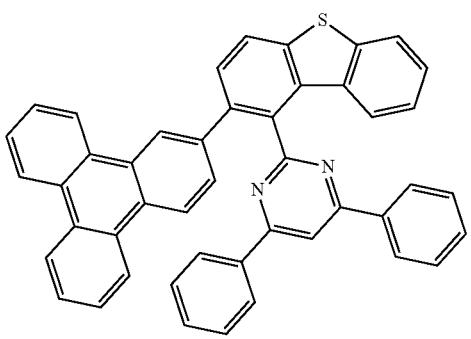
1-4-21
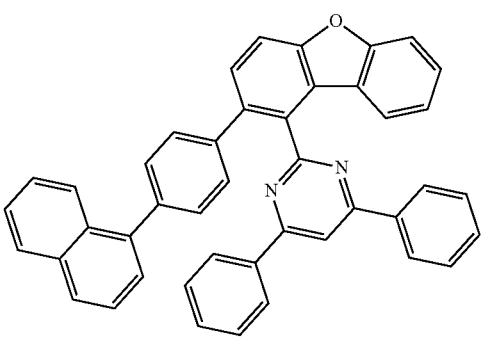
1-4-22
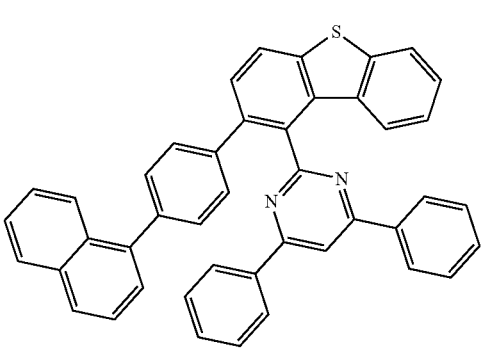

1-4-23
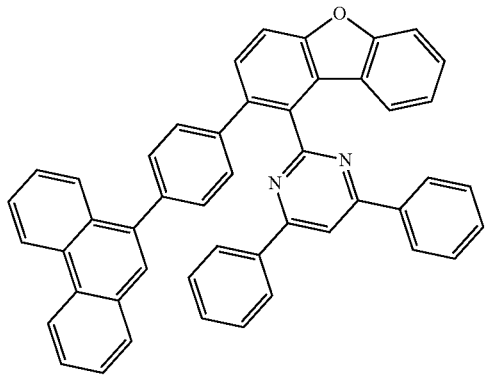
1-4-24
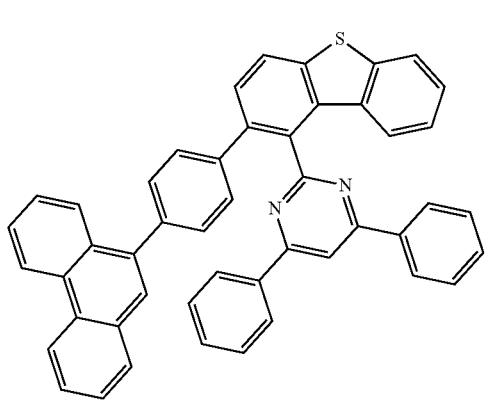
1-4-25
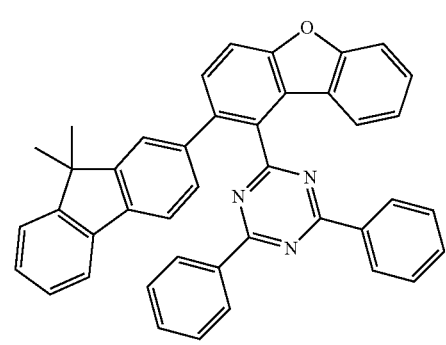
1-4-26
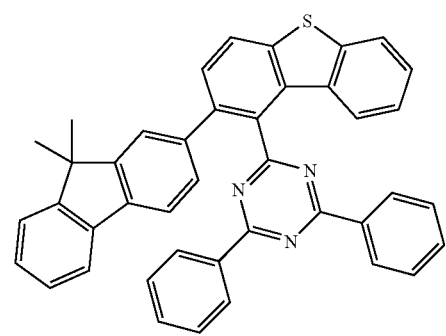
1-4-27
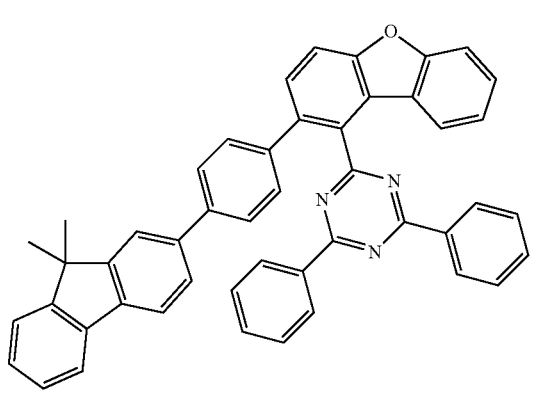
1-4-28
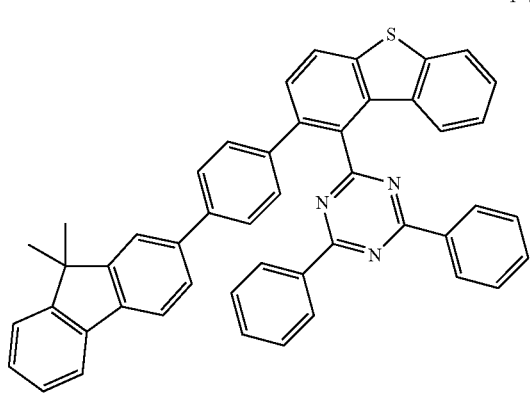
1-4-29
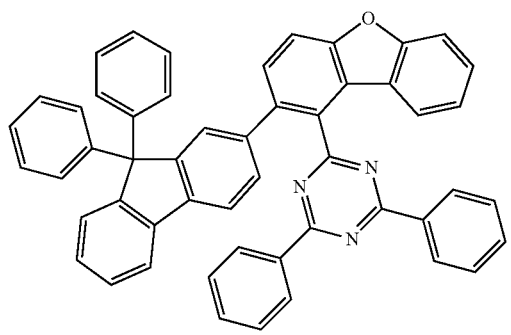
1-4-30
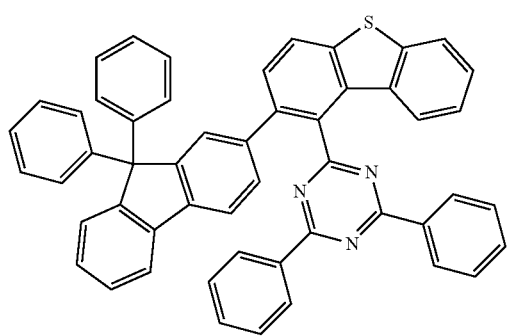

1-4-31
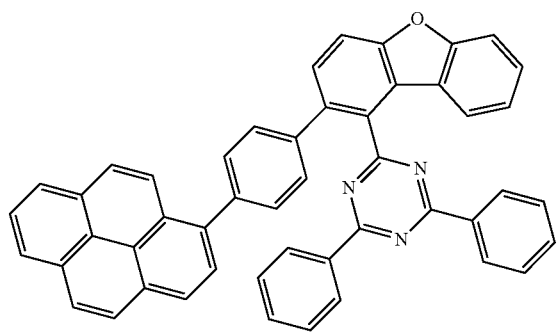
1-4-32
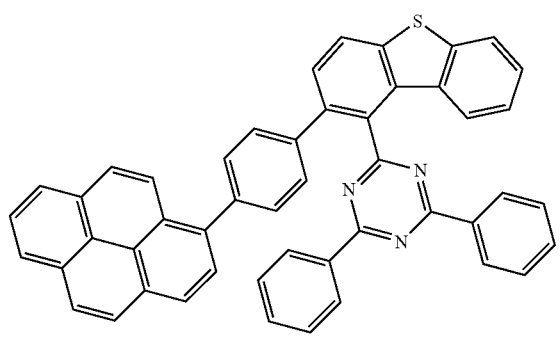
1-4-33
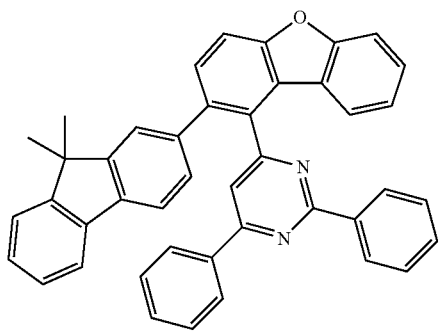
1-4-34
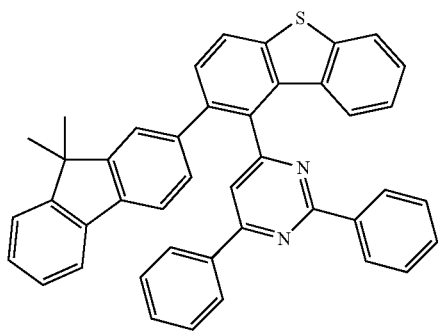
1-4-35
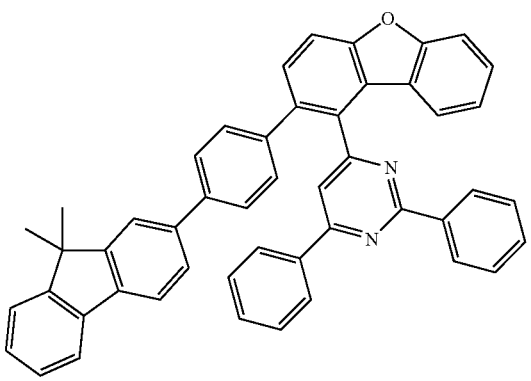
1-4-36
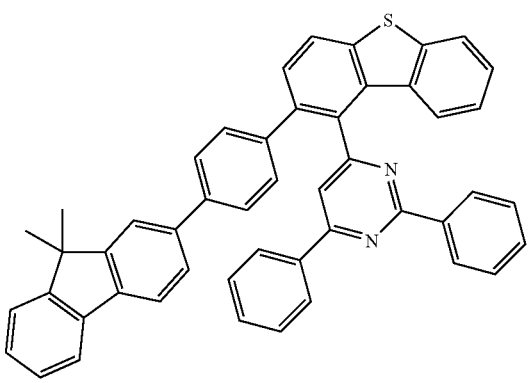
1-4-37
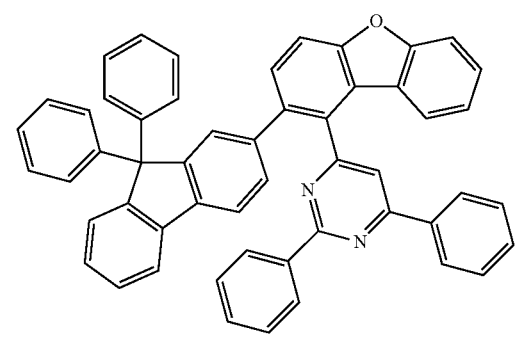
1-4-38
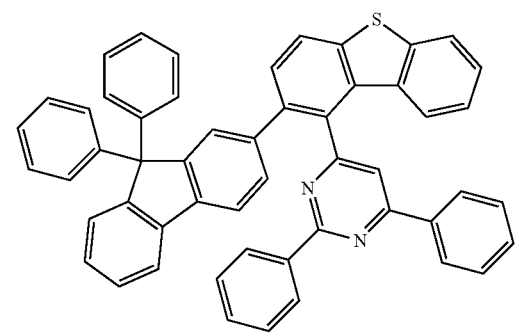

1-4-39
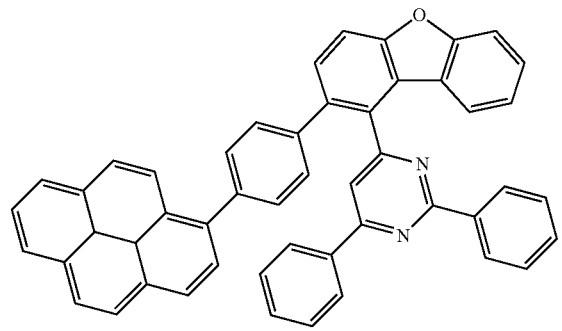
1-4-40
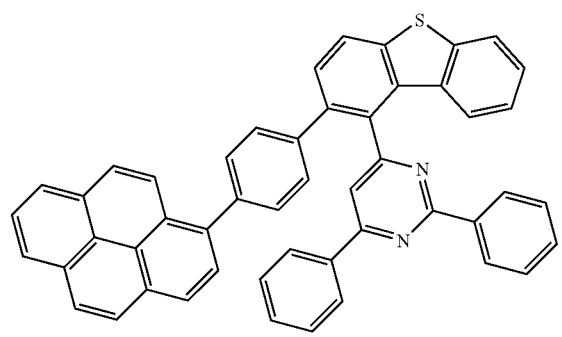
1-4-41
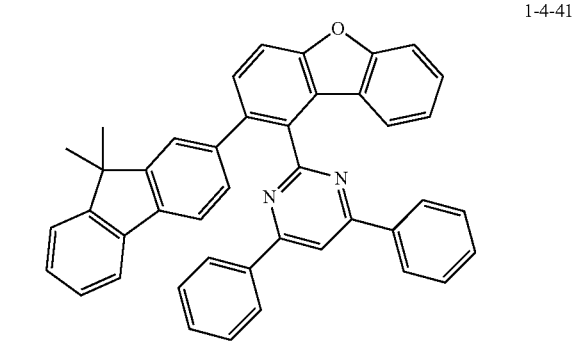
1-4-42
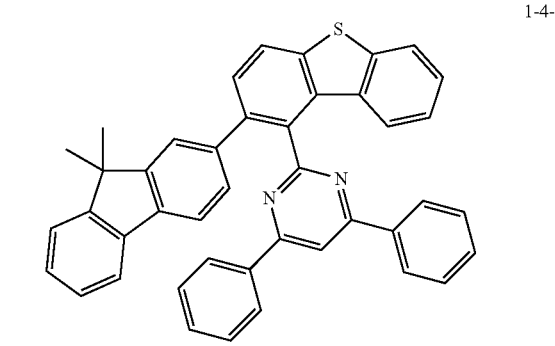
1-4-43
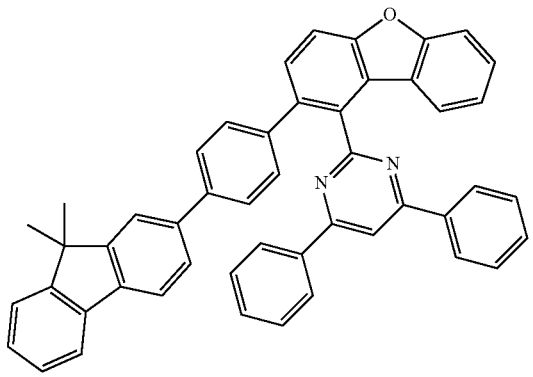
1-4-44
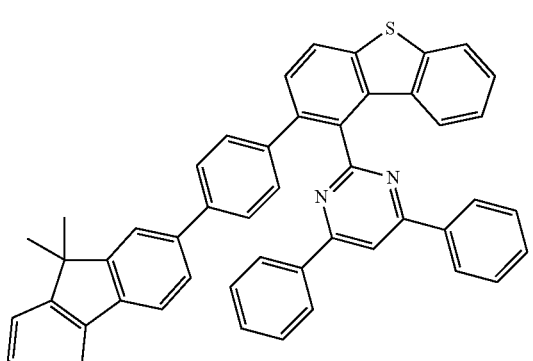
1-4-45
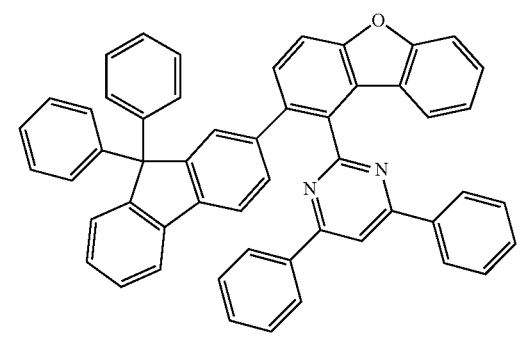
1-4-46
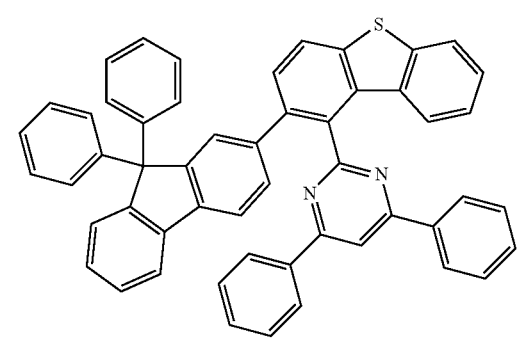

1-4-47
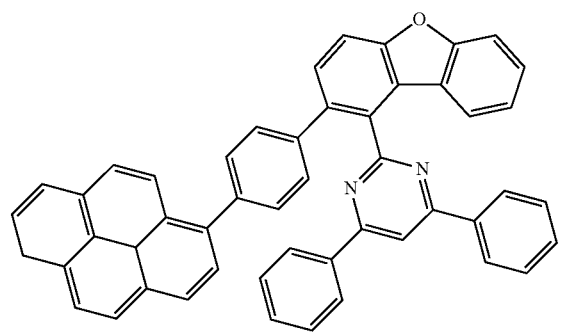
1-4-51
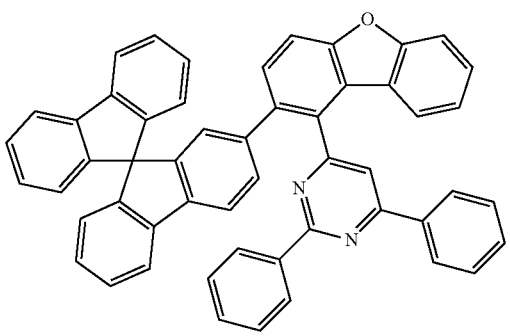
1-4-48
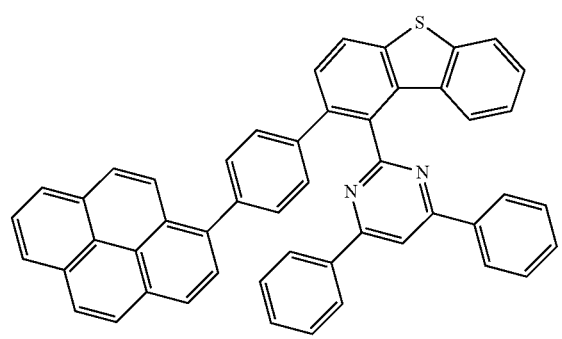
1-4-52
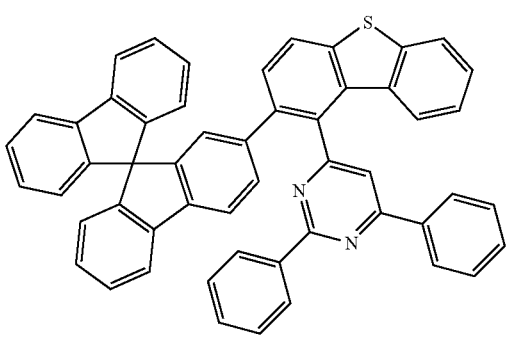
1-4-49
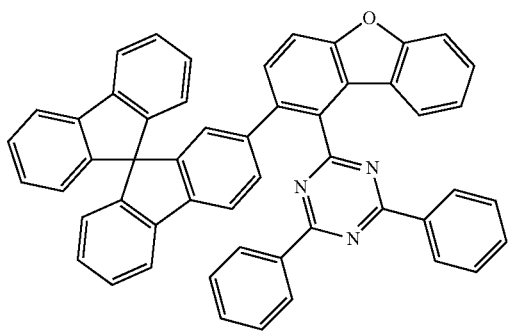
1-4-53
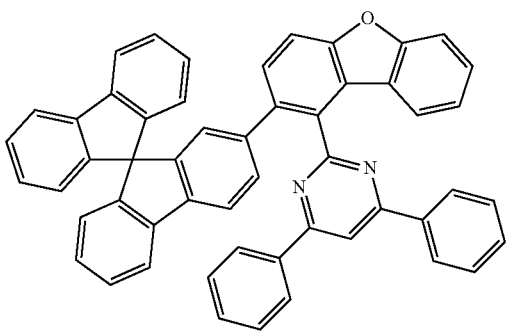
1-4-50
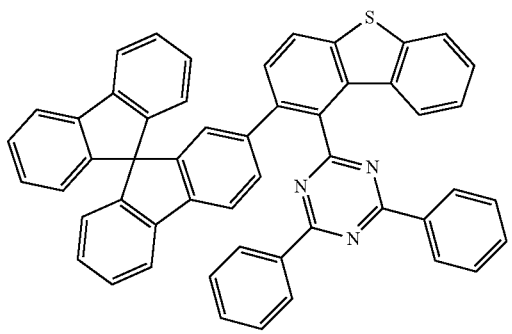
1-4-54
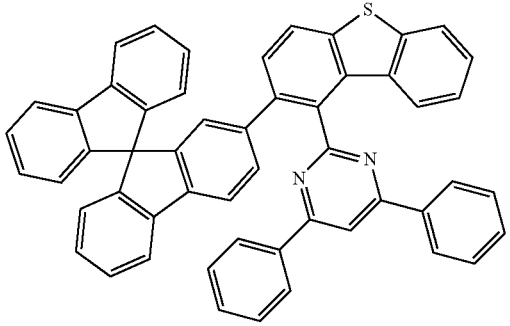

1-4-55
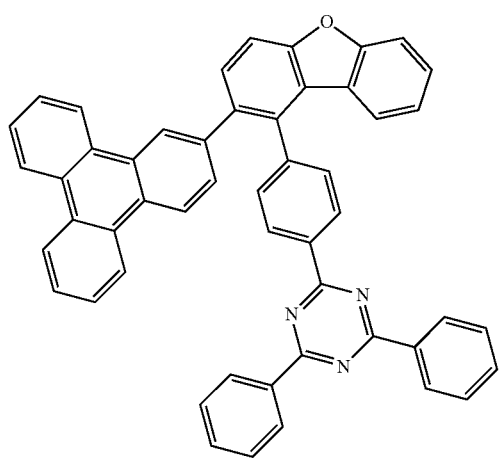
1-4-56
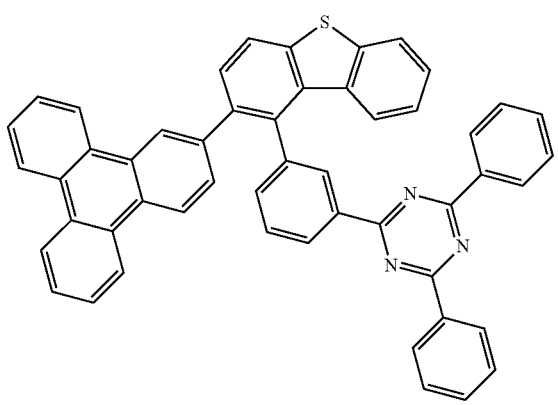
1-4-57
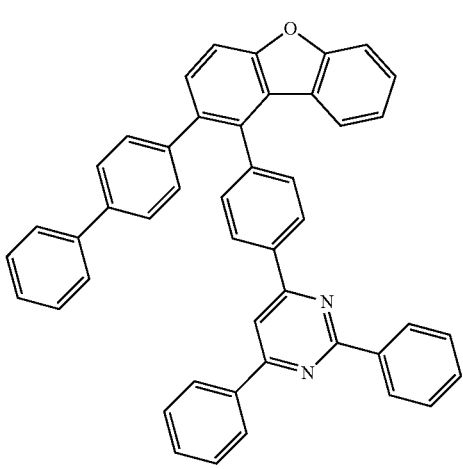
1-4-58
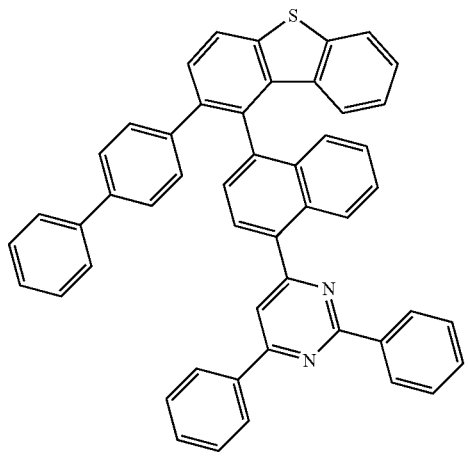
1-4-59
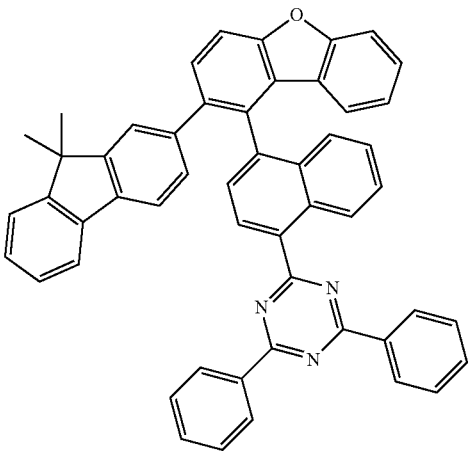
1-4-60
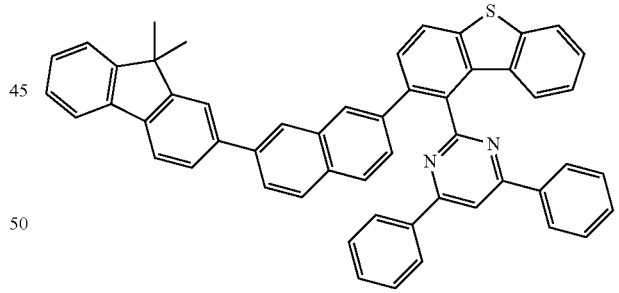
1-4-61
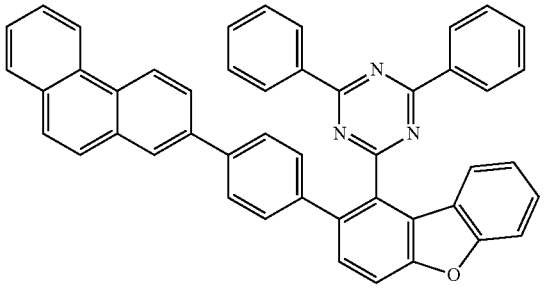

1-4-62
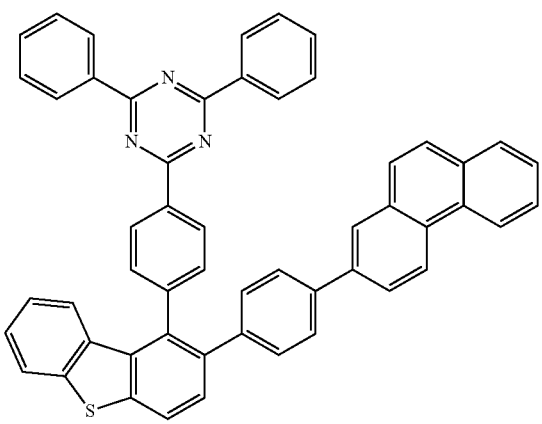
1-4-63
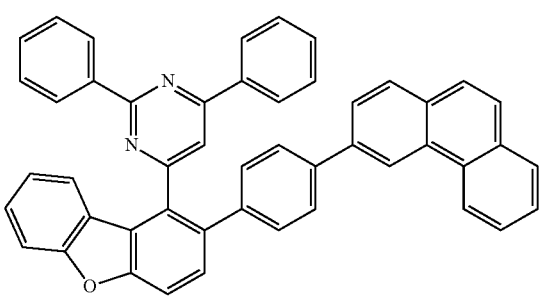
1-4-64
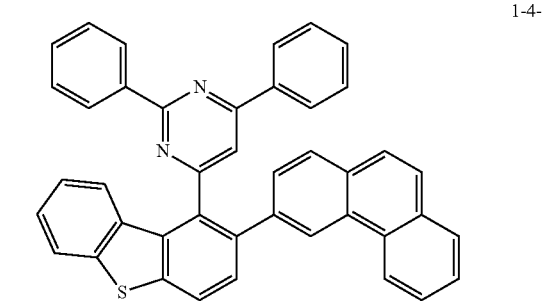
1-5-1
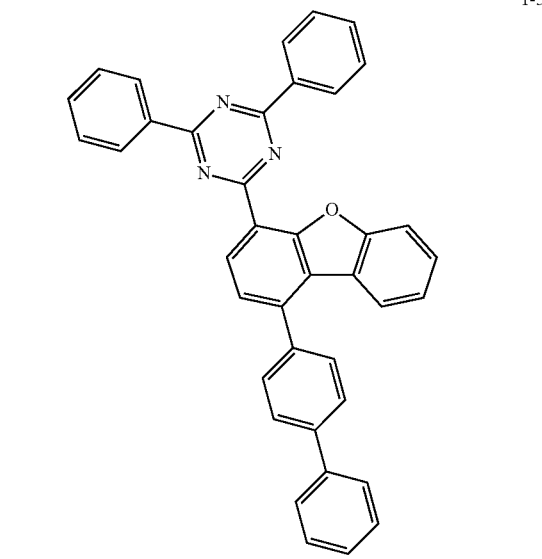
1-5-2
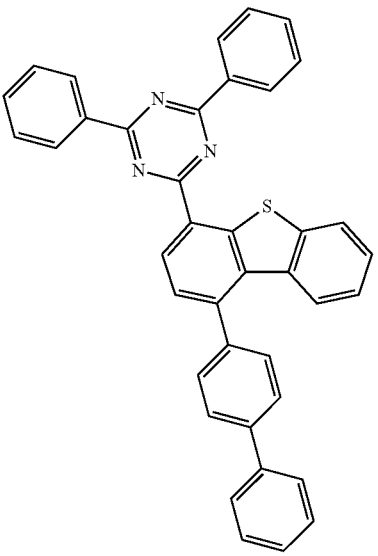
1-5-3
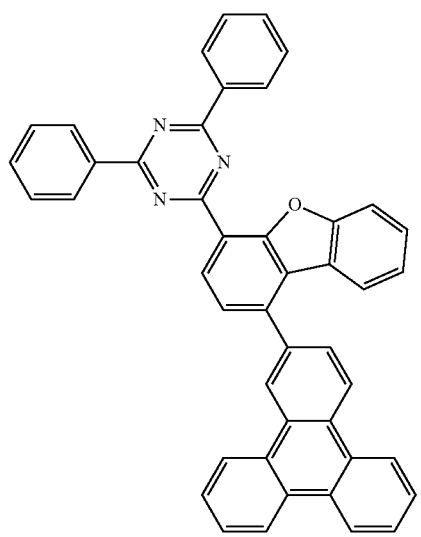
1-5-4
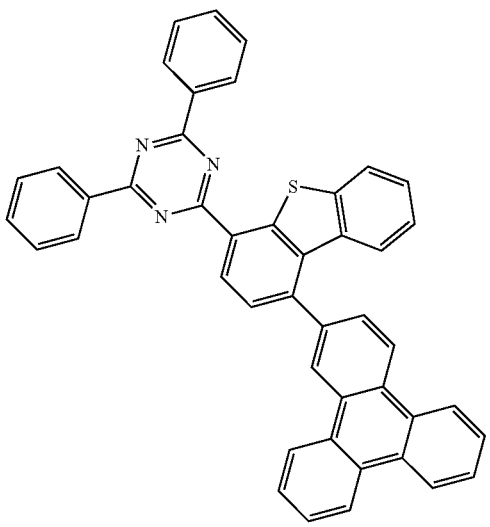

1-5-5
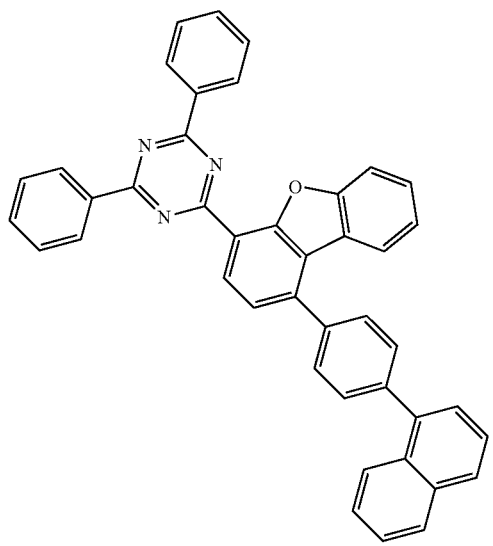
1-5-6
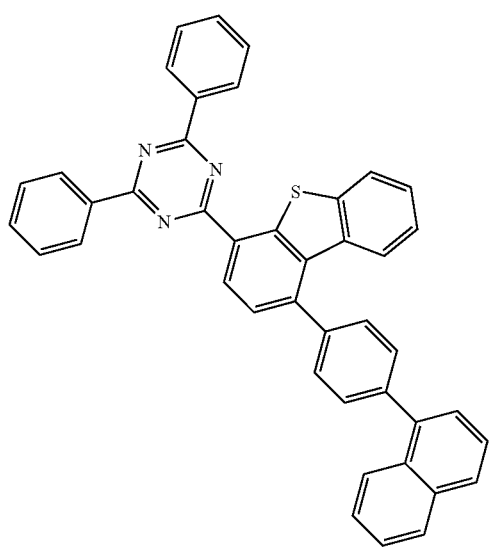
1-5-7
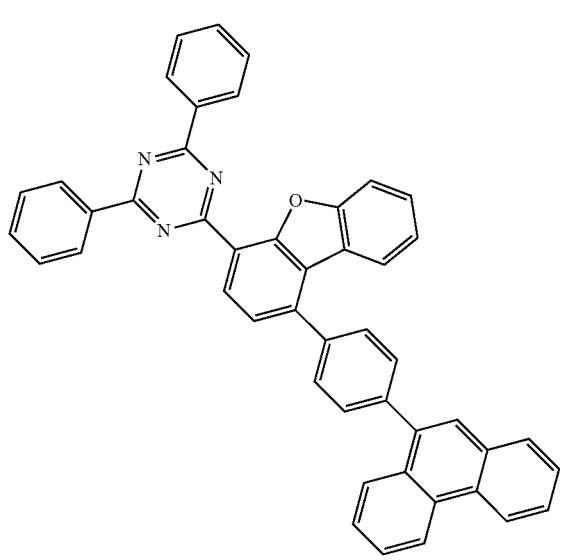
1-5-8
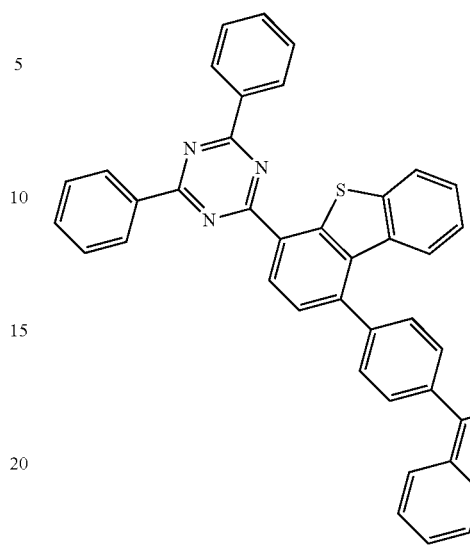
1-5-9
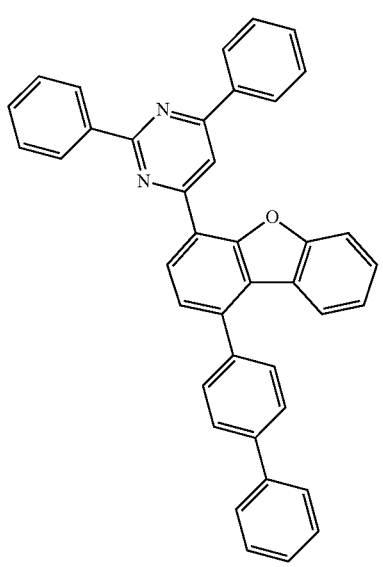
1-5-10
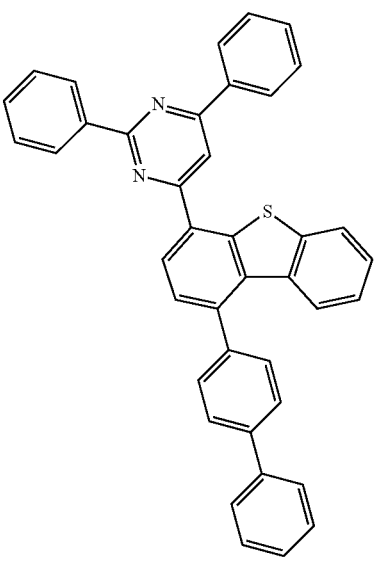

1-5-11
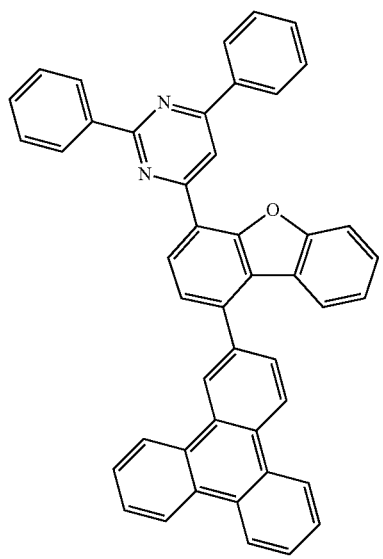
1-5-13
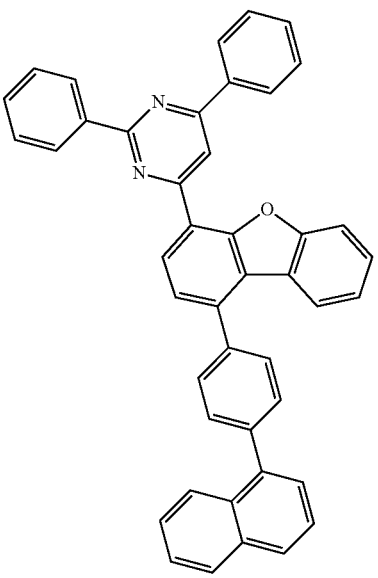
1-5-12
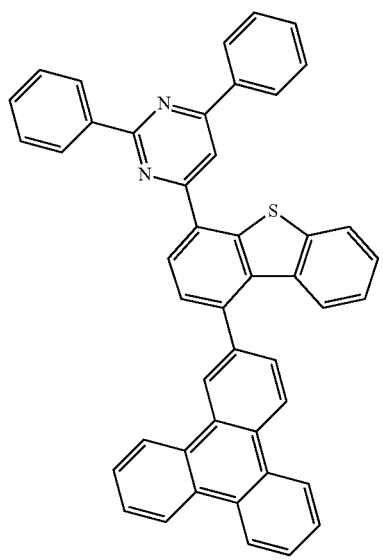
1-5-14
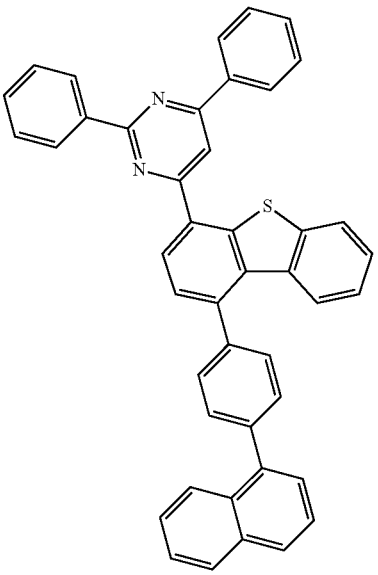

1-5-15
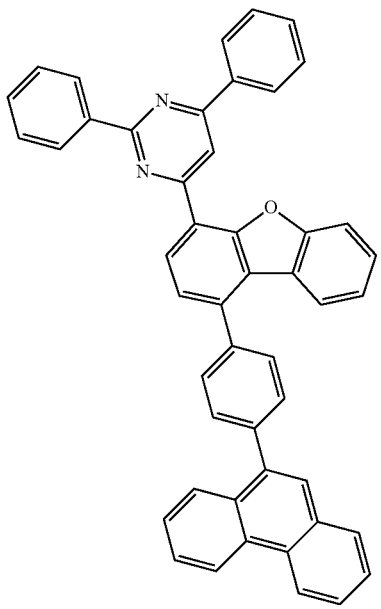
1-5-16
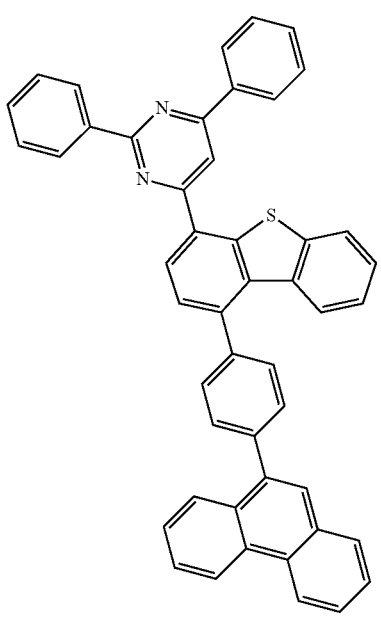
1-5-17
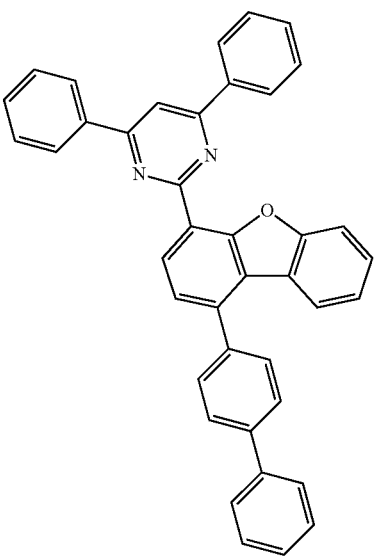
1-5-18
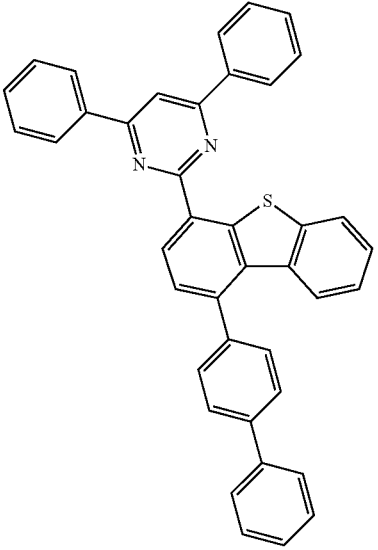
1-5-19

1-5-20
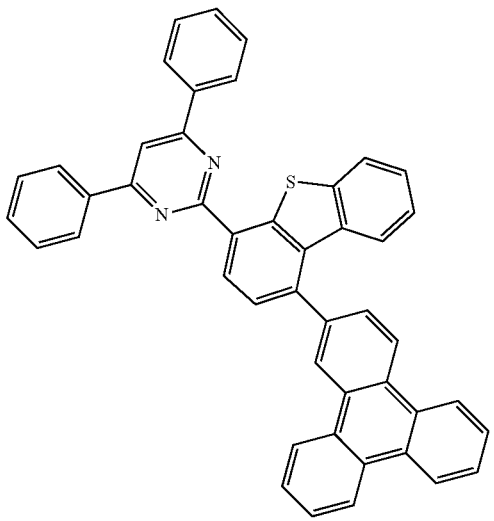
1-5-23
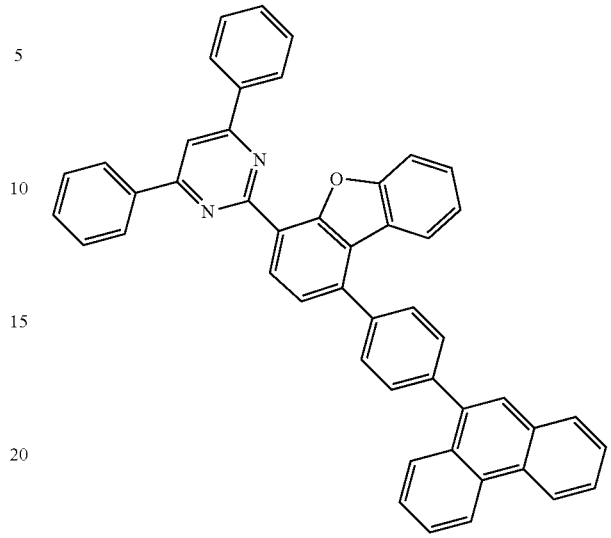
1-5-21
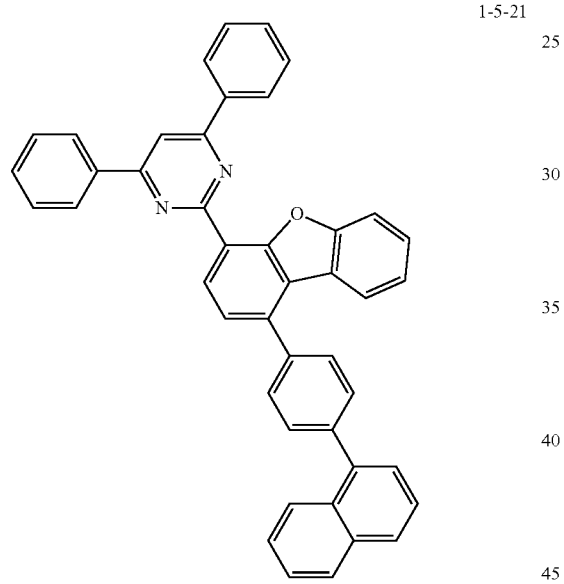
1-5-22
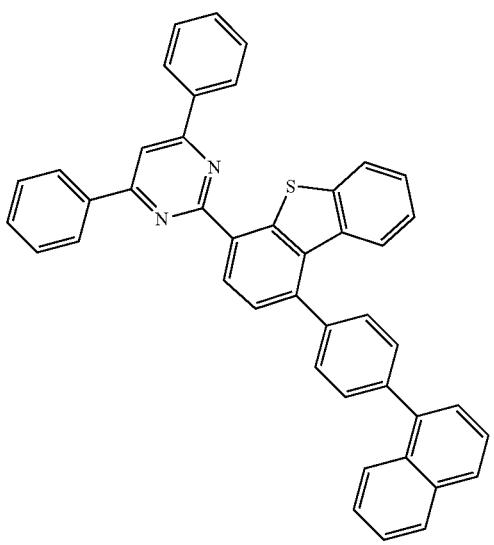
1-5-24
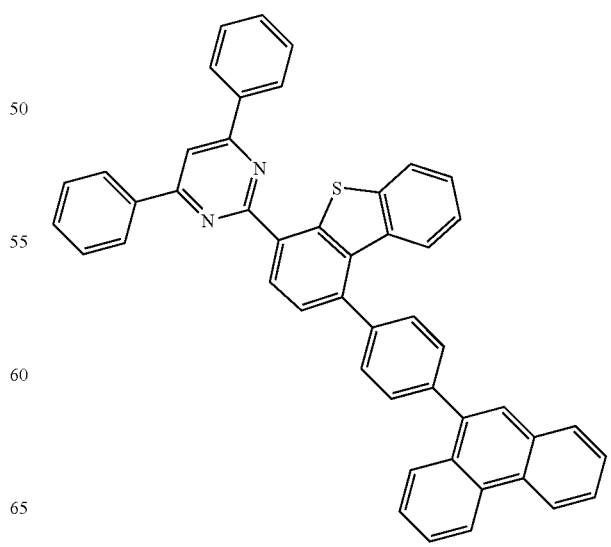

1-5-25
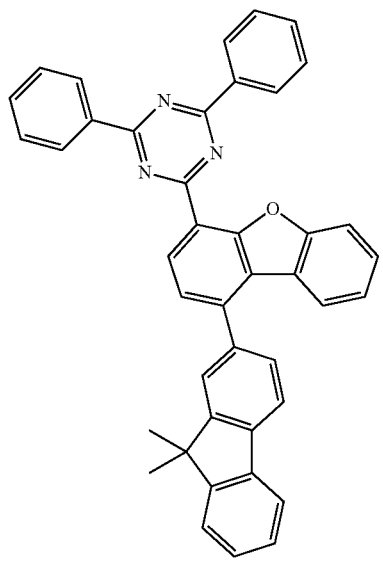
1-5-26
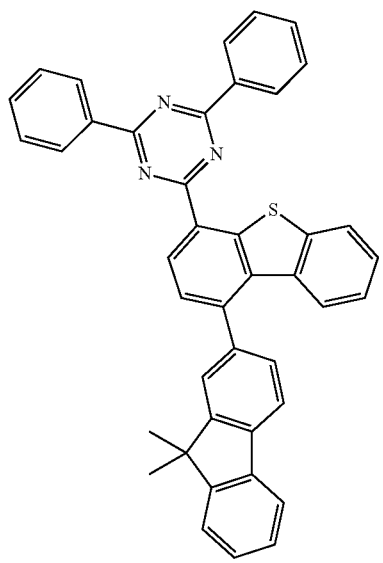
1-5-27
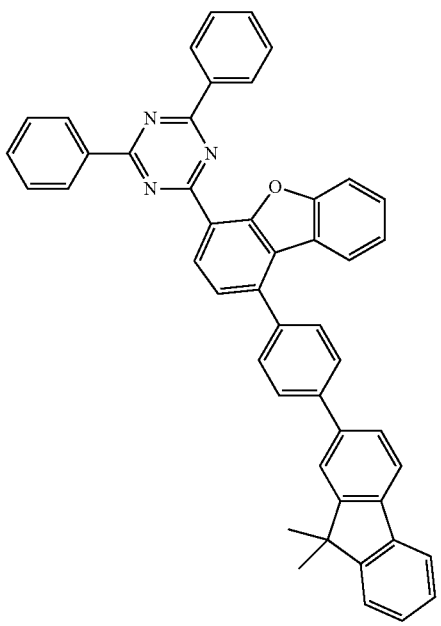
1-5-28
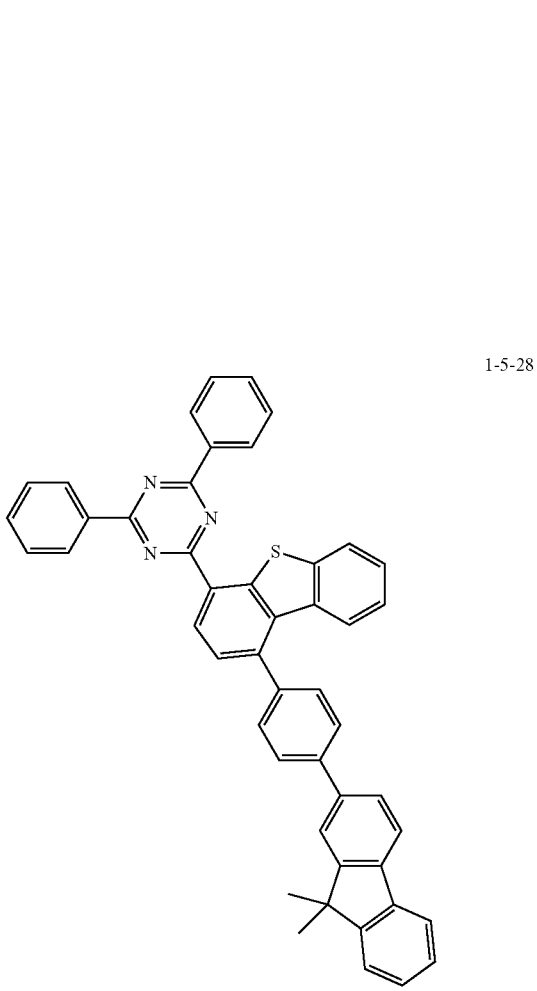

-continued
1-5-29
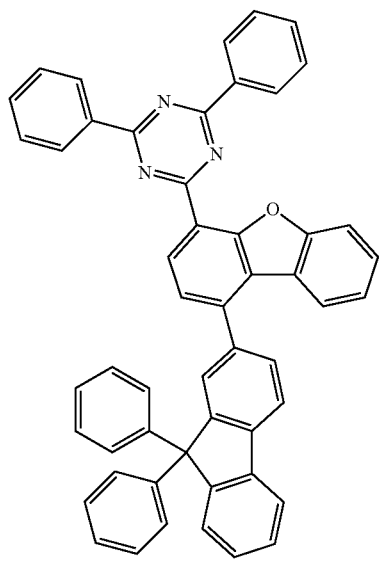
1-5-30
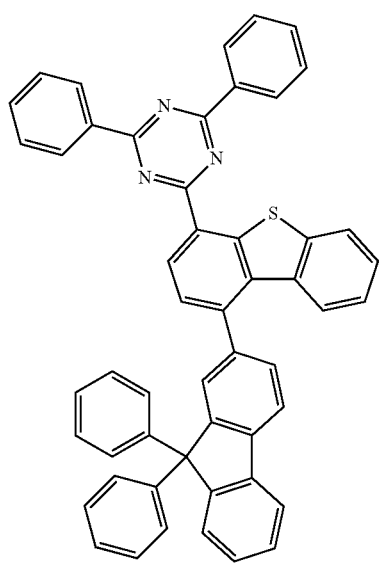
1-5-31
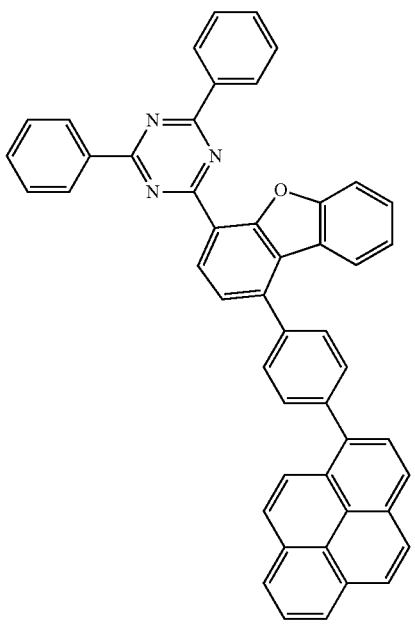
1-5-32
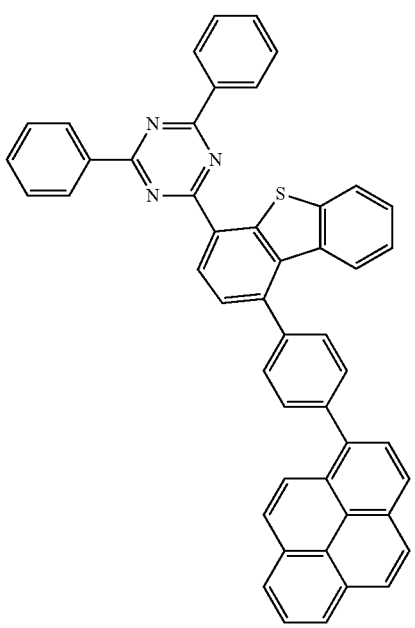

1-5-33
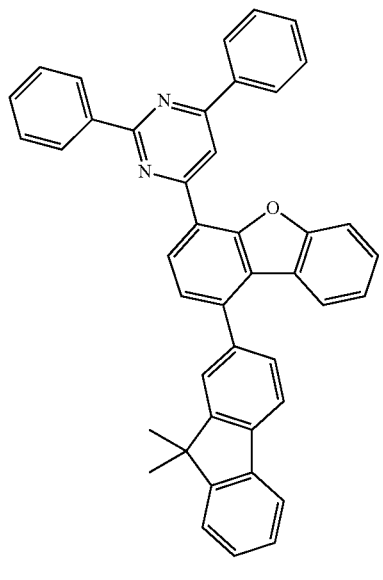
1-5-35
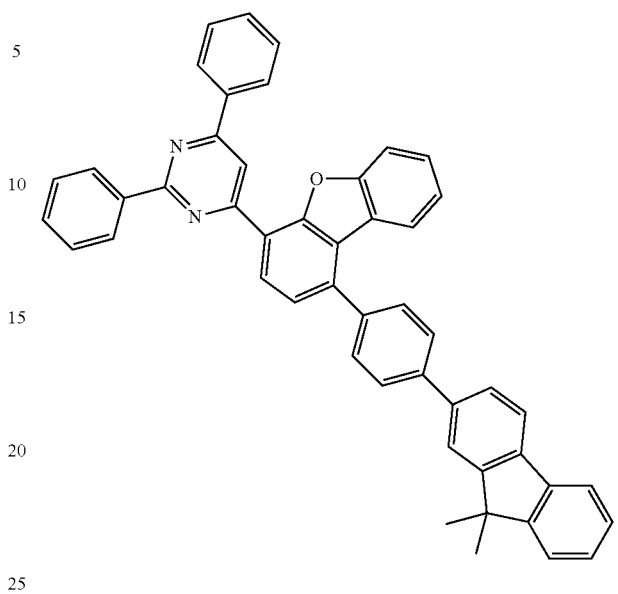
1-5-34
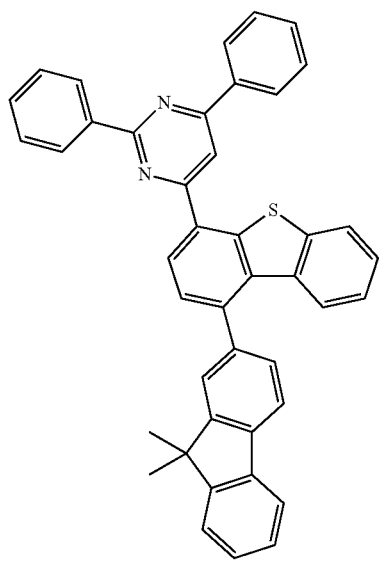
1-5-36
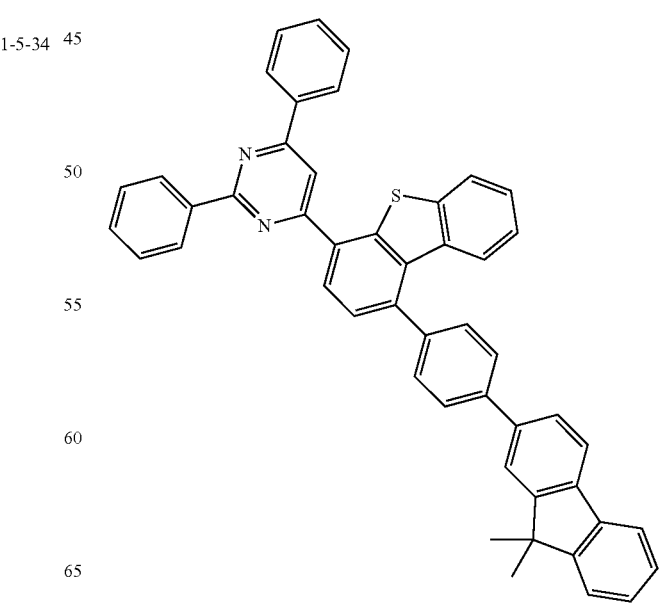

1-5-37
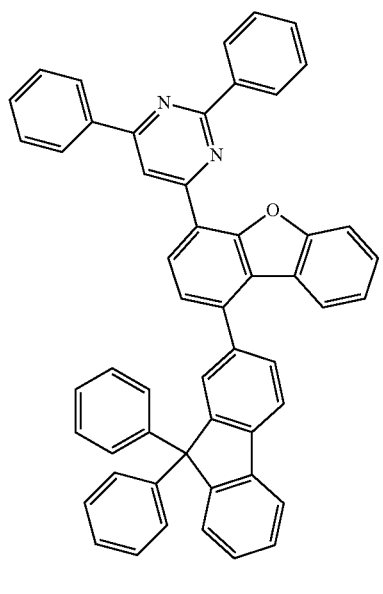
1-5-39
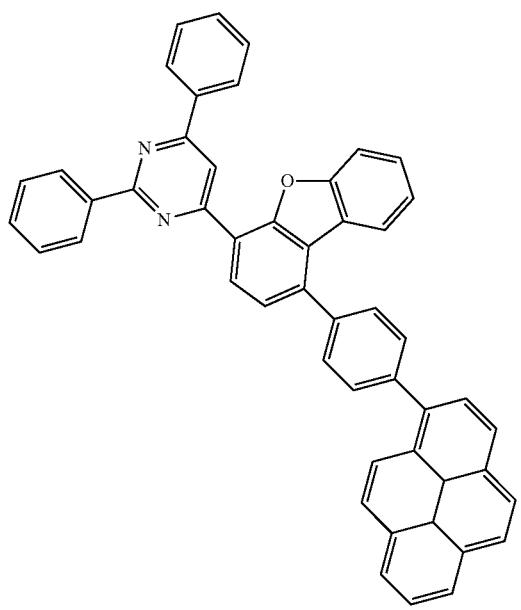
1-5-38
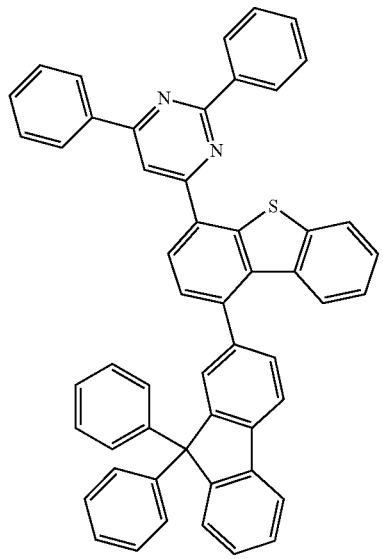
1-5-40
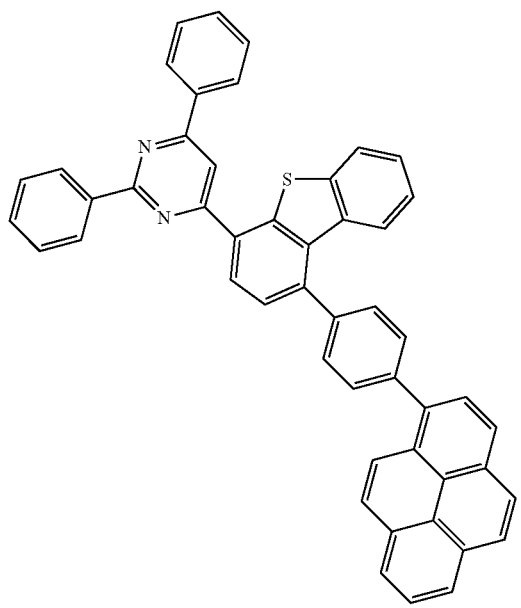

1-5-41
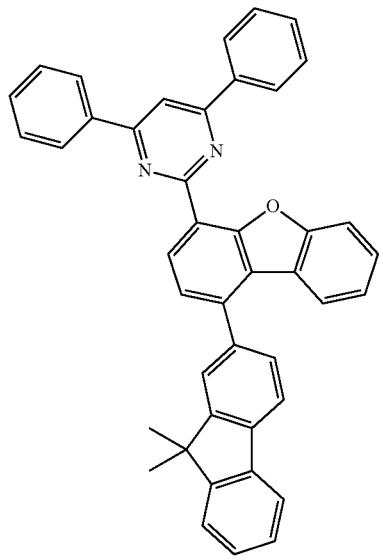
1-5-42
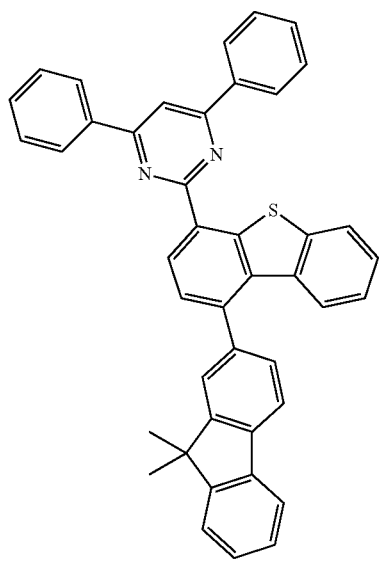
1-5-43
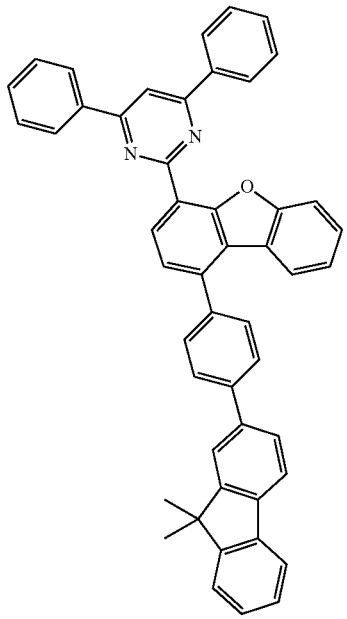
1-5-44
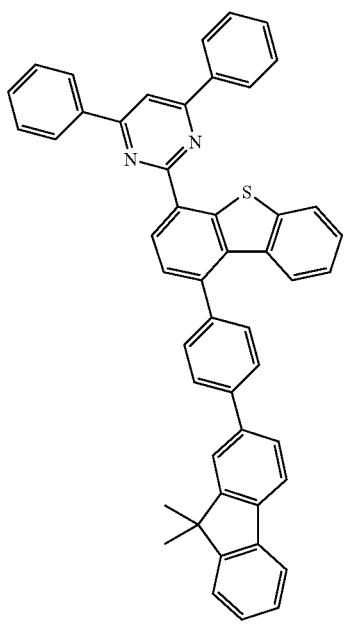

1-5-45
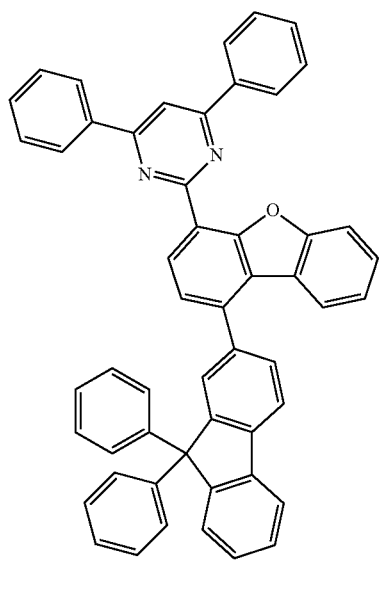
1-5-46
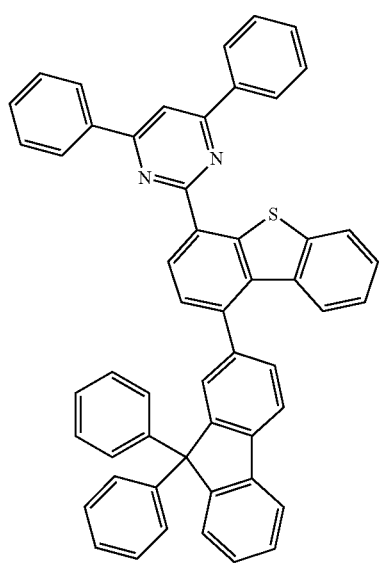
1-5-47
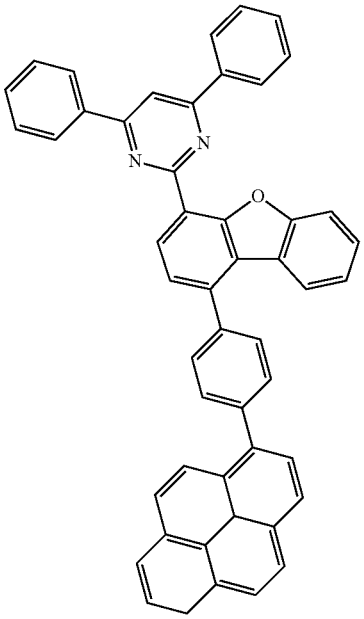
1-5-48
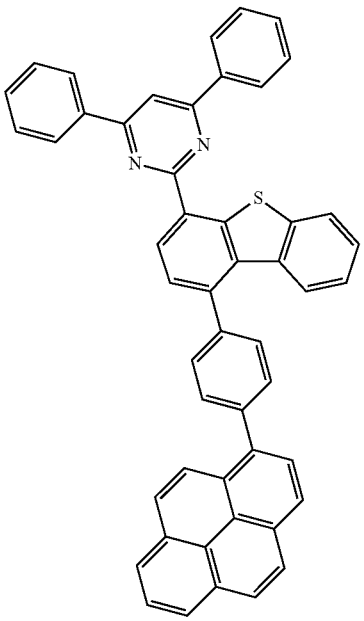

1-5-49
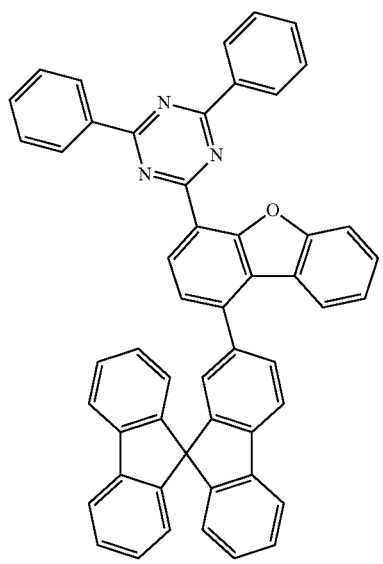
1-5-51
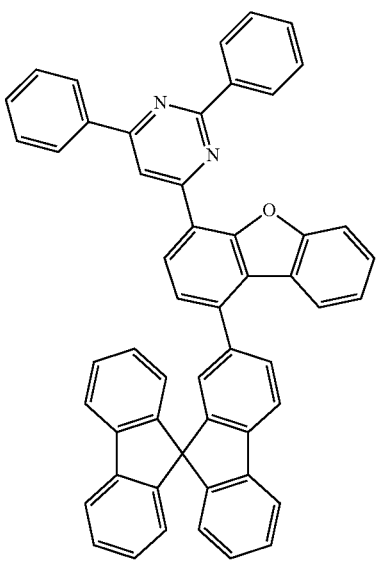
1-5-50
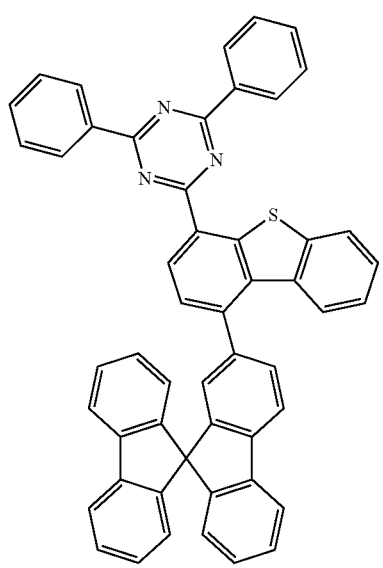
1-5-52
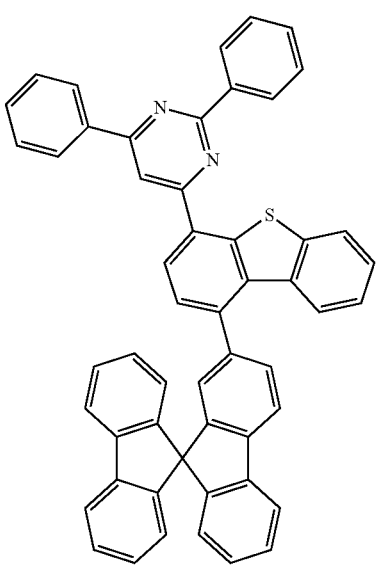

1-5-53
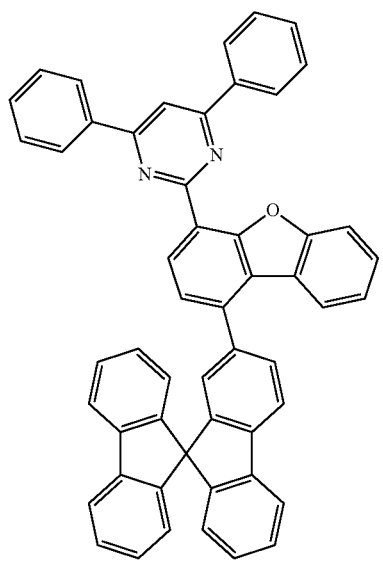
1-5-54
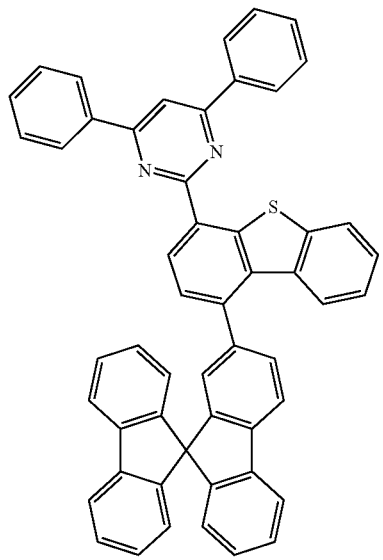
1-5-55
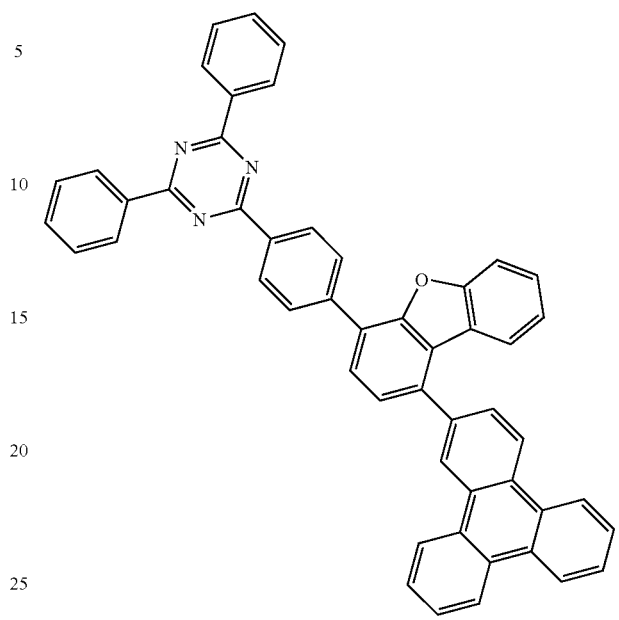
1-5-56
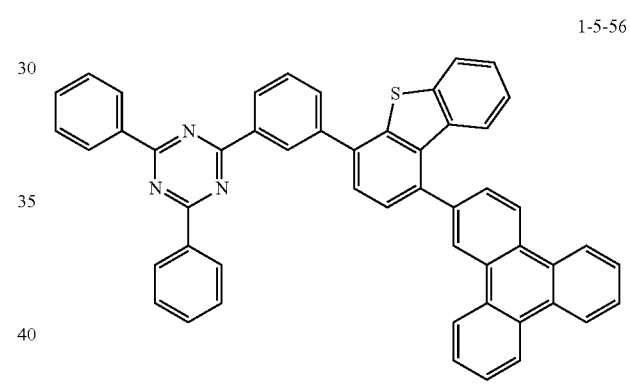
1-5-57
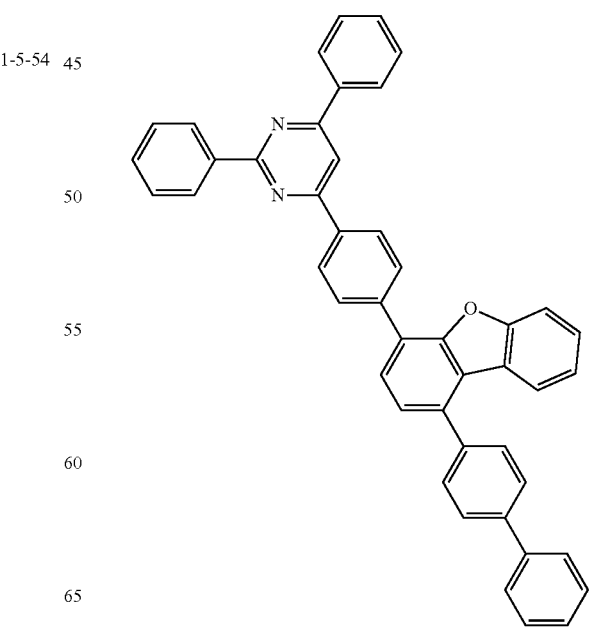

1-5-58
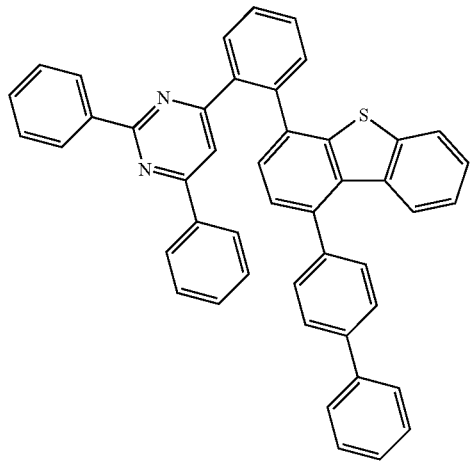
1-5-59
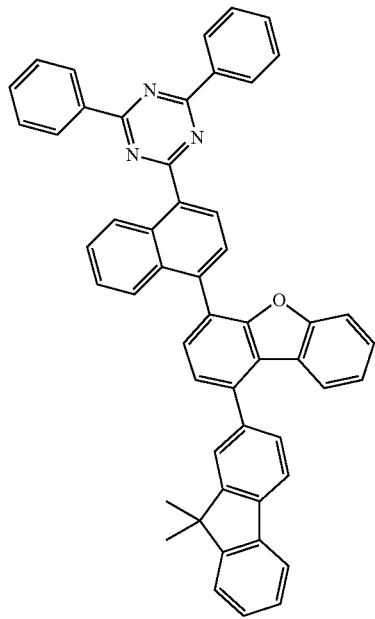
1-5-60
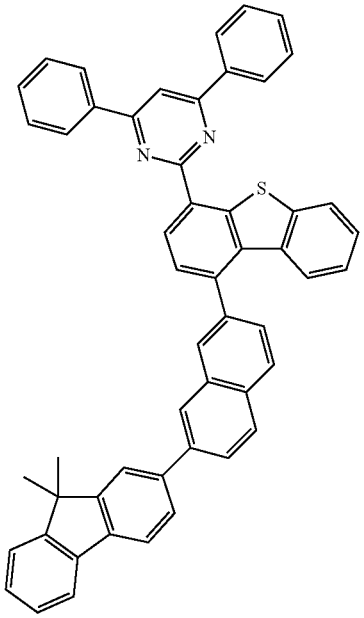
1-5-61
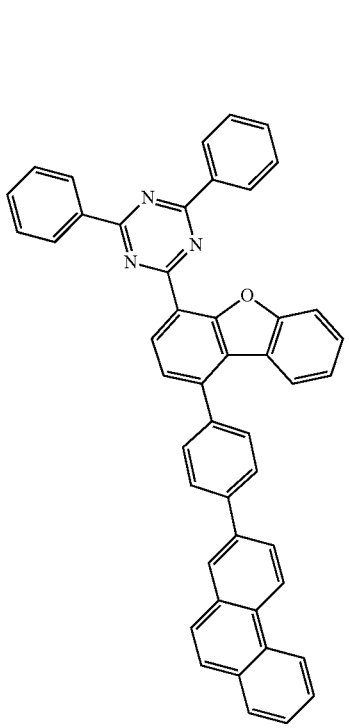

1-5-62
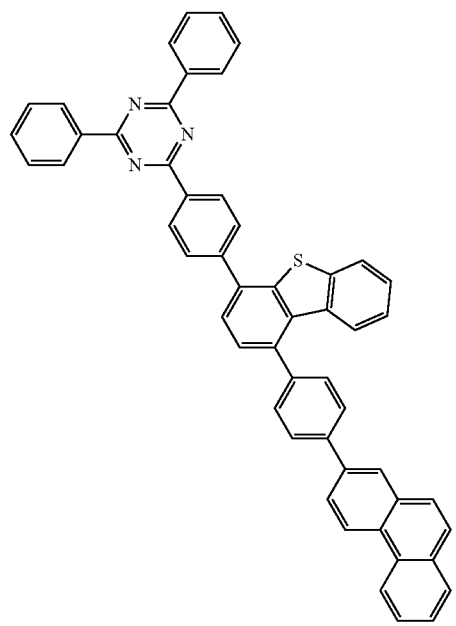
1-5-63
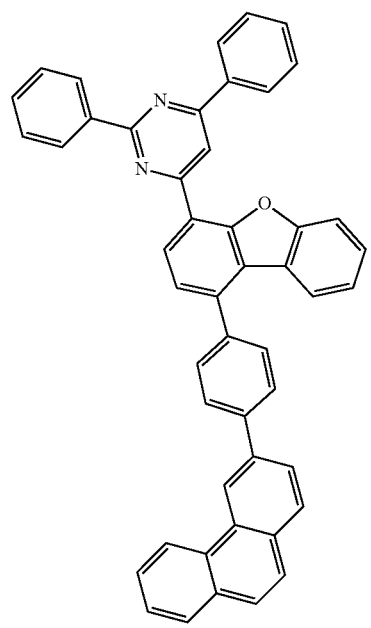
1-5-64
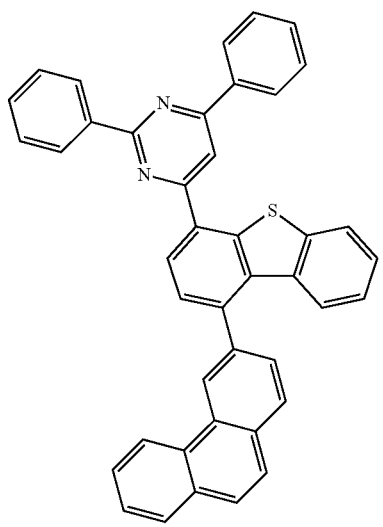
1-6-1
1-6-2
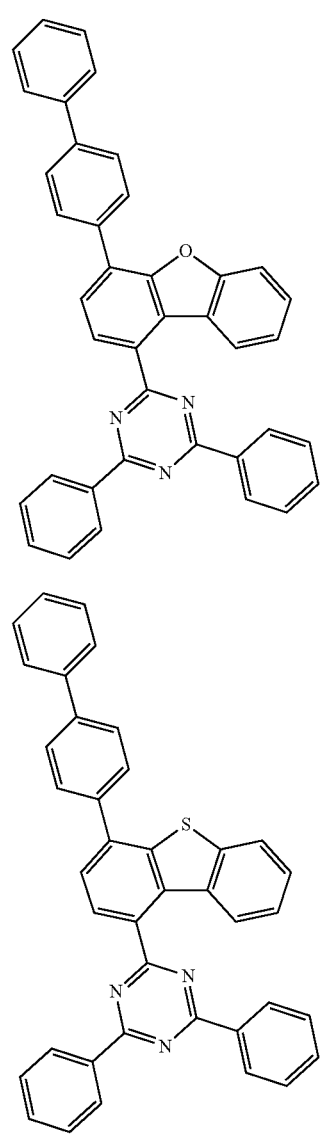

-continued
1-6-3
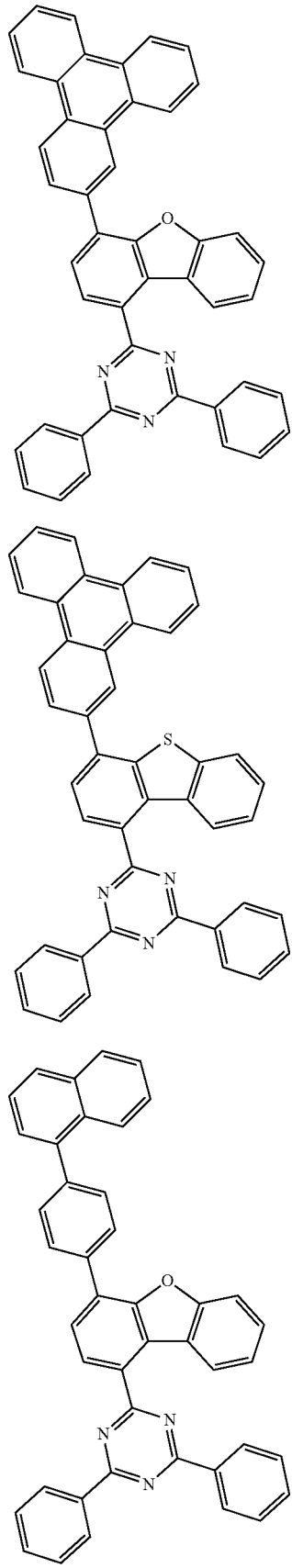
1-6-4
1-6-5
-continued
1-6-6
1-6-7

-continued
1-6-8
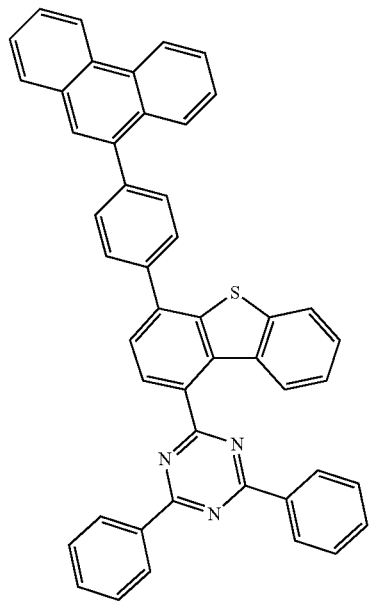
1-6-9
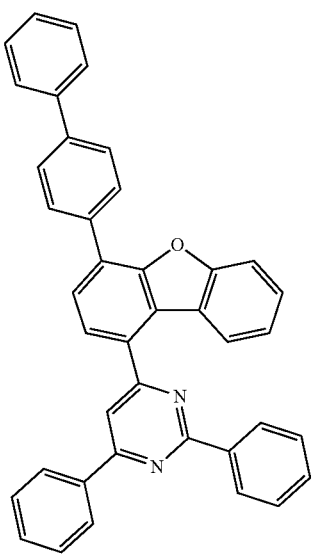
-continued
1-6-10
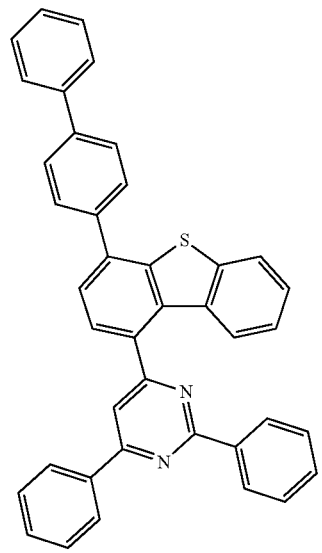
1-6-11
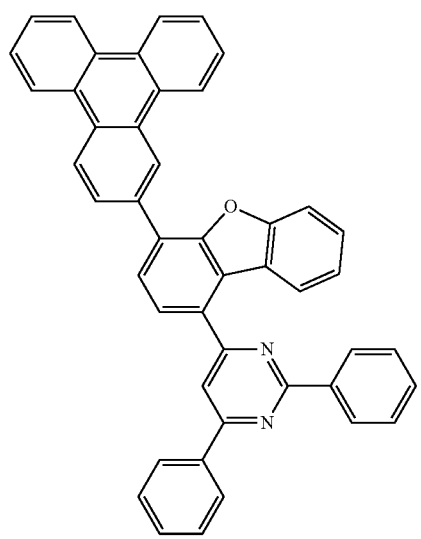
1-6-12
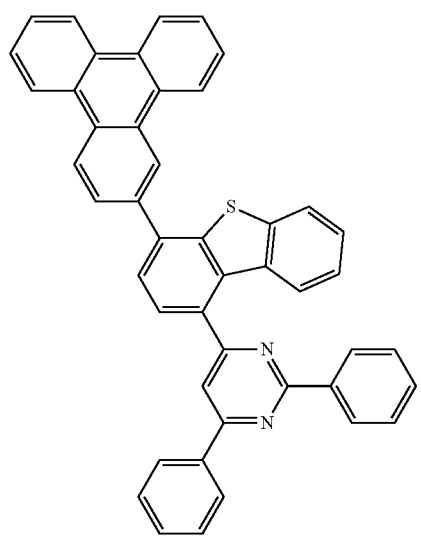

1-6-13
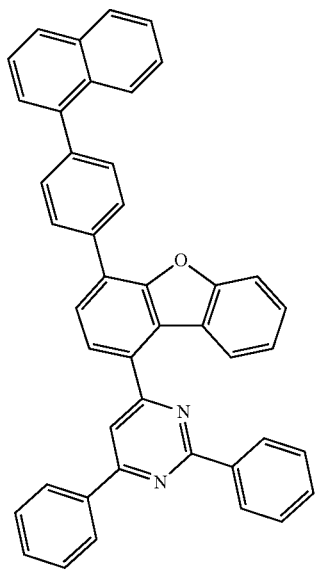
1-6-15
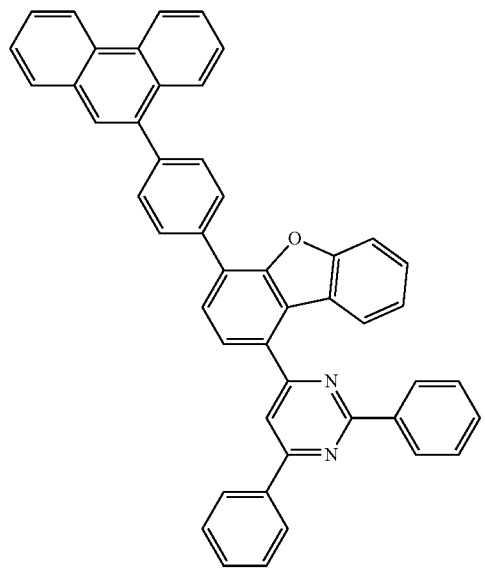
1-6-14
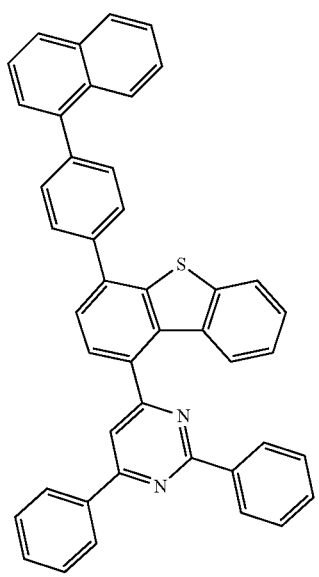
1-6-16
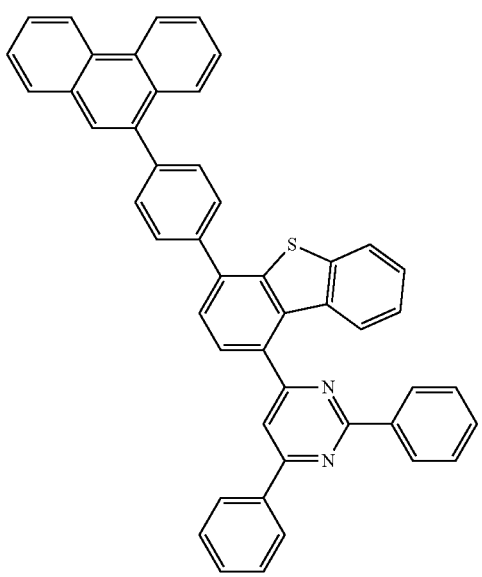

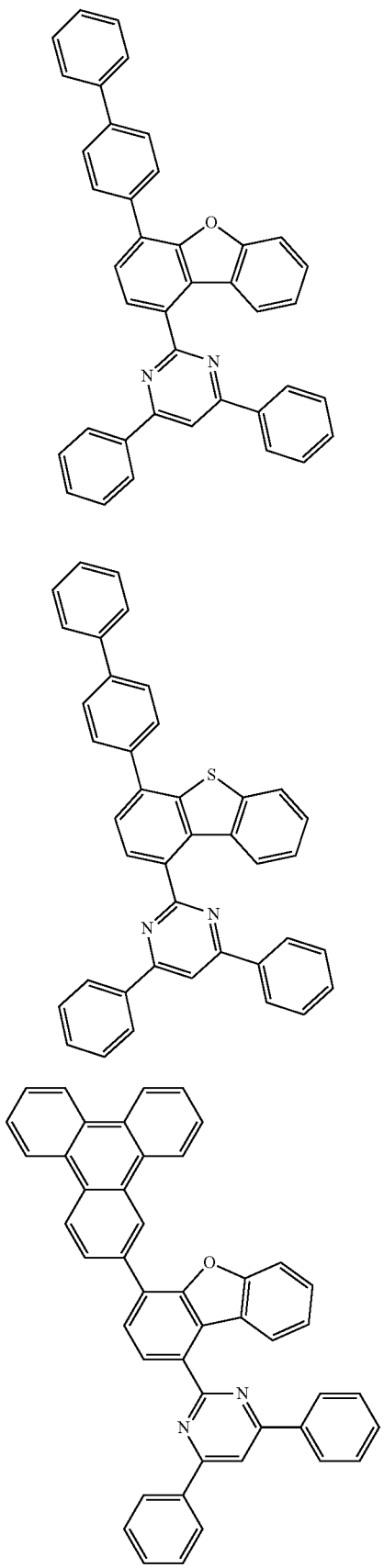
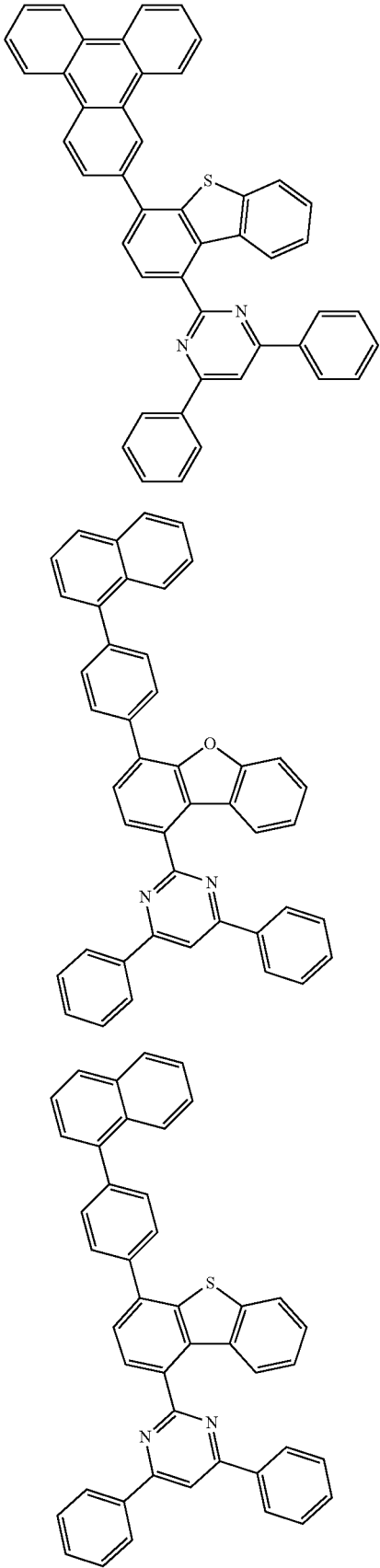

117
-continued
1-6-23
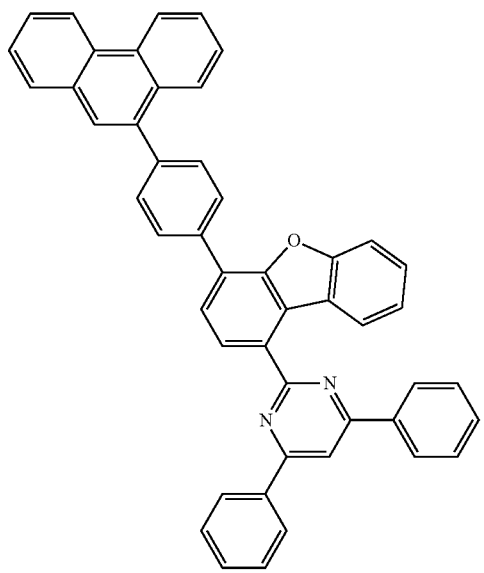
1-6-24
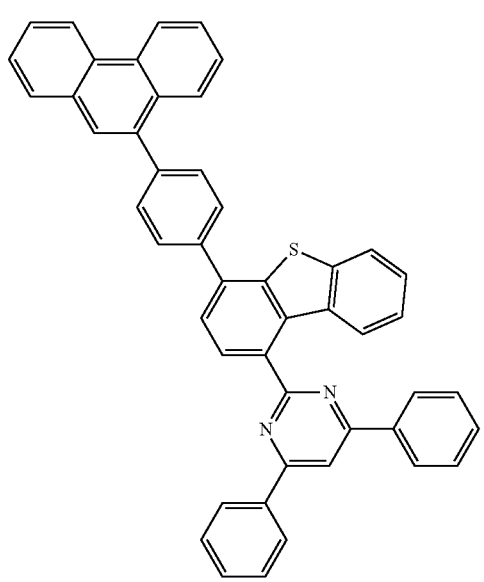
118
-continued
1-6-25
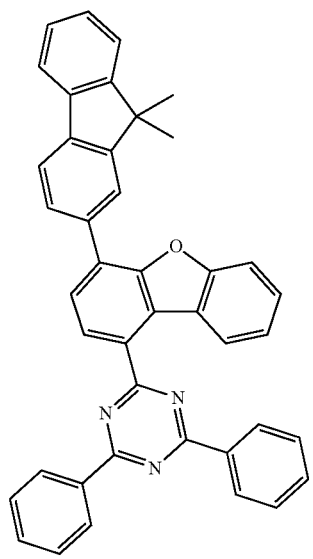
1-6-26
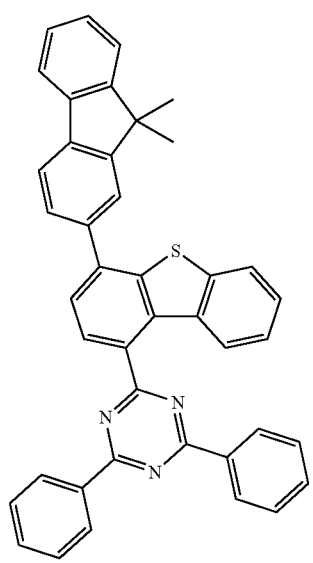

1-6-27
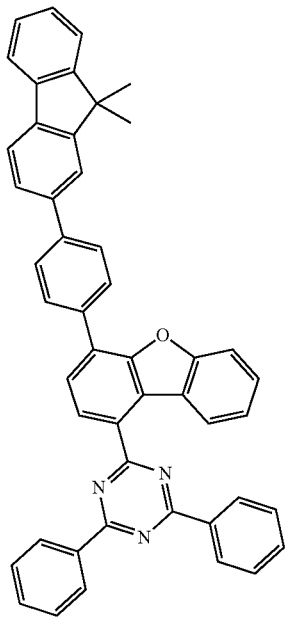
1-6-28
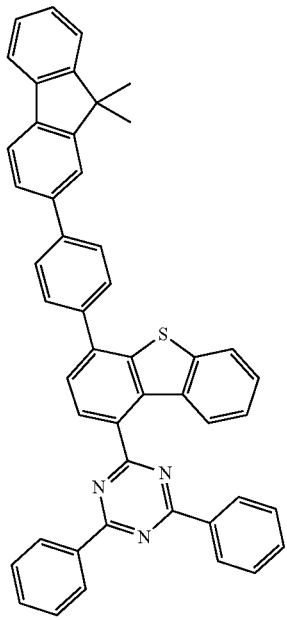
1-6-29
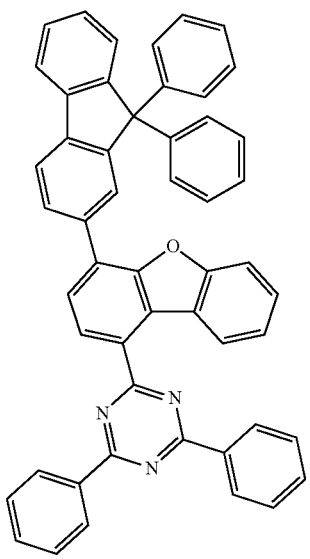
1-6-30
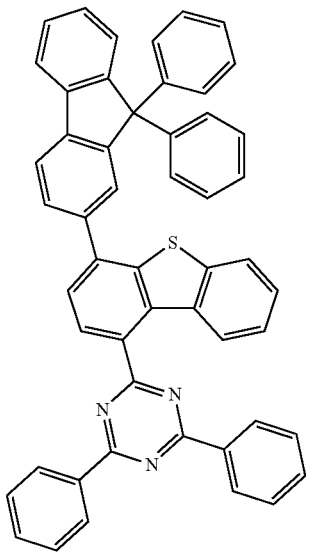

1-6-31
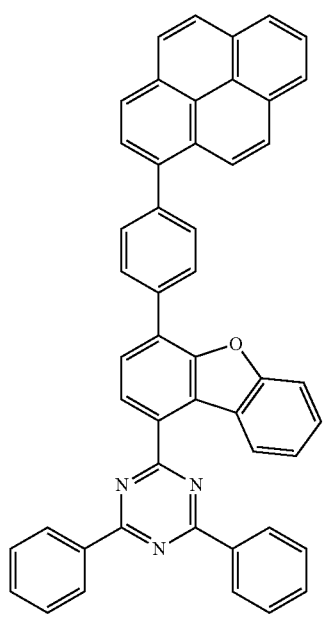
1-6-32
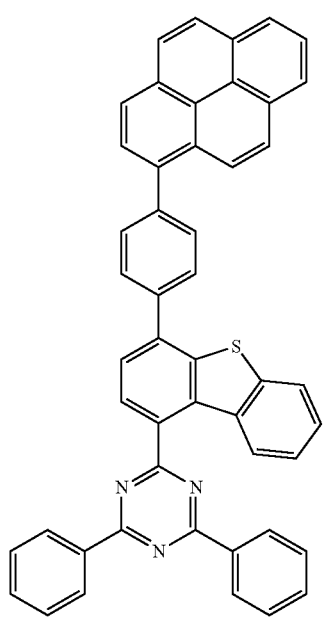
1-6-33
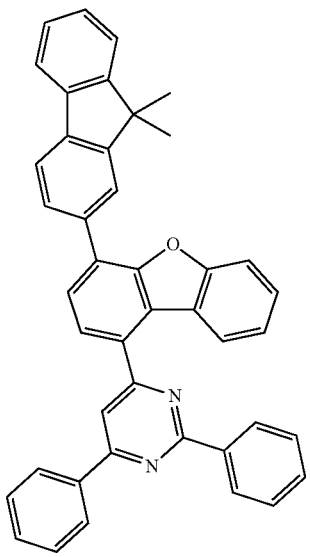
1-6-34
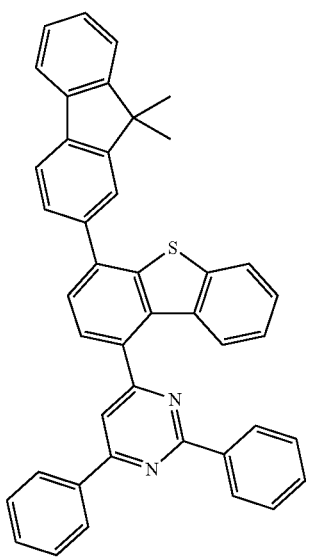

123
-continued
1-6-35
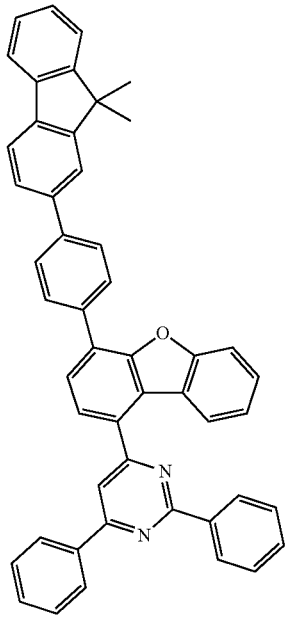
1-6-36
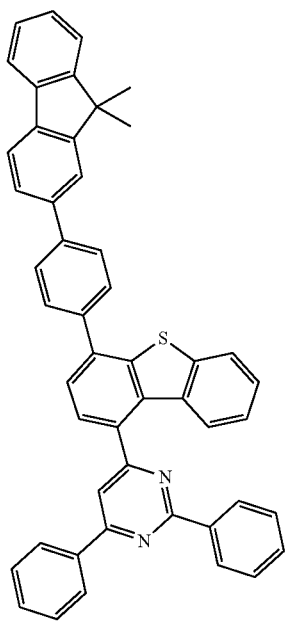
124
-continued
1-6-37
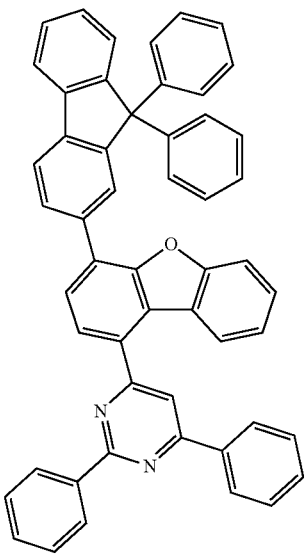
1-6-38
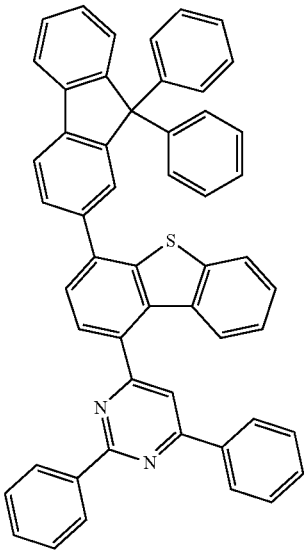

-continued
1-6-39
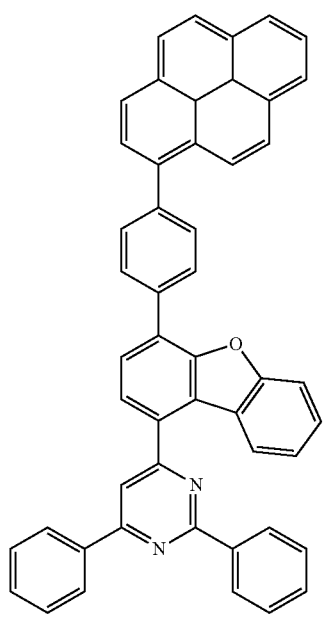
1-6-40
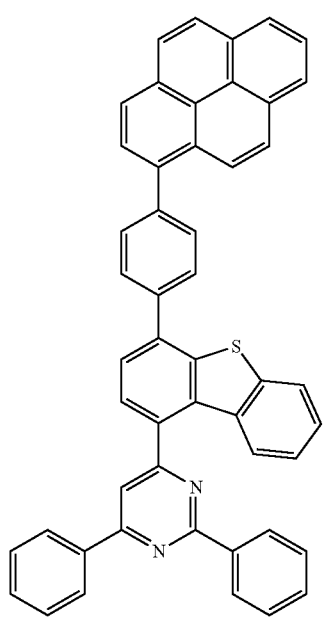
1-6-41
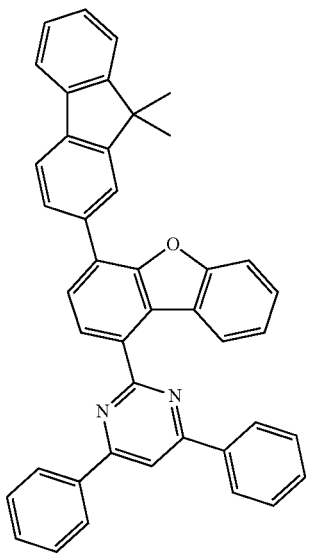
1-6-42
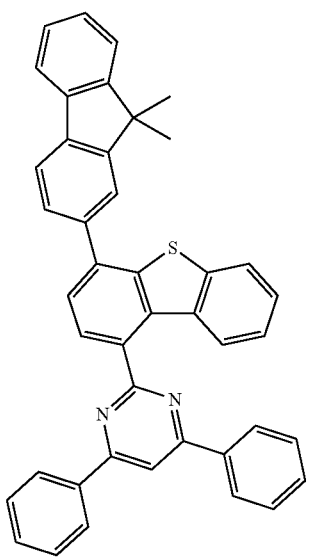

1-6-43
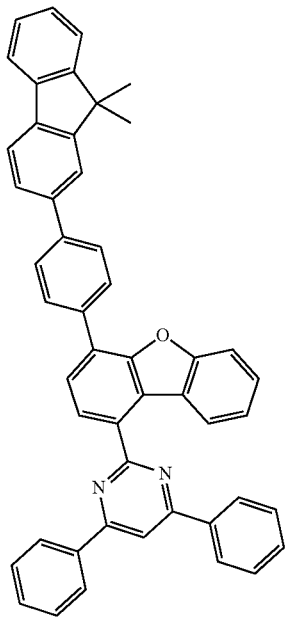
1-6-45
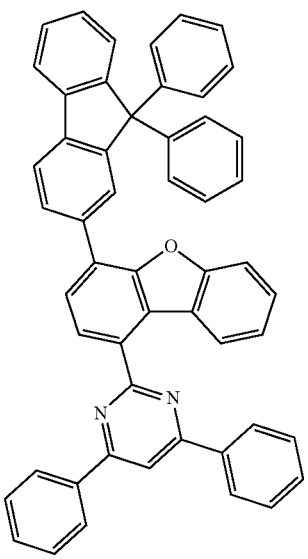
1-6-44
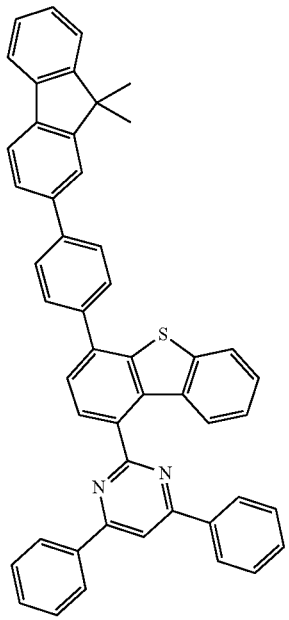
1-6-46
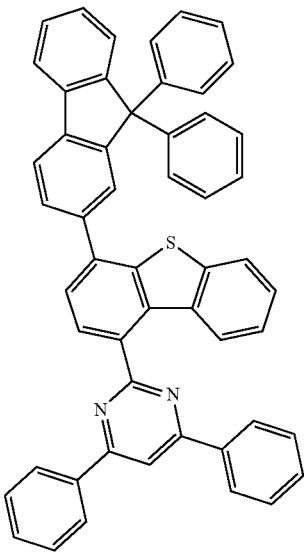

1-6-47
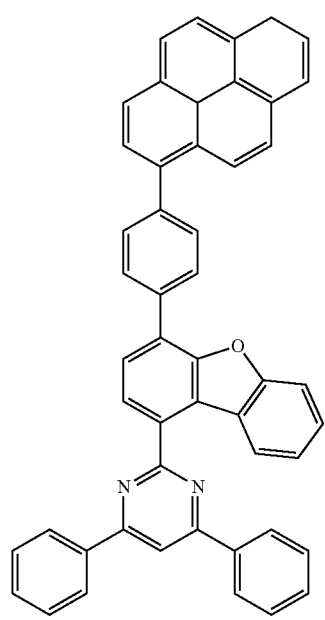
1-6-48
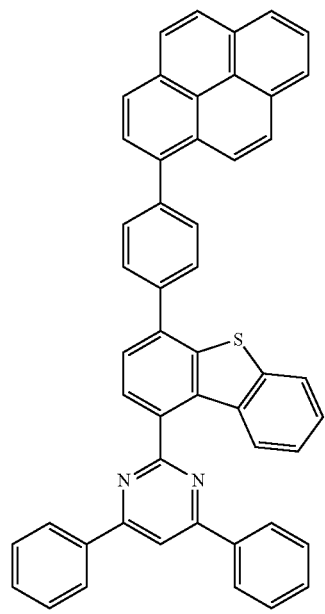
1-6-49
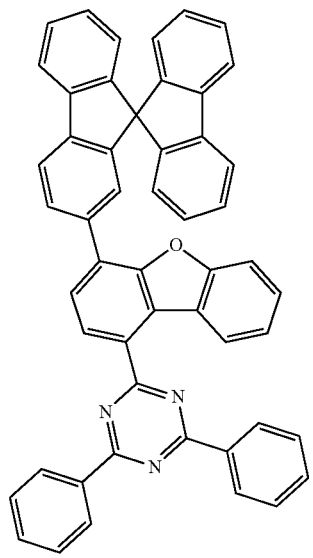
1-6-50
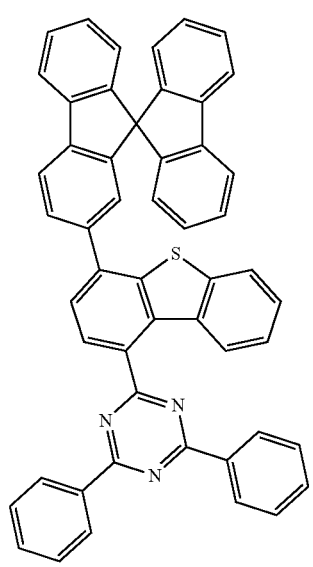
1-6-51
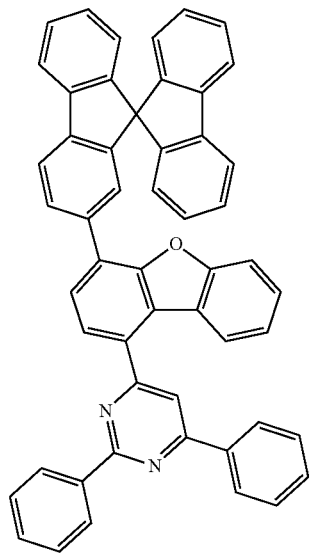

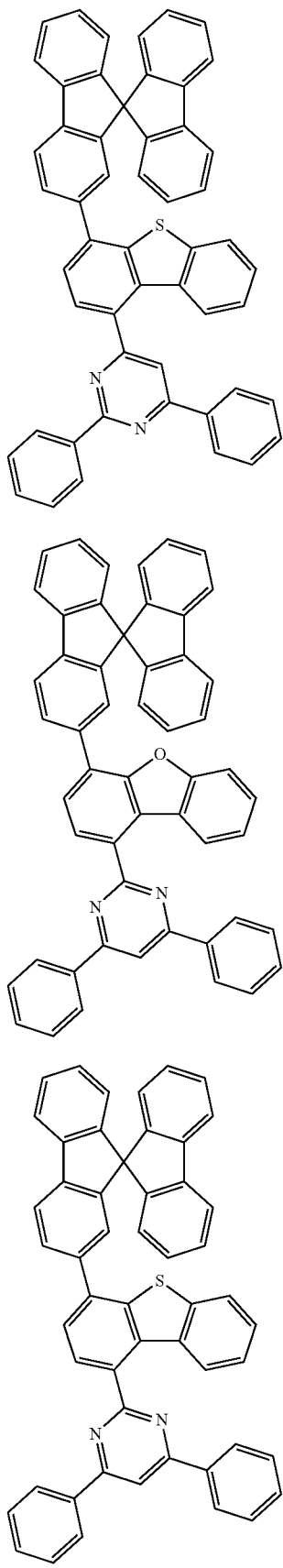
1-6-52
1-6-53
1-6-54
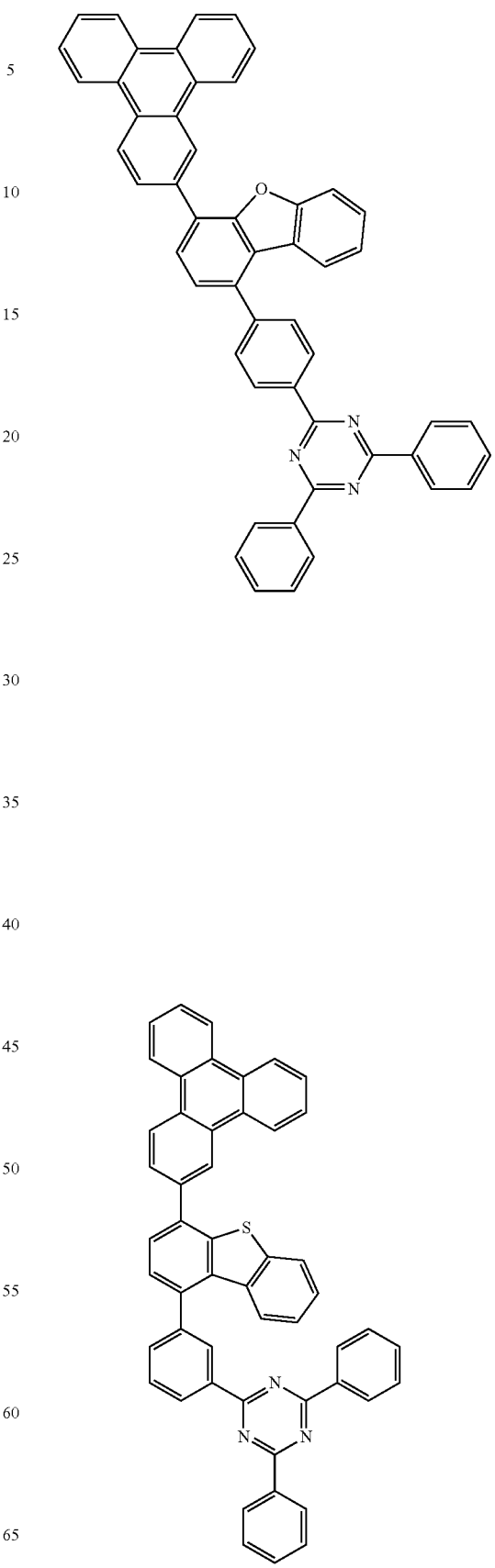
1-6-55
1-6-56

1-6-57
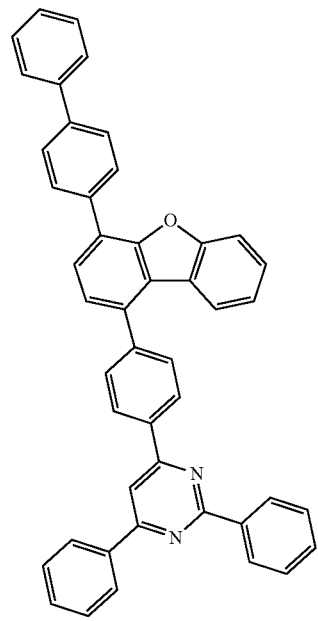
1-6-58
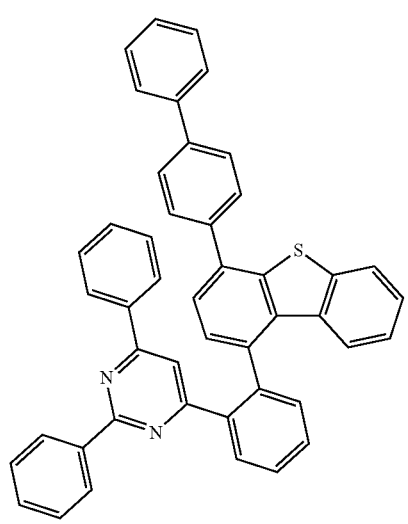
1-6-59
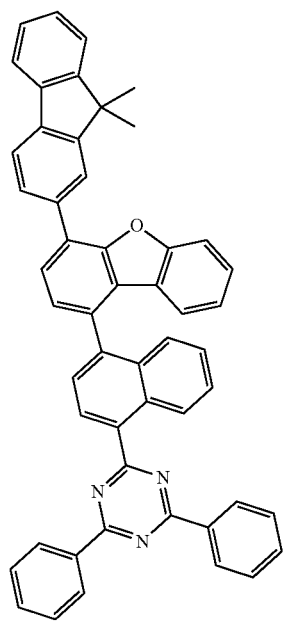
1-6-60
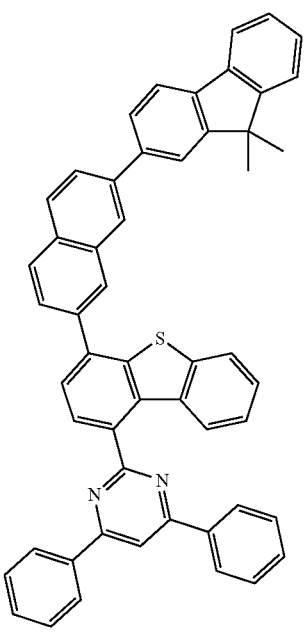

1-6-61
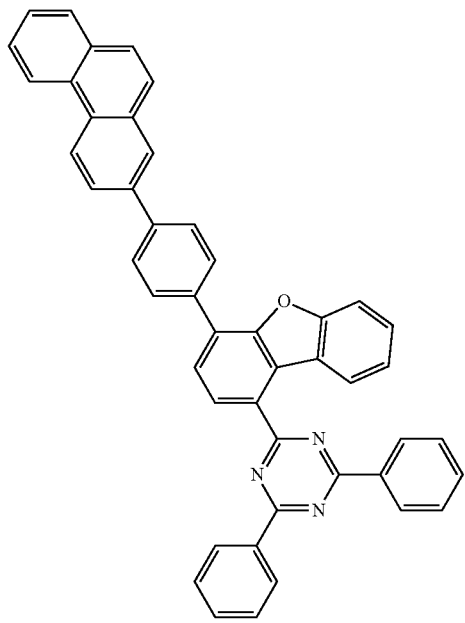
1-6-62
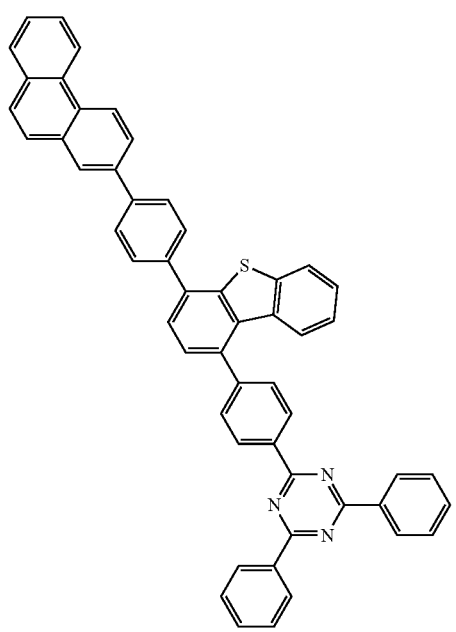
1-6-63
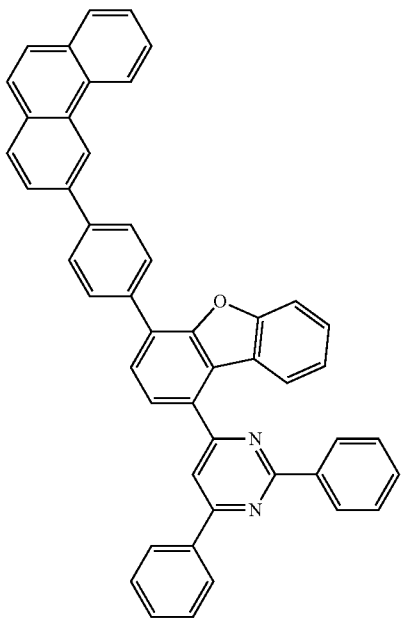
1-6-64
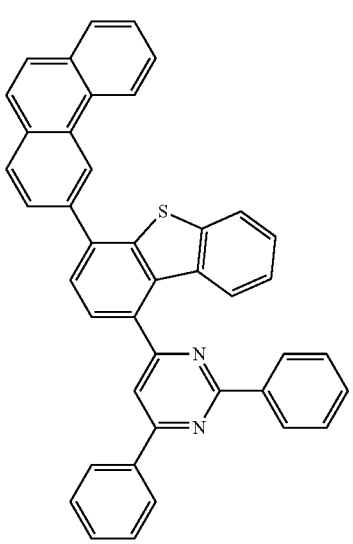
The compound of Chemical Formula 1 can be prepared by the method as shown in the following Reaction Scheme 1. The above preparation method can be further specified in Preparation Examples described hereinafter.
[Reaction Scheme 1]
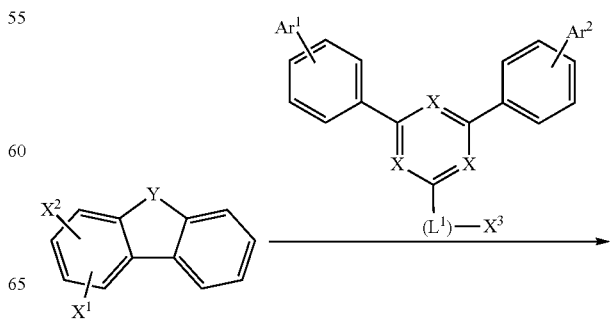

-continued

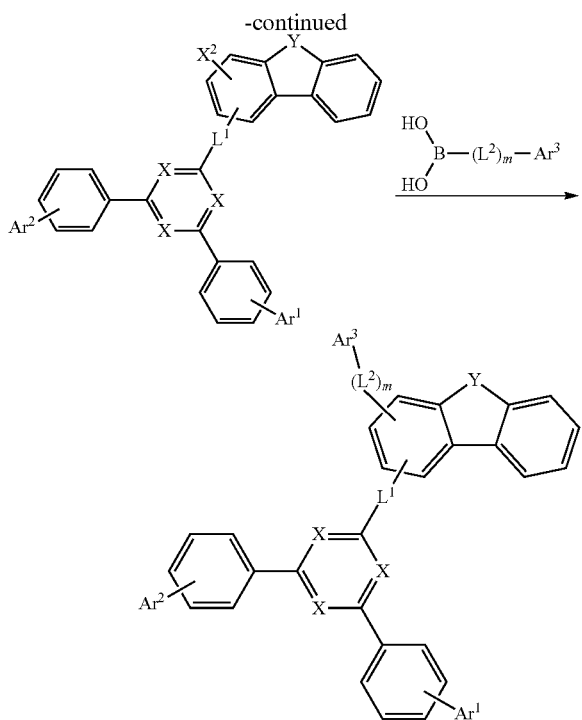

In Reaction Scheme 1, $X^1$ to $X^3$ are each independently a group such as —Cl, —Br, —I, —OTf, —ONf, or —OH, in which $X^1$ and $X^2$ are different groups; and X, Y, $L^1$, $L^2$, m, $Ar^1$, $Ar^2$, and $Ar^3$ are the same as those defined in Chemical Formula 1.

Meanwhile, according to another embodiment of the present disclosure, an organic electroluminescent device including a compound of Chemical Formula 1 is provided.

As an example, according to a further embodiment of the present disclosure, an organic electroluminescent device is provided, including: a first electrode; a second electrode provided opposite to the first electrode; and one or more organic material layers provided between the first electrode and the second electrode, wherein at least one layer of the organic material layers includes the compound of Chemical Formula 1.

The organic material layer of the organic electroluminescent device of the present disclosure can have a single layer structure, or it can have a multilayered structure in which two or more organic material layers are stacked.

For example, the organic electroluminescent device of the present disclosure can have a structure including a hole injection layer, a hole transport layer, a light emitting layer, an electron transport layer, an electron injection layer, and the like as the organic material layer. However, the structure of the organic electroluminescent device is not limited thereto, and it can include a smaller number of organic layers.

Further, the organic material layer can include a hole injection layer, a hole transport layer, or a layer simultaneously performing hole injection and transport, wherein the hole injection layer, the hole transport layer, and the layer simultaneously performing hole injection and transport include a compound of Chemical Formula 1.

The organic material layer can include a light emitting layer, wherein the light emitting layer can include a compound of Chemical Formula 1.

The organic material layer can include an electron transport layer or an electron injection layer, wherein the electron transport layer or the electron injection layer includes a compound of Chemical Formula 1.

The electron transport layer, the electron injection layer, or a layer simultaneously performing electron transport and electron injection include a compound of Chemical Formula 1.

The organic material layer includes a light emitting layer and an electron transport layer, wherein the electron transport layer can include a compound of Chemical Formula 1.

The organic electroluminescent device according to the present disclosure can be a normal type of organic electroluminescent device in which an anode, one or more organic material layers, and a cathode are sequentially stacked on a substrate.

The organic electroluminescent device according to the present disclosure can be an inverted type of organic electroluminescent device in which a cathode, one or more organic material layers, and an anode are sequentially stacked on a substrate.

For example, the structure of an organic electroluminescent device according to an embodiment of the present disclosure is illustrated in FIGS. 1 and 2.

FIG. 1 shows an example of an organic electroluminescent device including a substrate 1, an anode 2, a light emitting layer 3, and a cathode 4. In the structure as shown in FIG. 1, the compound of Chemical Formula 1 can be included in the light emitting layer.

FIG. 2 shows an example of an organic electroluminescent device including a substrate 1, an anode 2, a hole injection layer 5, a hole transport layer 6, a light emitting layer 7, an electron transport layer 8, and a cathode 4. In the structure as shown in FIG. 2, the compound of Chemical Formula 1 can be included in at least one layer of the hole injection layer, the hole transport layer, and the electron transport layer, and preferably, in the hole transport layer.

Meanwhile, the organic electroluminescent device according to the present disclosure can be manufactured by materials and methods known in the art, except that at least one layer of the organic material layers includes the compound of Chemical Formula 1.

In addition, when the organic electroluminescent device includes a plurality of organic material layers, the organic material layers can be formed of the same material or different materials.

For example, the organic electroluminescent device according to the present disclosure can be manufactured by sequentially stacking a first electrode, an organic material layer, and a second electrode on a substrate.

In this case, the organic electroluminescent device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon.

In addition to such a method, the organic electroluminescent device can be manufactured by sequentially depositing a cathode material, an organic material layer, and an anode material on a substrate.

Further, the compound of Chemical Formula 1 can be formed into an organic layer by a solution coating method as well as a vacuum deposition method at the time of manufacturing an organic electroluminescent device. Herein, the solution coating method means spin coating, dip coating, doctor blading, inkjet printing, screen printing, spraying, roll coating, or the like, but is not limited thereto.

In addition to such a method, the organic electroluminescent device can be manufactured by sequentially depositing a cathode material, an organic material layer, and an anode material on a substrate (International Publication WO2003/012890).

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer.

Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)thiophene] (PEDOT), polypyrrole, polyaniline, and the like, but are not limited thereto.

As the cathode material, generally, a material having a small work function is preferably used so that electrons can be easily injected into the organic material layer.

Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film.

It is preferable that a HOMO (highest occupied molecular orbital) of the hole injection material is between the work function of the anode material and a HOMO of a peripheral organic material layer.

Specific examples of the hole injection material include metal porphyrin, oligothiophene, an arylamine-based organic material, a hexanitrilehexa-azatriphenylene-based organic material, a quinacridone-based organic material, a perylene-based organic material, anthraquinone, a polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer.

Specific examples of the hole transport material include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence.

Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole, and benzimidazole-based compound; a poly(p-phenylene vinylene) (PPV)-based polymer; a spiro compound; polyfluorene; rubrene; and the like, but are not limited thereto.

The light emitting layer can include a host material and a dopant material. The host material can be a fused aromatic ring derivative, a heterocycle-containing compound, or the like.

Specific examples of the fused aromatic ring derivatives include anthracene derivatives, pyrene derivatives, naphthalene derivatives, pentacene derivatives, phenanthrene compounds, fluoranthene compounds, and the like. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like.

Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons.

Specific examples of the electron transport material include: an Al complex of 8-hydroxyquinoline; a complex including $Alq_3$; an organic radical compound; a hydroxyflavone-metal complex; and the like, but are not limited thereto.

The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic electroluminescent device according to the present disclosure can be a front side emission type, a back side emission type, or a double side emission type according to the material used.

In addition, the compound of Chemical Formula 1 can be included in an organic solar cell or an organic transistor in addition to an organic electroluminescent device.

Preferred examples are given to facilitate an understanding of the invention. However, these examples are presented for illustrative purposes only, and the scope of the invention is not limited thereto.

Synthesis Example 1

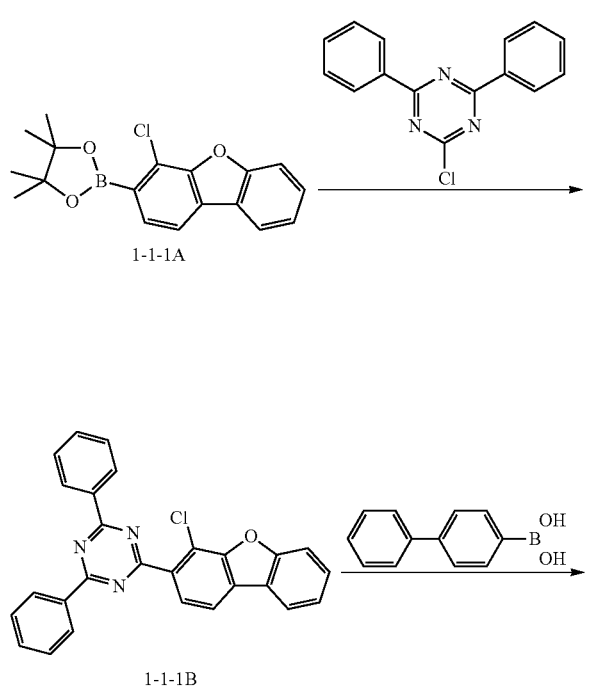

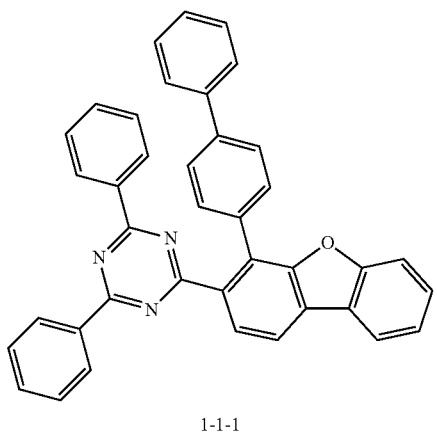

1-1-1

The compound 1-1-1A (20.0 g, 60.9 mmol), 2-chloro-4,6-diphenyl-1,3,5-triazine (16.3 g, 60.9 mmol), and potassium carbonate (19.6 g, 141.1 mmol) were added to THF (250 mL) under a nitrogen stream, and the mixture was heated and stirred. Tetrakis(triphenylphosphine)palladium (0) (2.11 g, 1.83 mmol) was added thereto, and then the mixture was heated and stirred for 4 hours. The reaction mixture was cooled to room temperature and then subjected to ethanol slurry purification to yield the compound 1-1-1B (25 g, yield 94.7%) (MS: [M+H]$^+$=434).

The compound 1-1-1B (25 g, 57.6 mmol), [1,1'-biphenyl]-4-ylboronic acid (11.4 g, 57.6 mmol), and potassium carbonate (15.9 g, 115.2 mmol) were added to THF (300 mL) under a nitrogen stream, and the mixture was heated and stirred. Potassium acetate (0.39 g, 1.73 mmol) and an S-Phos ligand (1.41 g, 3.46 mmol) were added thereto, and the mixture was heated and stirred for 2 hours. The reaction mixture was cooled to room temperature and then subjected to ethanol slurry purification to yield the compound 1-1-1 (29 g, yield 91.3%) (MS: [M+H]$^+$=552).

Synthesis Example 2

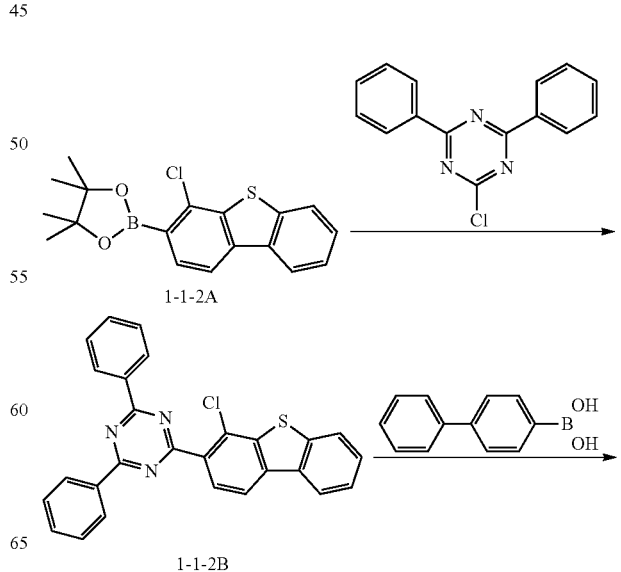

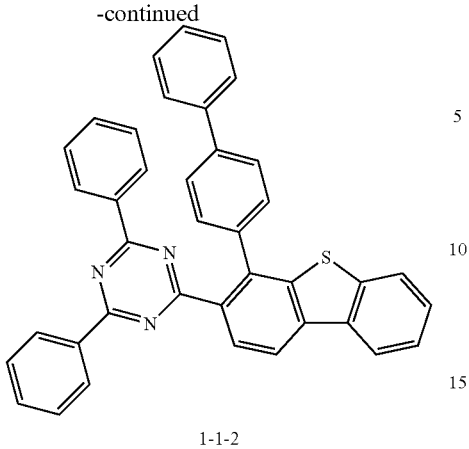

1-1-2

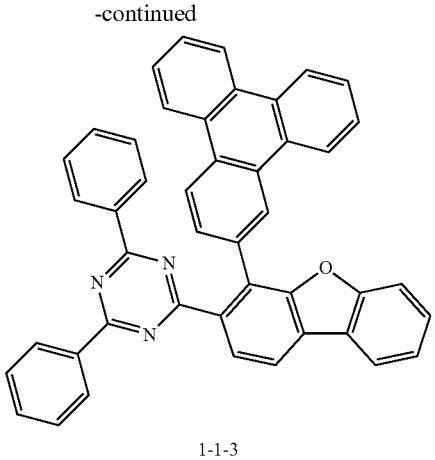

1-1-3

The compound 1-1-2A (20.0 g, 58.0 mmol), 2-chloro-4,6-diphenyl-1,3,5-triazine (15.5 g, 58.0 mmol), and potassium carbonate (16.0 g, 116.1 mmol) were added to THF (250 mL) under a nitrogen stream, and the mixture was heated and stirred. Tetrakis(triphenylphosphine)palladium (0) (2.01 g, 1.74 mmol) was added thereto, and then the mixture was heated and stirred for 4 hours. The reaction mixture was cooled to room temperature and then subjected to ethanol slurry purification to yield the compound 1-1-2B (24.0 g, yield 92.0%) (MS: $[M+H]^+$=450).

The compound 1-1-2B (24 g, 53.3 mmol), [1,1'-biphenyl]-4-ylboronic acid (10.6 g, 53.3 mmol), and potassium carbonate (14.7 g, 106.6 mmol) were added to THF (300 mL) under a nitrogen stream, and the mixture was heated and stirred. Potassium acetate (0.36 g, 1.60 mmol) and an S-Phos ligand (1.31 g, 3.20 mmol) were added thereto, and the mixture was heated and stirred for 2 hours. The reaction mixture was cooled to room temperature and then subjected to ethanol slurry purification to yield the compound 1-1-2 (28 g, yield 92.6%) (MS: $[M+H]^+$=568).

The compound 1-1-3A (20.0 g, 60.9 mmol), 2-chloro-4,6-diphenyl-1,3,5-triazine (16.3 g, 60.9 mmol), and potassium carbonate (16.8 g, 121.8 mmol) were added to THF (250 mL) under a nitrogen stream, and the mixture was heated and stirred. Tetrakis(triphenylphosphine)palladium (0) (2.11 g, 1.83 mmol) was added thereto, and then the mixture was heated and stirred for 4 hours. The reaction mixture was cooled to room temperature and then subjected to ethanol slurry purification to yield the compound 1-1-3B (24.5 g, yield 92.8%) (MS: $[M+H]^+$=434).

The compound 1-1-3B (24.5 g, 56.5 mmol), triphenylene-1-ylboronic acid (15.4 g, 56.5 mmol), and potassium carbonate (15.6 g, 112.9 mmol) were added to THF (300 mL) under a nitrogen stream, and the mixture was heated and stirred. Potassium acetate (0.38 g, 1.69 mmol) and an S-Phos ligand (0.69 g, 3.39 mmol) were added thereto, and the mixture was heated and stirred for 2.5 hours. The reaction mixture was cooled to room temperature and then subjected to ethanol slurry purification to yield the compound 1-1-3 (33 g, yield 93.5%) (MS: $[M+H]^+$=626).

Synthesis Example 3

Synthesis Example 4

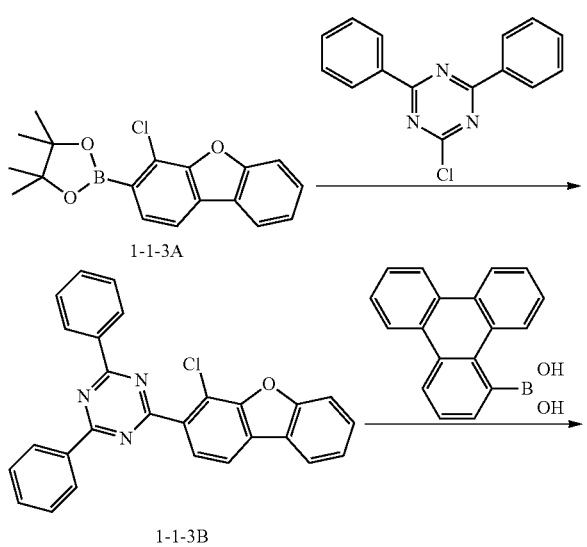

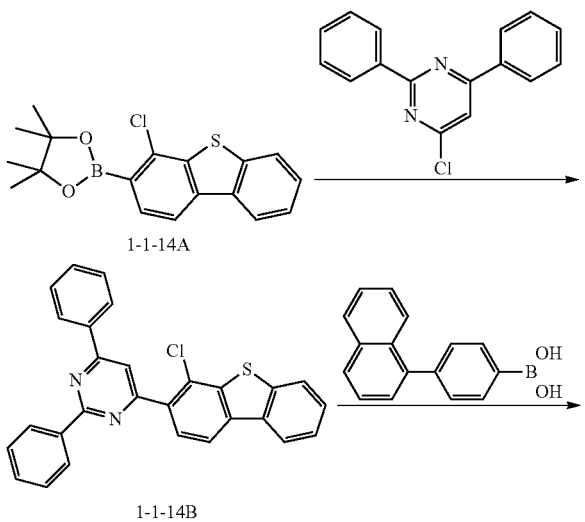

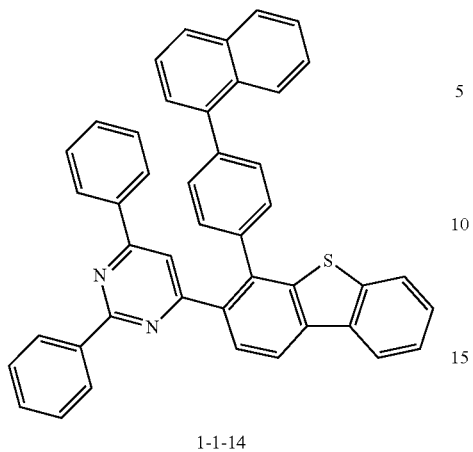

1-1-14

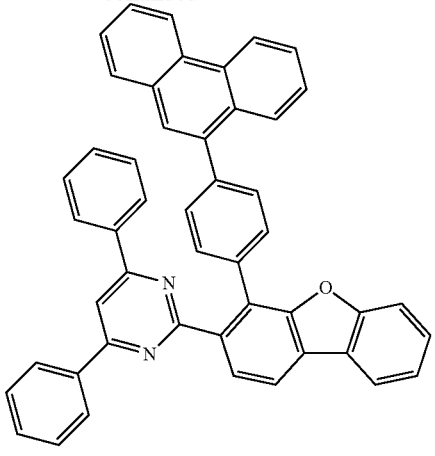

1-1-23

The compound 1-1-14A (20.0 g, 58.0 mmol), 4-chloro-2,6-diphenylpyrimidine (15.5 g, 58.0 mmol), and potassium carbonate (16.0 g, 116.1 mmol) were added to THF (250 mL) under a nitrogen stream, and the mixture was heated and stirred. Tetrakis(triphenylphosphine)palladium(0) (2.01 g, 1.74 mmol) was added thereto, and then the mixture was heated and stirred for 5 hours. The reaction mixture was cooled to room temperature and then subjected to ethanol slurry purification to yield the compound 1-1-14B (24 g, yield 92.1%) (MS: [M+H]$^+$=449).

The compound 1-1-14B (27 g, 53.5 mmol), (4-naphthalen-1-yl)phenyl)boronic acid (13.3 g, 53.5 mmol), and potassium carbonate (14.8 g, 106.9 mmol) were added to THF (300 mL) under a nitrogen stream, and the mixture was heated and stirred. Potassium acetate (0.36 g, 1.60 mmol) and an S-Phos ligand (1.31 g, 3.20 mmol) were added thereto, and the mixture was heated and stirred for 3 hours. The reaction mixture was cooled to room temperature and then subjected to ethanol slurry purification to yield the compound 1-1-14 (30 g, yield 91.2%) (MS: [M+H]$^+$=617).

The compound 1-1-23A (20.0 g, 60.9 mmol), 2-chloro-4,6-diphenylpyrimidine (16.2 g, 60.9 mmol), and potassium carbonate (16.8 g, 121.8 mmol) were added to THF (250 mL) under a nitrogen stream, and the mixture was heated and stirred. Tetrakis(triphenylphosphine)palladium(0) (2.11 g, 1.83 mmol) was added thereto, and then the mixture was heated and stirred for 5 hours. The reaction mixture was cooled to room temperature and then subjected to ethanol slurry purification to yield the compound 1-1-23B (23.5 g, yield 89.2%) (MS: [M+H]$^+$=449).

The compound 1-1-23B (23.5 g, 54.3 mmol), (4-naphthalen-1-yl)phenyl)boronic acid (16.2 g, 54.3 mmol), and potassium carbonate (15.0 g, 108.6 mmol) were added to THF (300 mL) under a nitrogen stream, and the mixture was heated and stirred. Potassium acetate (0.37 g, 1.63 mmol) and an S-Phos ligand (1.33 g, 3.26 mmol) were added thereto, and the mixture was heated and stirred for 3 hours. The reaction mixture was cooled to room temperature and then subjected to ethanol slurry purification to yield the compound 1-1-23 (34 g, yield 96.3%) (MS: [M+H]$^+$=651).

Synthesis Example 5

Synthesis Example 6

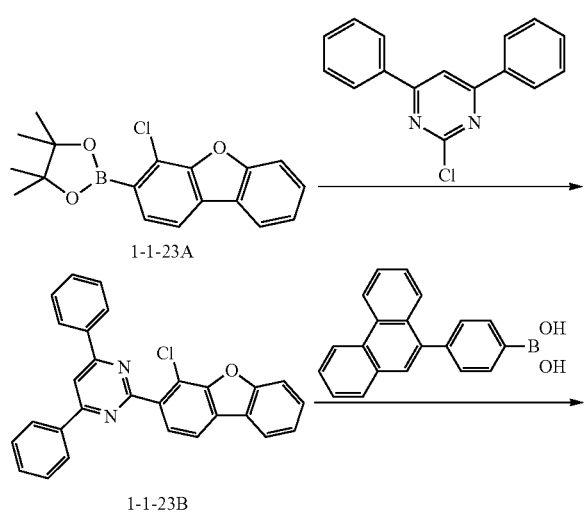

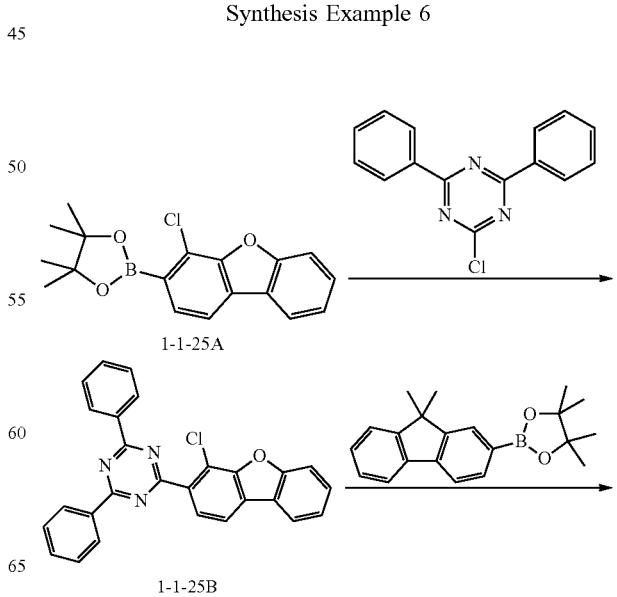

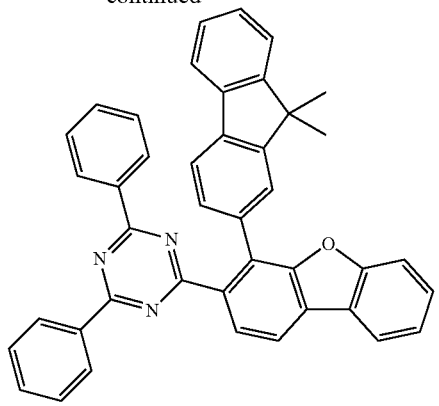

1-1-25

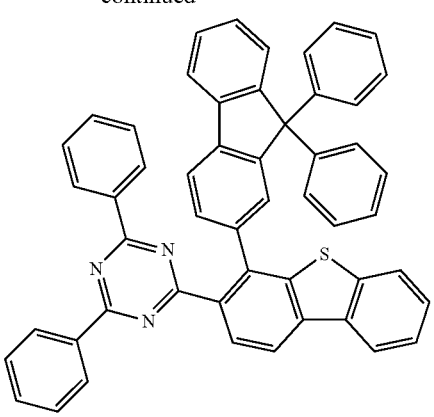

1-1-30

The compound 1-1-25A (20.0 g, 58.0 mmol), 2-chloro-4,6-diphenyl-1,3,5-triazine (15.5 g, 58.0 mmol), and potassium carbonate (16.0 g, 116.1 mmol) were added to THF (250 mL) under a nitrogen stream, and the mixture was heated and stirred. Tetrakis(triphenylphosphine)palladium (0) (2.01 g, 1.74 mmol) was added thereto, and then the mixture was heated and stirred for 5 hours. The reaction mixture was cooled to room temperature and then subjected to ethanol slurry purification to yield the compound 1-1-25B (23 g, yield 91.4%) (MS: $[M+H]^+$=434).

The compound 1-1-25B (23 g, 53.0 mmol), 2-(9,9-dimethyl-9H-fluoren-2-yl)-4,4,5,5-tetramethyl-1,3,2-dioxaborolane (17.0 g, 53.0 mmol), and potassium carbonate (14.6 g, 106.0 mmol) were added to THF (300 mL) under a nitrogen stream, and the mixture was heated and stirred. Potassium acetate (0.36 g, 1.59 mmol) and an S-Phos ligand (1.30 g, 3.18 mmol) were added thereto, and the mixture was heated and stirred for 3 hours. The reaction mixture was cooled to room temperature and then subjected to ethanol slurry purification to yield the compound 1-1-25 (29 g, yield 92.2%) (MS: $[M+H]^+$=592).

The compound 1-1-30A (20.0 g, 58.0 mmol), 2-chloro-4,6-diphenyl-1,3,5-triazine (15.5 g, 58.0 mmol), and potassium carbonate (16.0 g, 116.1 mmol) were added to THF (250 mL) under a nitrogen stream, and the mixture was heated and stirred. Tetrakis(triphenylphosphine)palladium (0) (2.01 g, 1.74 mmol) was added thereto, and then the mixture was heated and stirred for 5 hours. The reaction mixture was cooled to room temperature and then subjected to ethanol slurry purification to yield the compound 1-1-30B (24 g, yield 92.3%) (MS: $[M+H]^+$=450).

The compound 1-1-30B (24 g, 53.3 mmol), 2-(9,9-dimethyl-9H-fluoren-2-yl) boronic acid (19.3 g, 53.3 mmol), and potassium carbonate (14.7 g, 106.6 mmol) were added to THF (300 mL) under a nitrogen stream, and the mixture was heated and stirred. Potassium acetate (0.36 g, 1.60 mmol) and an S-Phos ligand (1.31 g, 3.20 mmol) were added thereto, and the mixture was heated and stirred for 3 hours. The reaction mixture was cooled to room temperature and then subjected to ethanol slurry purification to yield the compound 1-1-30 (36 g, yield 92.3%) (MS: $[M+H]^+$=732).

Synthesis Example 7

Synthesis Example 8

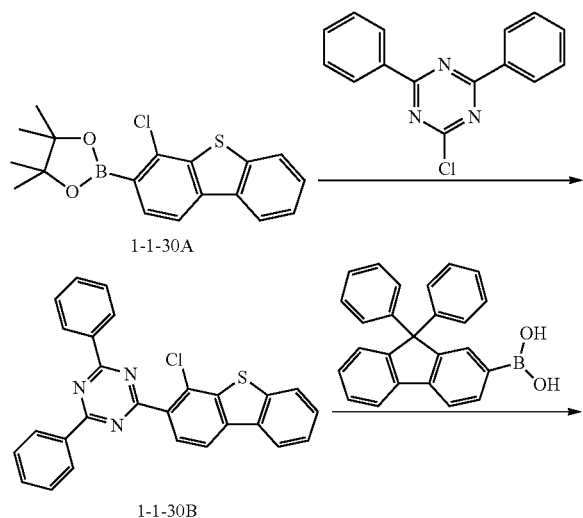

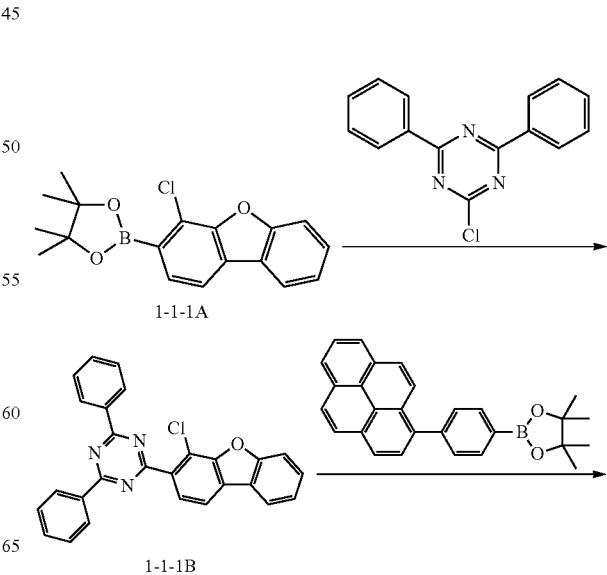

-continued

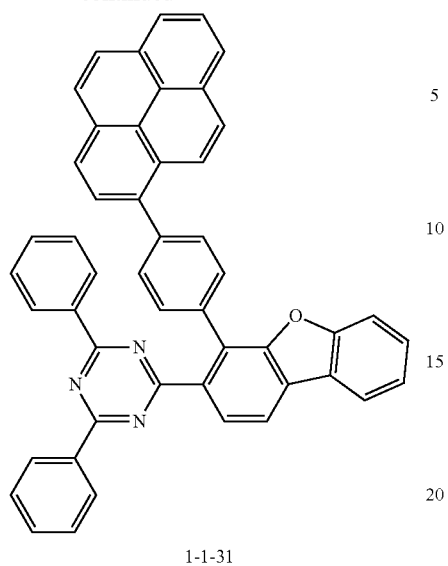

1-1-31

The compound 1-1-31 was prepared in the same manner as in the preparation of the compound 1-1-1 according to Synthesis Example 1, except that 4,4,5,5-tetramethyl-2-(4-(pyrene-1-yl)phenyl)-1,3,2-dioxaborolane was used instead of [1,1'-biphenyl]-4-ylboronic acid (MS: [M+H]$^+$=676).

Synthesis Example 9

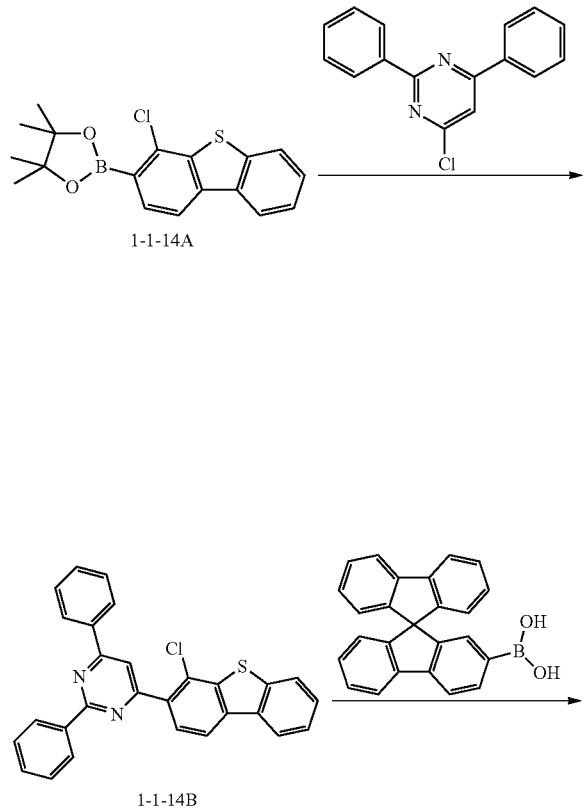

-continued

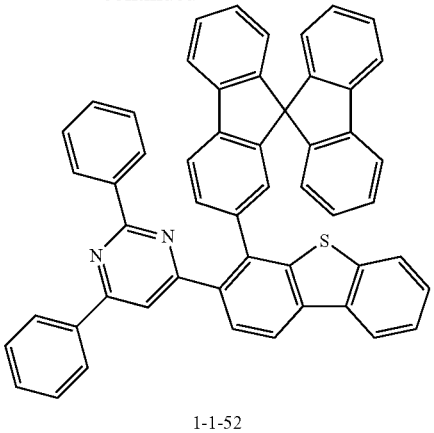

1-1-52

The compound 1-1-52 was prepared in the same manner as in the preparation of the compound 1-1-14 according to Synthesis Example 4, except that 9,9'-spirobi[fluorene]-2-ylboronic acid was used instead of (4-(naphthalen-1-yl)phenyl)boronic acid (MS: [M+H]$^+$=729).

Synthesis Example 10

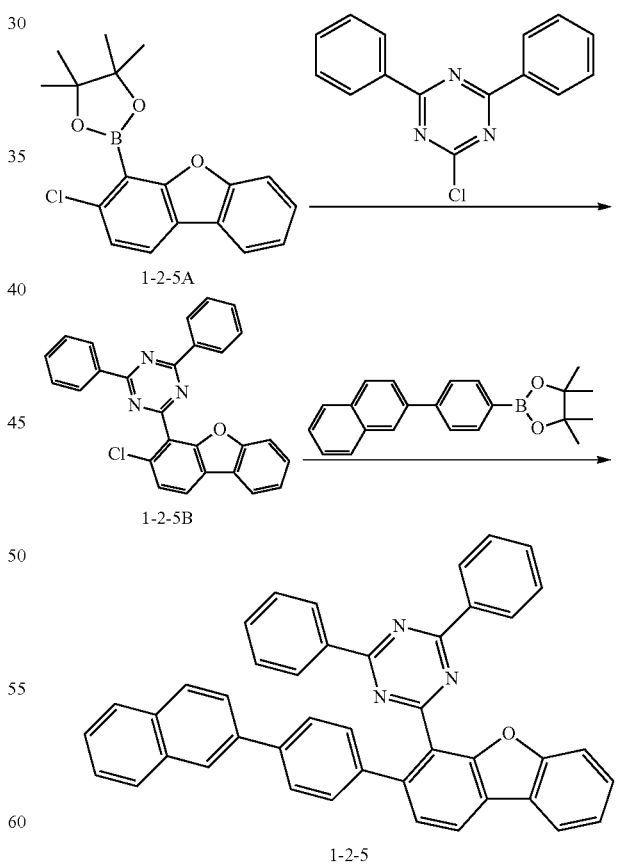

The compound 1-1-5A (20.0 g, 60.9 mmol), 2-chloro-4,6-diphenyl-1,3,5-triazine (16.3 g, 60.9 mmol) and potassium carbonate (16.8 g, 121.8 mmol) were added to THF (250 mL) under a nitrogen stream, and the mixture was heated and stirred. Tetrakis(triphenylphosphine)palladium(0) (2.11 g, 1.83 mmol) was added thereto, and then the mixture was heated and stirred for 5 hours. The reaction mixture was cooled to room temperature and then subjected to ethanol slurry purification to yield the compound 1-2-5B (24 g, yield 94.7%) (MS: [M+H]$^+$=434).

The compound 1-2-5B (24 g, 55.3 mmol), 4,4,5,5-tetramethyl-2-(4-(naphthalen-2-yl)phenyl)-1,3,2-dioxaborolane (18.3 g, 55.3 mmol), and potassium carbonate (15.3 g, 110.6 mmol) were added to THF (300 mL) under a nitrogen stream, and the mixture was heated and stirred. Potassium acetate (0.37 g, 1.66 mmol) and an S-Phos ligand (1.36 g, 3.32 mmol) were added thereto, and the mixture was heated and stirred for 3 hours. The reaction mixture was cooled to room temperature and then subjected to ethanol slurry purification to yield the compound 1-2-5 (30 g, yield 90.4%) (MS: [M+H]$^+$=602).

Synthesis Example 11

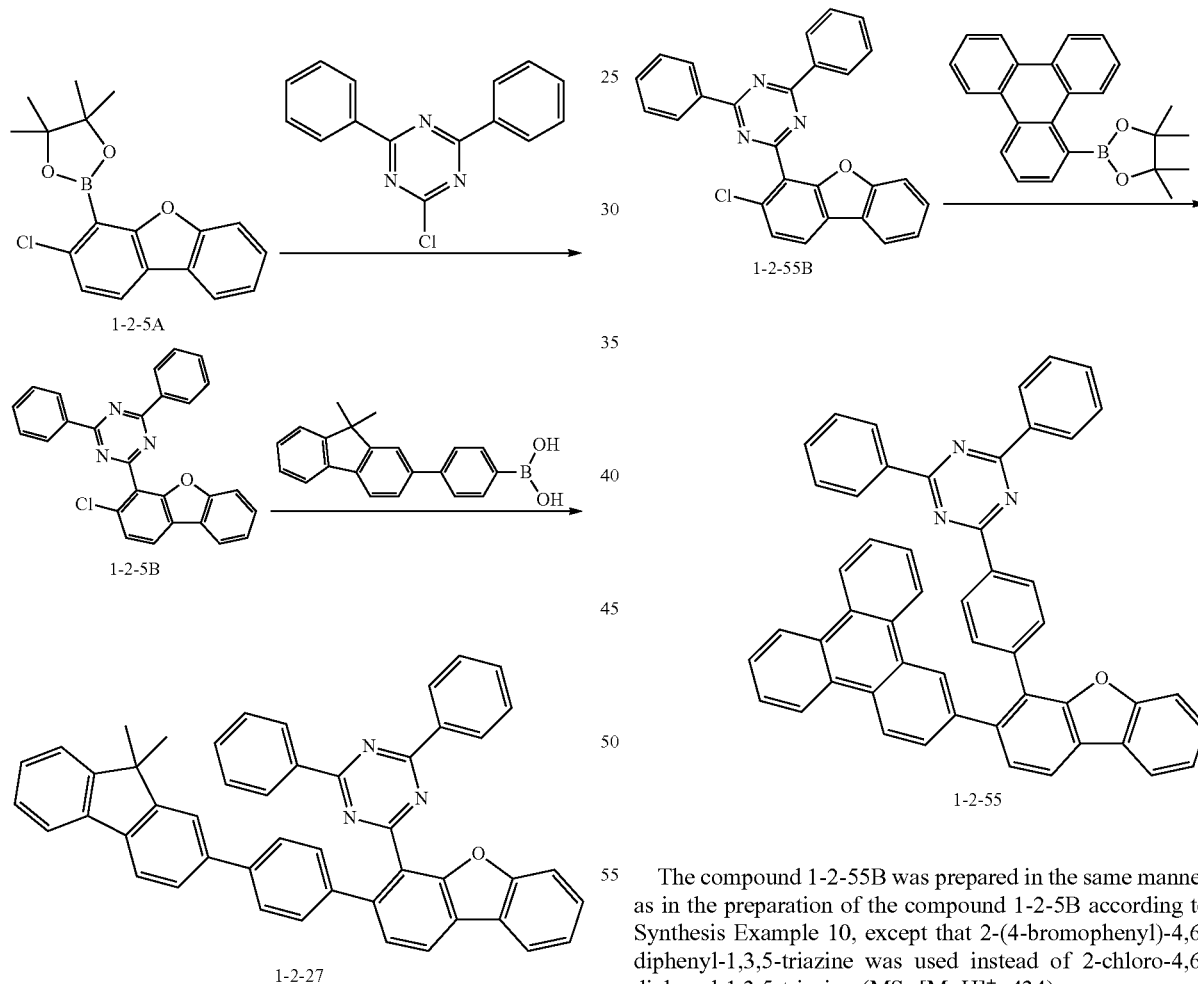

The compound 1-2-27 was prepared in the same manner as in the preparation of the compound 1-2-5 according to Synthesis Example 10, except that (4-(9,9-dimethyl-9H-fluoren-2-yl)phenyl)boronic acid was used instead of 4,4,5,5-tetramethyl-2-(4-(naphthalen-2-yl)phenyl)-1,3,2-dioxaborolane (MS: [M+H]$^+$=668).

Synthesis Example 12

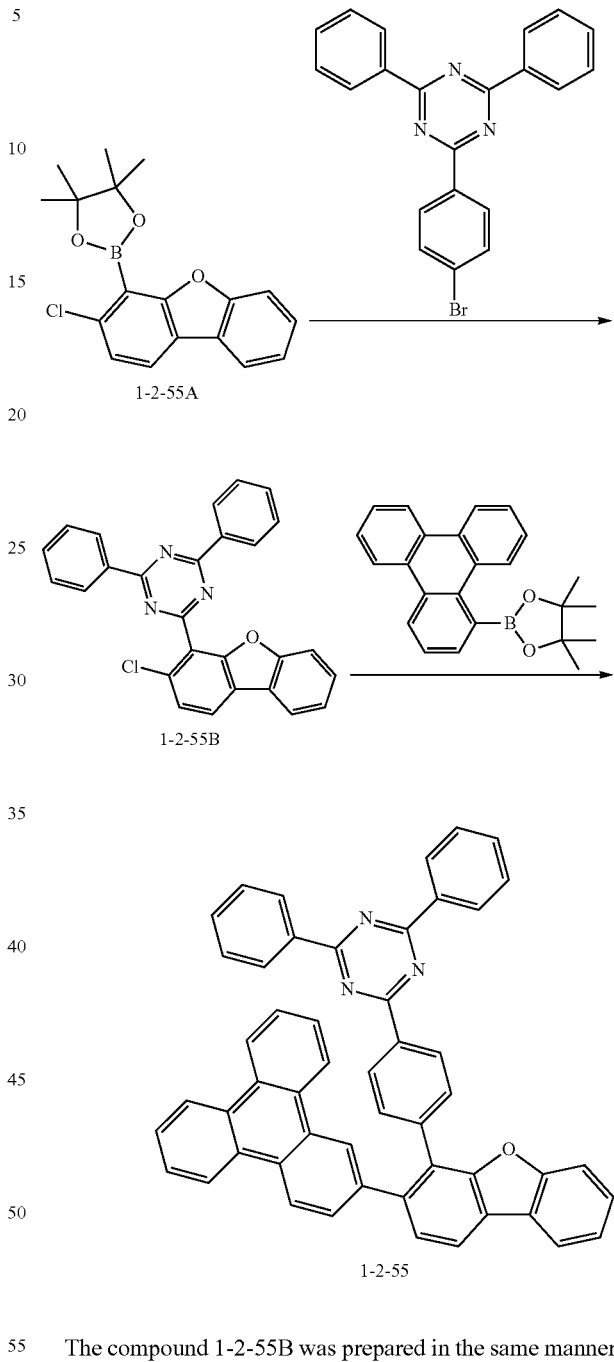

The compound 1-2-55B was prepared in the same manner as in the preparation of the compound 1-2-5B according to Synthesis Example 10, except that 2-(4-bromophenyl)-4,6-diphenyl-1,3,5-triazine was used instead of 2-chloro-4,6-diphenyl-1,3,5-triazine (MS: [M+H]$^+$=434).

The compound 1-2-55 was prepared in the same manner as in the preparation of the compound 1-2-5 according to Synthesis Example 10, except that the compound 1-2-55B was used instead of the compound 1-2-5B and 4,4,5,5-tetramethyl-2-(triphenylene-1-yl)-1,3,2-dioxaborolane was used instead of 4,4,5,5-tetramethyl-2-(4-(naphthalen-2-yl)phenyl)-1,3,2-dioxaborolane (MS: [M+H]$^+$=702).

Synthesis Example 13

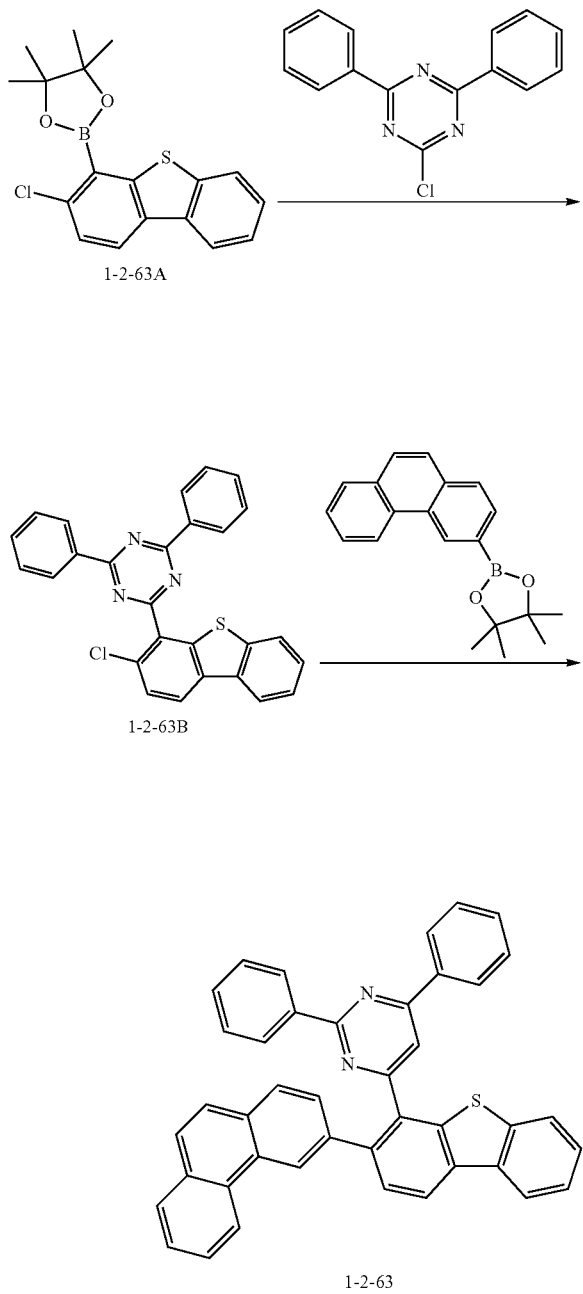

The compound 1-2-63B was prepared in the same manner as in the preparation of the compound 1-2-5B according to Synthesis Example 10, except that the compound 1-2-63A was used instead of the compound 1-2-5A (MS: [M+H]$^+$=450).

The compound 1-2-63 was prepared in the same manner as in the preparation of the compound 1-2-5 according to Synthesis Example 10, except that the compound 1-2-63B was used instead of the compound 1-2-5B and 4,4,5,5-tetramethyl-2-(phenanthrene-3-yl)-1,3,2-dioxaborolane was used instead of 4,4,5,5-tetramethyl-2-(4-(naphthalen-2-yl)phenyl)-1,3,2-dioxaborolane (MS: [M+H]$^+$=591).

Synthesis Example 14

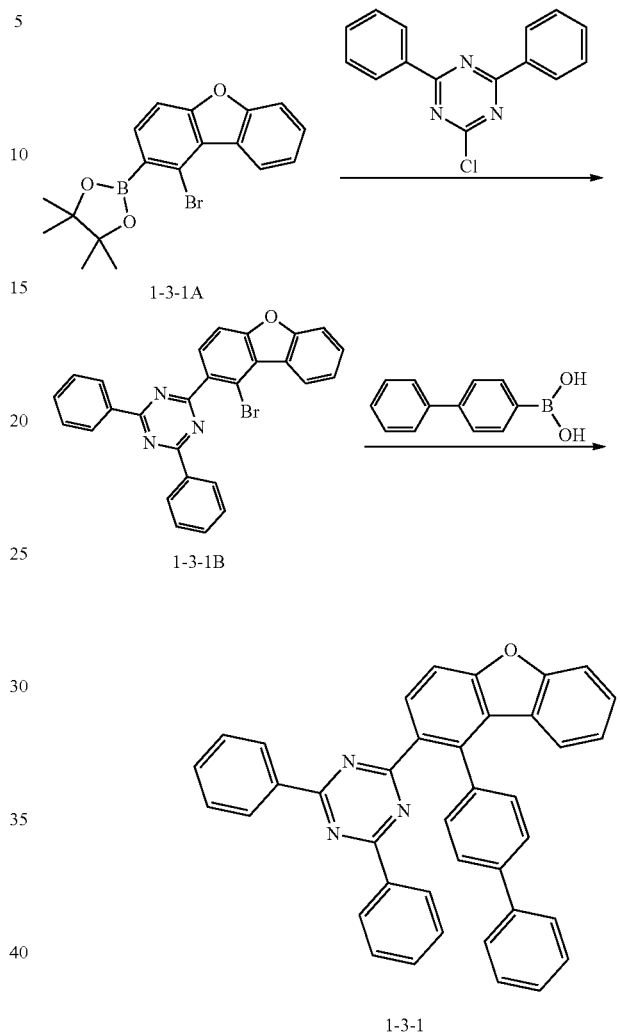

The compound 1-3-1A (20.0 g, 53.6 mmol), 2-chloro-4,6-diphenyl-1,3,5-triazine (14.4 g, 53.6 mmol), and potassium carbonate (14.8 g, 107.2 mmol) were added to THF (250 mL) under a nitrogen stream, and the mixture was heated and stirred. Tetrakis(triphenylphosphine)palladium (0) (1.85 g, 1.61 mmol) was added thereto, and then the mixture was heated and stirred for 5 hours. The reaction mixture was cooled to room temperature and then subjected to ethanol slurry purification to yield the compound 1-3-1B (24.5 g, yield 92.6%) (MS: [M+H]$^+$=478).

The compound 1-3-1B (24.5 g, 51.2 mmol), 4,4,5,5-tetramethyl-2-(4-(naphthalen-2-yl)phenyl)-1,3,2-dioxaborolane (10.1 g, 51.2 mmol), and potassium carbonate (14.2 g, 102.4 mmol) were added to THF (300 mL) under a nitrogen stream, and the mixture was heated and stirred. Potassium acetate (0.35 g, 1.54 mmol) and an S-Phos ligand (1.26 g, 3.07 mmol) were added thereto, and the mixture was heated and stirred for 3 hours. The reaction mixture was cooled to room temperature and then subjected to ethanol slurry purification to yield the compound 1-3-1 (28 g, yield 92.2%) (MS: [M+H]$^+$=552).

Synthesis Example 15

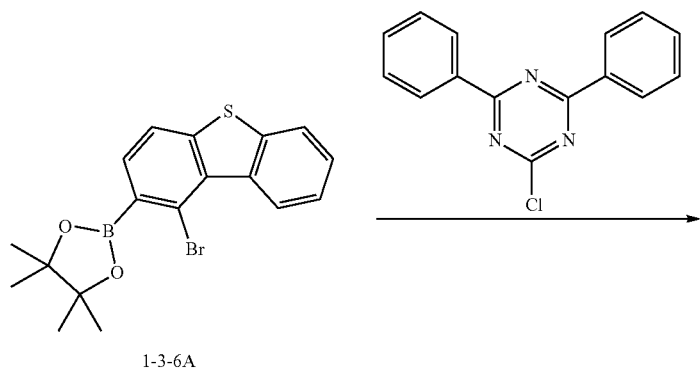

1-3-6A

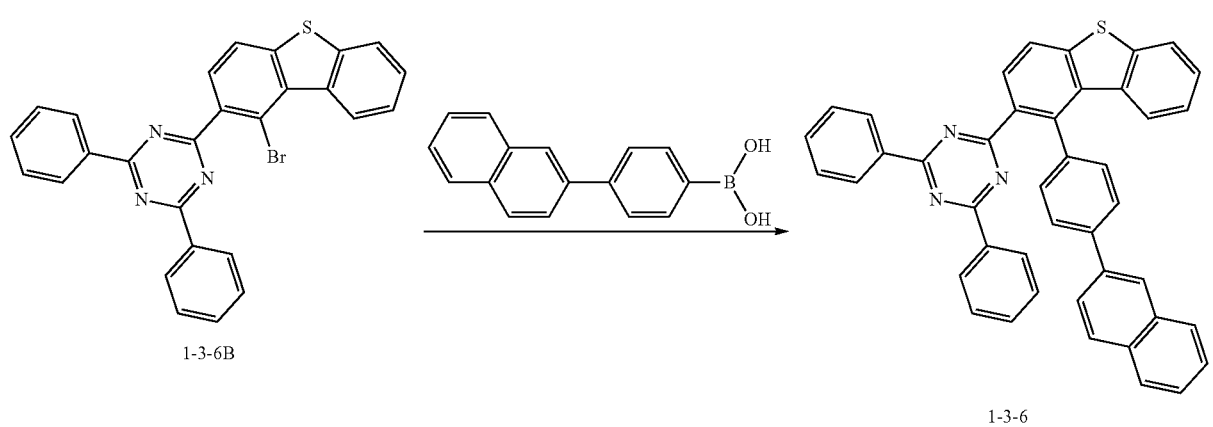

1-3-6B 1-3-6

The compound 1-3-6B was prepared in the same manner as in the preparation of the compound 1-3-1B according to Synthesis Example 14, except that the compound 1-3-6A was used instead of the compound 1-3-2A (MS: [M+H]⁺= 494).

The compound 1-3-6 was prepared in the same manner as in the preparation of the compound 1-3-1 according to Synthesis Example 14, except that the compound 1-3-6B was used instead of the compound 1-3-1B and (4-(naphthalen-2-yl)phenyl)boronic acid was used instead of [1,1'-biphenyl]-4-ylboronic acid (MS: [M+H]⁺=618).

Synthesis Example 16

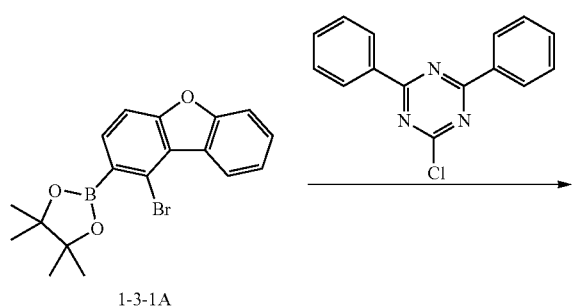

1-3-1A

-continued

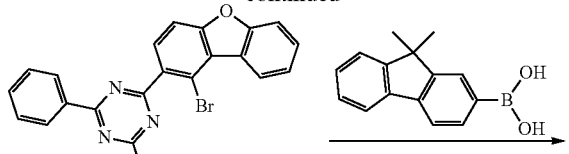

1-3-1B

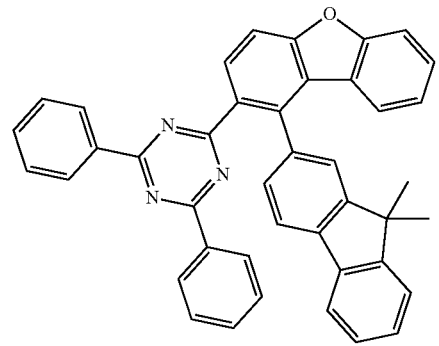

1-3-25

The compound 1-3-25 was prepared in the same manner as in the preparation of the compound 1-3-1 according to Synthesis Example 14, except that (9,9-dimethyl-9H-fluoren-2-yl)boronic acid was used instead of [1,1'-biphenyl]-4-ylboronic acid (MS: [M+H]⁺=592).

Synthesis Example 17

Synthesis Example 18

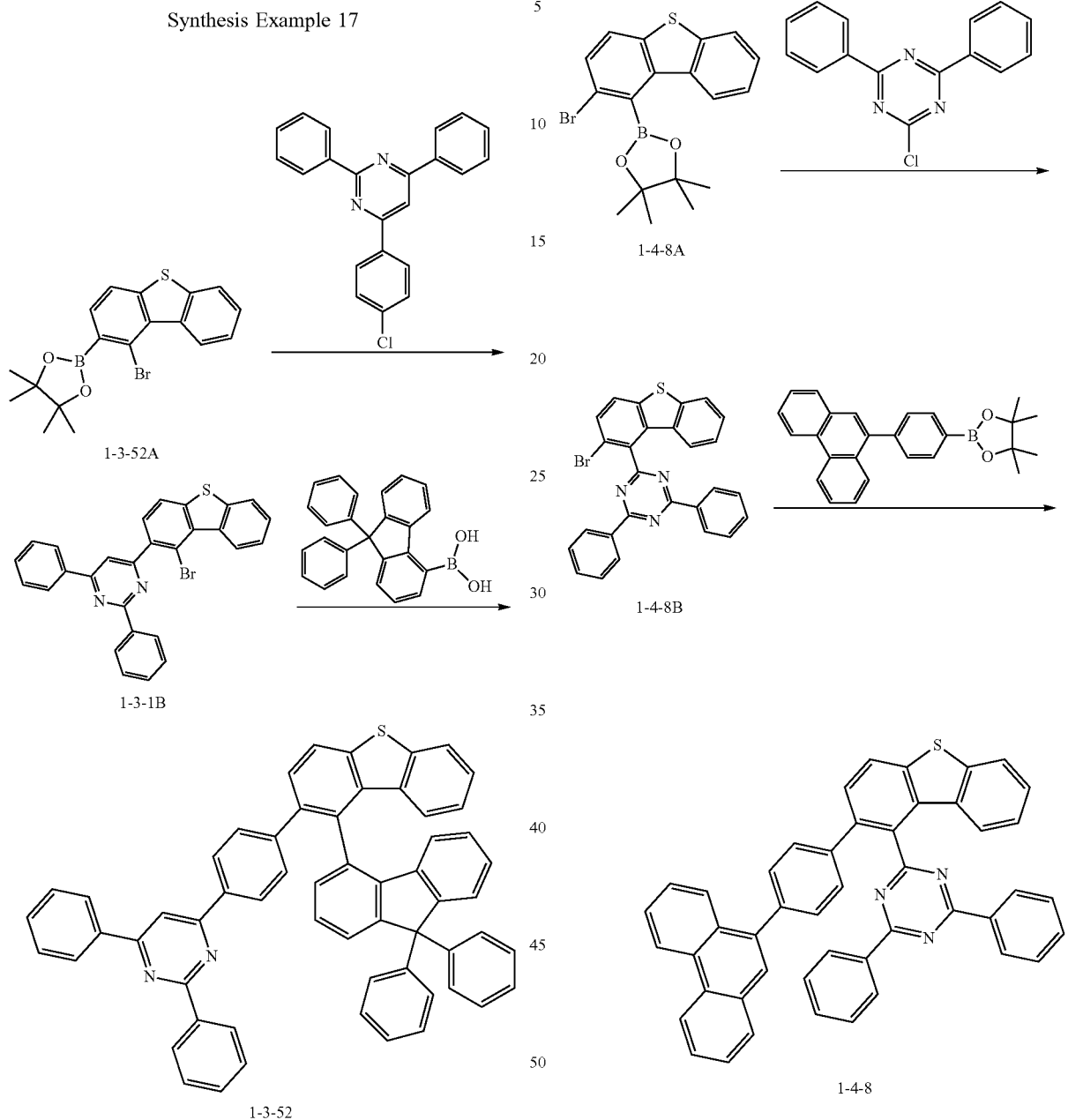

The compound 1-3-52B was prepared in the same manner as in the preparation of the compound 1-3-1B according to Synthesis Example 14, except that the compound 1-3-52A was used instead of the compound 1-3-1A and 4-(4-chlorophenyl)-2,6-diphenylpyrimidine was used instead of 2-chloro-4,6-diphenyl-1,3,5-triazine (MS: [M+H]⁺=493).

The compound 1-3-52 was prepared in the same manner as in the preparation of the compound 1-3-1 according to Synthesis Example 14, except that the compound 1-3-52B was used instead of the compound 1-3-1B and (9,9-diphenyl-9H-fluoren-4-yl)boronic acid was used instead of [1,1'-biphenyl]-4-ylboronic acid (MS: [M+H]⁺=807).

The compound 1-4-8B was prepared in the same manner as in the preparation of the compound 1-3-1B according to Synthesis Example 14, except that the compound 1-4-8A was used instead of the compound 1-3-1A (MS: [M+H]⁺=494).

The compound 1-4-8 was prepared in the same manner as in the preparation of the compound 1-3-1 according to Synthesis Example 14, except that the compound 1-4-8B was used instead of the compound 1-3-1B and 4,4,5,5-tetramethyl-2-(4-(phenanthren-9-yl)phenyl)-1,3,2-dioxaborolane was used instead of [1,1'-biphenyl]-4-ylboronic acid (MS: [M+H]⁺=668).

Synthesis Example 19

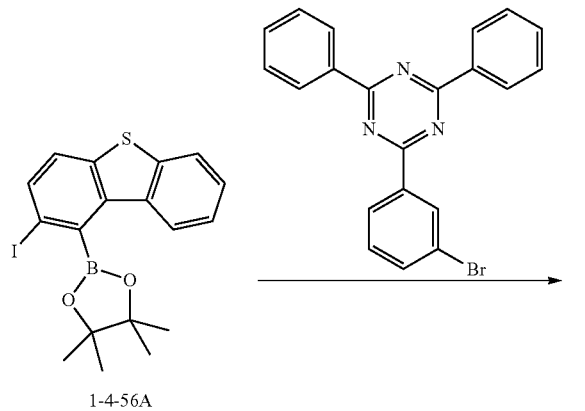

1-4-56

The compound 1-4-56B was prepared in the same manner as in the preparation of the compound 1-4-8B according to Synthesis Example 18, except that the compound 1-4-56A was used instead of the compound 1-4-8A and 2-(3-bromophenyl)-4,6-diphenyl-1,3,5-triazine was used instead of 2-chloro-4,6-diphenyl-1,3,5-triazine (MS: [M+H]+=542).

The compound 1-4-56 was prepared in the same manner as in the preparation of the compound 1-4-8 according to Synthesis Example 18, except that the compound 1-4-56B was used instead of the compound 1-4-8B and 4,4,5,5-tetramethyl-2-(triphenylene-1-yl)-1,3,2-dioxaborolane was used instead of 4,4,5,5-tetramethyl-2-(4-(phenanthren-9-yl)phenyl)-1,3,2-dioxaborolane (MS: [M+H]+=718).

Synthesis Example 20

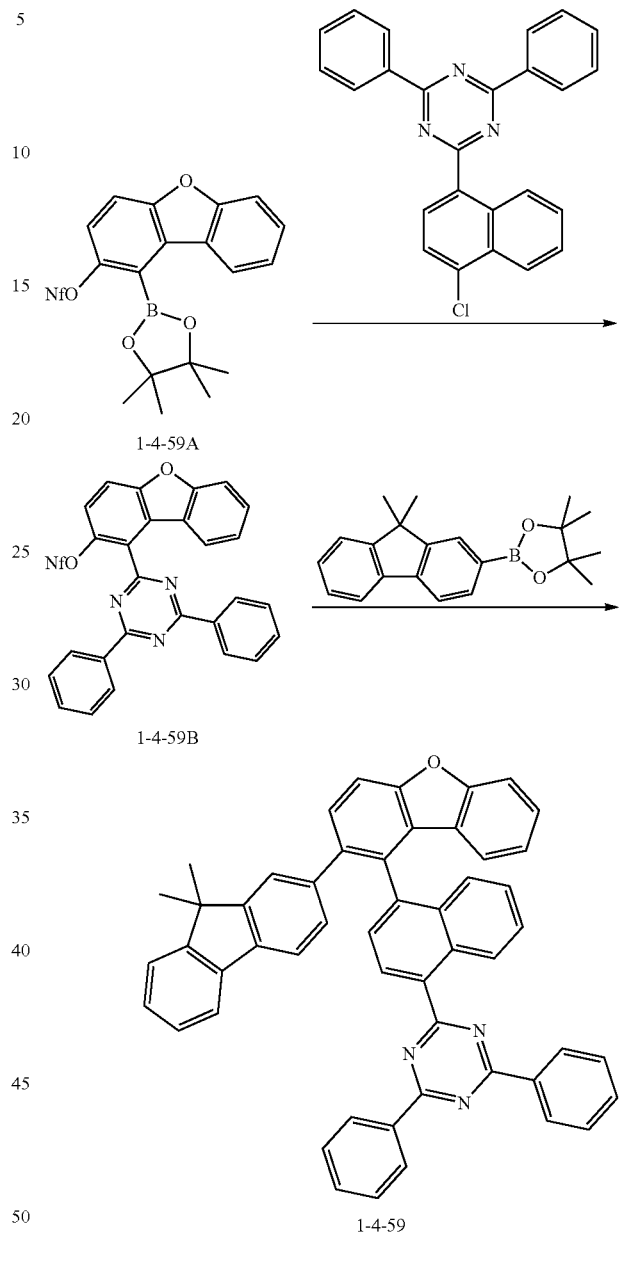

The compound 1-4-59B was prepared in the same manner as in the preparation of the compound 1-4-8B according to Synthesis Example 18, except that the compound 1-4-59A was used instead of the compound 1-4-8A and 2-(4-chloronaphthalen-1-yl)-4,6-diphenyl-1,3,5-triazine was used instead of 2-chloro-4,6-diphenyl-1,3,5-triazine (MS: [M+H]+=542).

The compound 1-4-59 was prepared in the same manner as in the preparation of the compound 1-4-8 according to Synthesis Example 18, except that the compound 1-4-59B was used instead of the compound 1-4-8B and 2-(9,9-dimethyl-9H-fluoren-2-yl)-4,4,5,5-tetramethyl-1,3,2-dioxaborolane was used instead of 4,4,5,5-tetramethyl-2-(4-(phenanthren-9-yl)phenyl)-1,3,2-dioxaborolane (MS: [M+H]+=718).

Synthesis Example 21

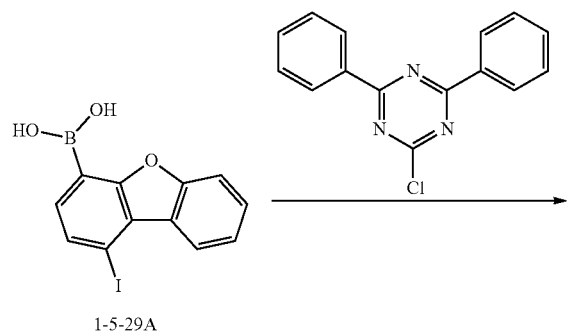

1-5-29A

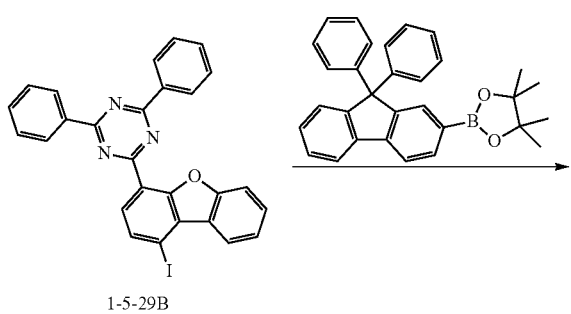

1-5-29B

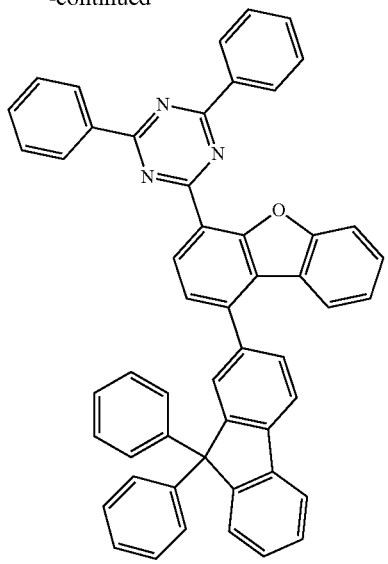

1-5-29

The compound 1-5-29B was prepared in the same manner as in the preparation of the compound 1-4-8B according to Synthesis Example 18, except that the compound 1-5-29A was used instead of the compound 1-4-8A (MS: [M+H]$^+$= 526).

The compound 1-5-29 was prepared in the same manner as in the preparation of the compound 1-4-8 according to Synthesis Example 18, except that the compound 1-5-29B was used instead of the compound 1-4-8B and 2-(9,9-diphenyl-9H-fluoren-2-yl)-4,4,5,5-tetramethyl-1,3,2-dioxaborolane was used instead of 4,4,5,5-tetramethyl-2-(4-(phenanthren-9-yl)phenyl)-1,3,2-dioxaborolane (MS: [M+H]$^+$=716).

Synthesis Example 22

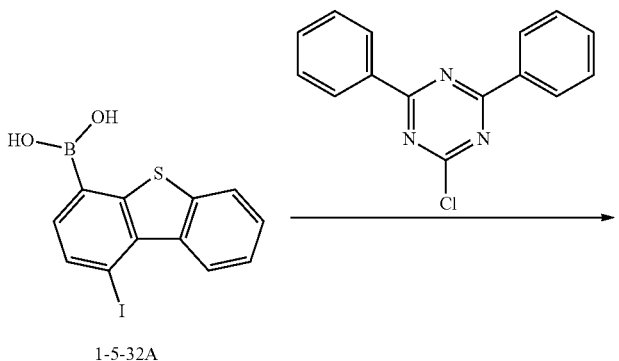

1-5-32A

-continued

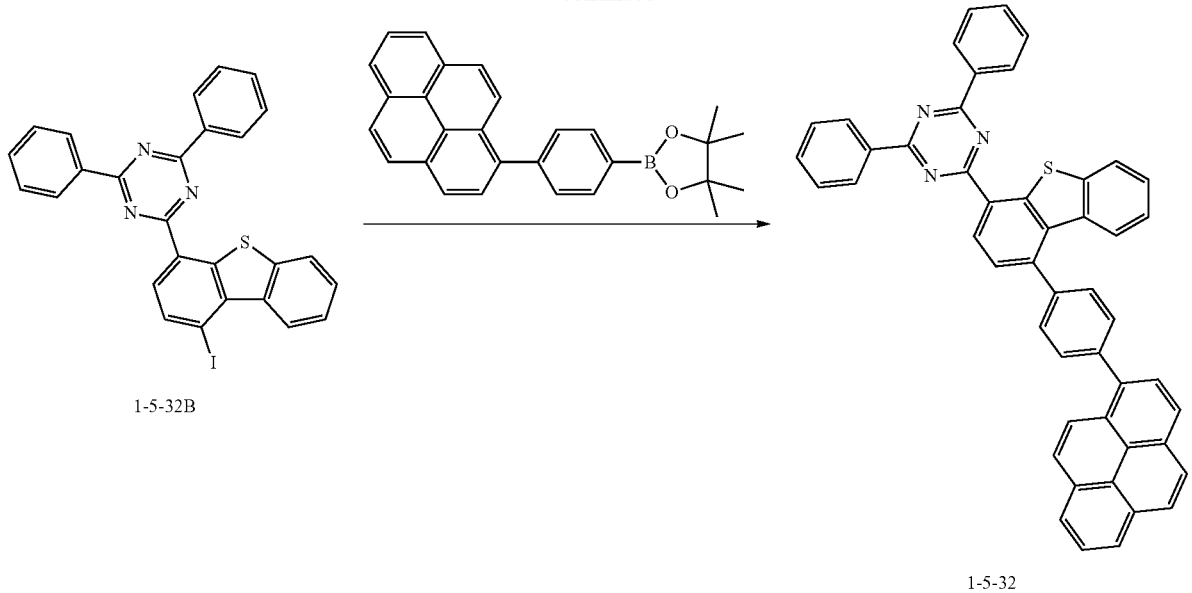

1-5-32B 1-5-32

The compound 1-5-32B was prepared in the same manner as in the preparation of the compound 1-5-29B according to Synthesis Example 21, except that the compound 1-5-32A was used instead of the compound 1-5-29A (MS: [M+H]$^+$=542).

The compound 1-5-32 was prepared in the same manner as in the preparation of the compound 1-5-29 according to Synthesis Example 21, except that the compound 1-5-32B was used instead of the compound 1-5-29B and 4,4,5,5-tetramethyl-2-(4-(pyrene-1-yl)phenyl)-1,3,2-dioxaborolane was used instead of 2-(9,9-diphenyl-9H-fluoren-2-yl)-4,4,5,5-tetramethyl-1,3,2-dioxaborolane (MS: [M+H]$^+$=692).

Synthesis Example 23

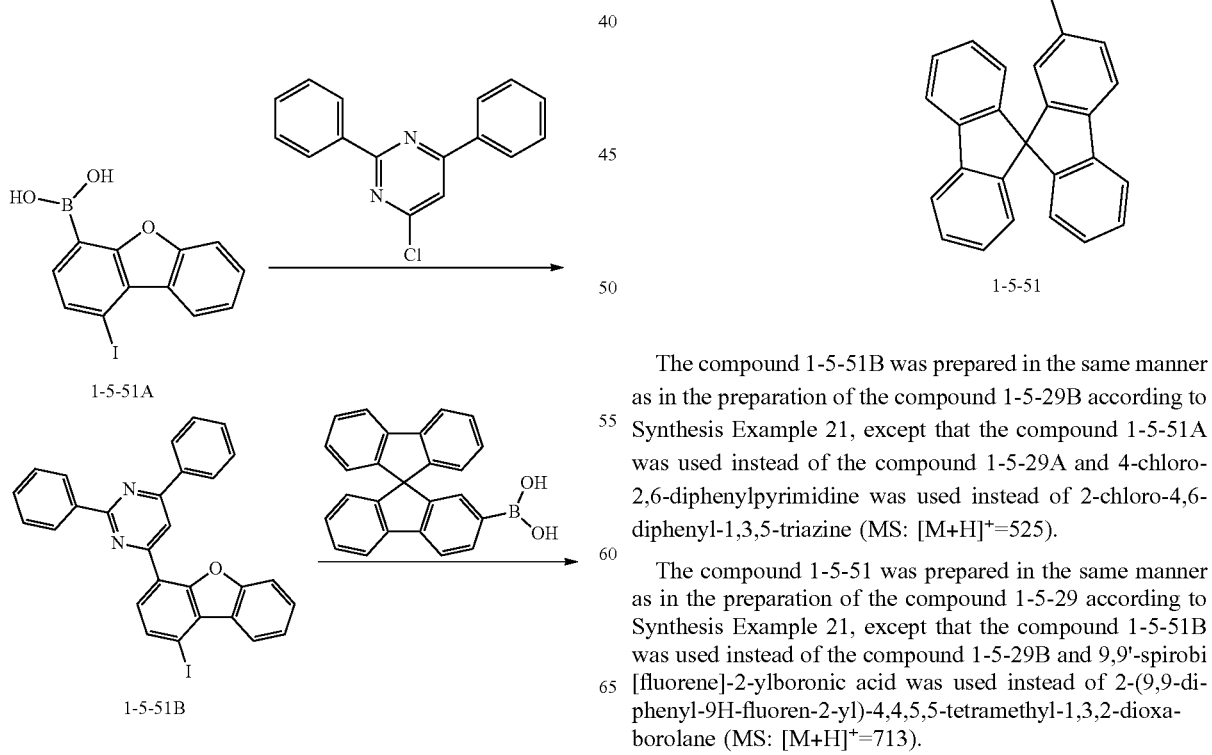

1-5-51A 1-5-51B 1-5-51

The compound 1-5-51B was prepared in the same manner as in the preparation of the compound 1-5-29B according to Synthesis Example 21, except that the compound 1-5-51A was used instead of the compound 1-5-29A and 4-chloro-2,6-diphenylpyrimidine was used instead of 2-chloro-4,6-diphenyl-1,3,5-triazine (MS: [M+H]$^+$=525).

The compound 1-5-51 was prepared in the same manner as in the preparation of the compound 1-5-29 according to Synthesis Example 21, except that the compound 1-5-51B was used instead of the compound 1-5-29B and 9,9'-spirobi[fluorene]-2-ylboronic acid was used instead of 2-(9,9-diphenyl-9H-fluoren-2-yl)-4,4,5,5-tetramethyl-1,3,2-dioxaborolane (MS: [M+H]$^+$=713).

Synthesis Example 24

Synthesis Example 25

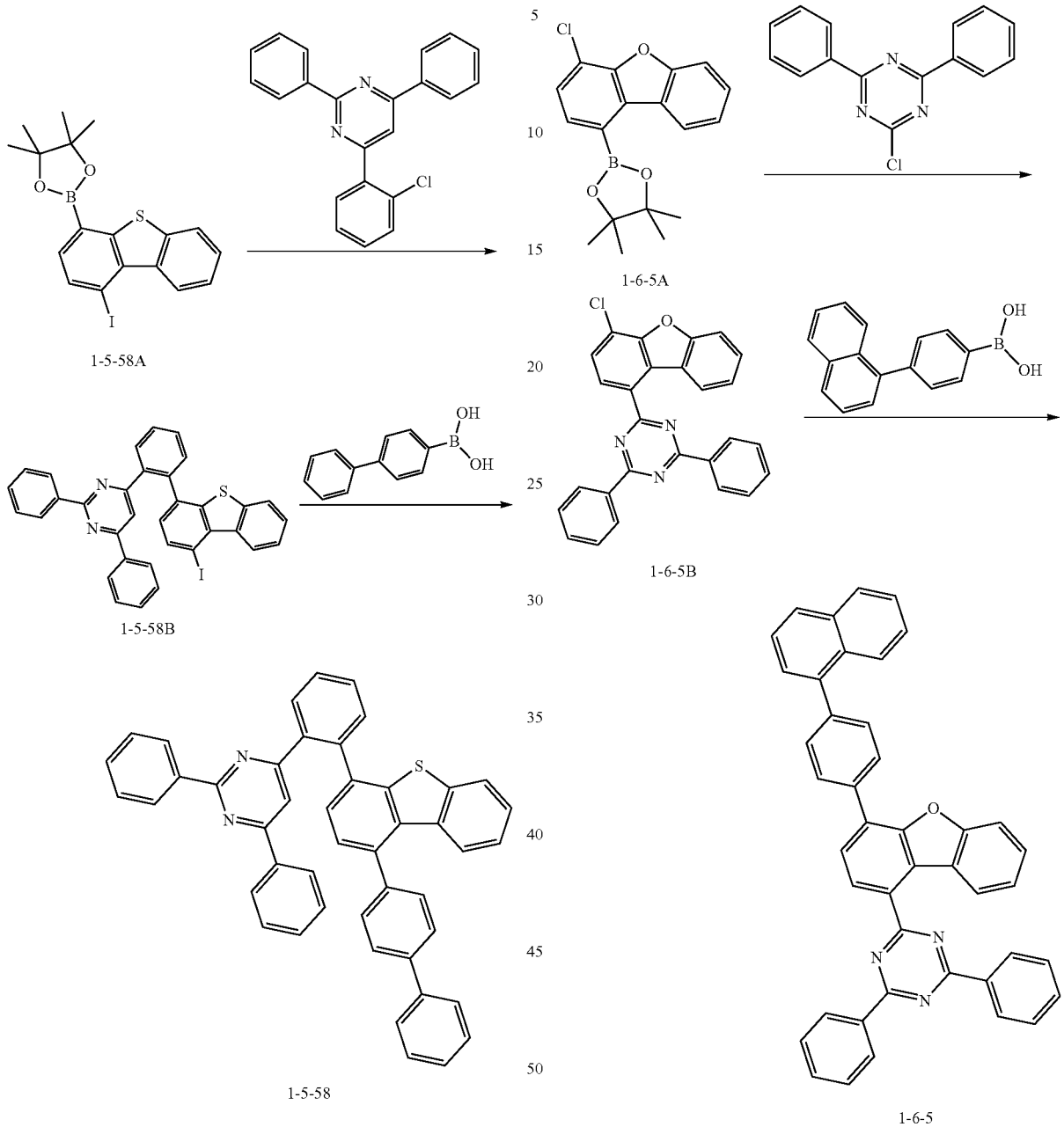

The compound 1-5-58B was prepared in the same manner as in the preparation of the compound 1-5-29B according to Synthesis Example 21, except that the compound 1-5-58A was used instead of the compound 1-5-29A and 4-(2-chlorophenyl)-2,6-diphenylpyrimidine was used instead of 2-chloro-4,6-diphenyl-1,3,5-triazine (MS: [M+H]$^+$=617).

The compound 1-5-58 was prepared in the same manner as in the preparation of the compound 1-5-29 according to Synthesis Example 21, except that the compound 1-5-58B was used instead of the compound 1-5-29B and [1,1'-biphenyl]-4-ylboronic acid was used instead of 2-(9,9-diphenyl-9H-fluoren-2-yl)-4,4,5,5-tetramethyl-1,3,2-dioxaborolane (MS: [M+H]$^+$=643).

The compound 1-5-5B was prepared in the same manner as in the preparation of the compound 1-5-29B according to Synthesis Example 21, except that the compound 1-6-5A was used instead of the compound 1-5-29A (MS: [M+H]$^+$=434).

The compound 1-6-5 was prepared in the same manner as in the preparation of the compound 1-5-29 according to Synthesis Example 21, except that the compound 1-6-5B was used instead of the compound 1-5-29B and (4-(naphthalen-1-yl)phenyl)boronic acid was used instead of 2-(9,9-diphenyl-9H-fluoren-2-yl)-4,4,5,5-tetramethyl-1,3,2-dioxaborolane (MS: [M+H]$^+$=602).

Synthesis Example 26

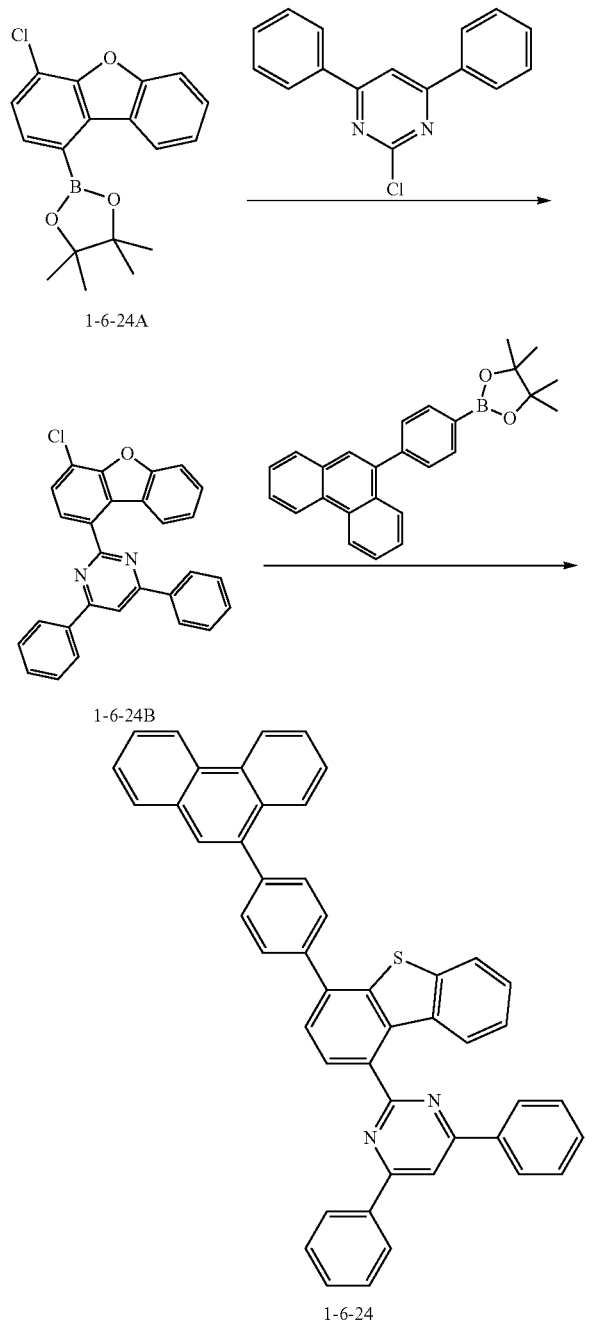

The compound 1-6-24B was prepared in the same manner as in the preparation of the compound 1-6-5B according to Synthesis Example 25, except that the compound 1-6-24A was used instead of the compound 1-6-5A and 2-chloro-4,6-diphenylpyrimidine was used instead of 2-chloro-4,6-diphenyl-1,3,5-triazine (MS: [M+H]$^+$=433).

The compound 1-6-24 was prepared in the same manner as in the preparation of the compound 1-6-5 according to Synthesis Example 25, except that the compound 1-6-24B was used instead of the compound 1-6-5B and 4,4,5,5-tetramethyl-2-(4-(phenanthren-9-yl)phenyl)-1,3,2-dioxaborolane was used instead of (4-(naphthalen-1-yl)phenyl)boronic acid (MS: [M+H]$^+$=667).

Synthesis Example 27

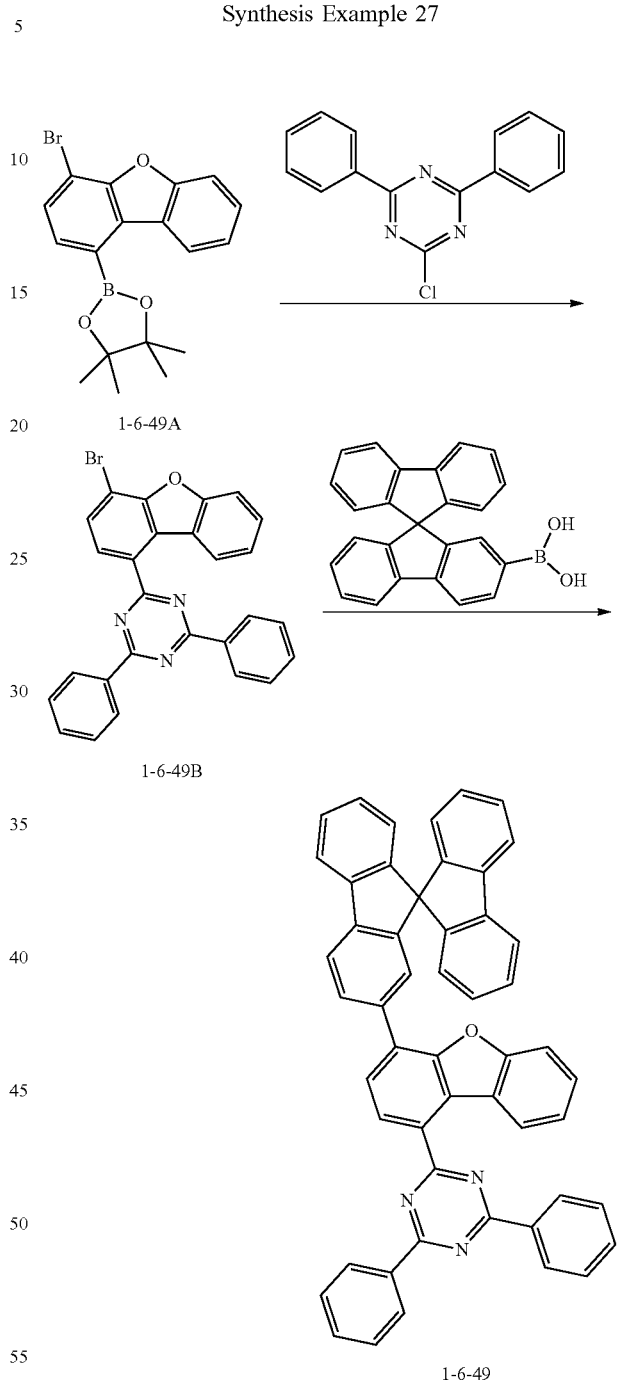

The compound 1-6-49B was prepared in the same manner as in the preparation of the compound 1-6-5B according to Synthesis Example 25, except that the compound 1-6-49A was used instead of the compound 1-6-5A (MS: [M+H]$^+$= 478).

The compound 1-6-49 was prepared in the same manner as in the preparation of the compound 1-6-5 according to Synthesis Example 25, except that the compound 1-6-49B was used instead of the compound 1-6-5B and 9,9'-spirobi

[fluorene]-2-ylboronic acid was used instead of (4-(naphthalen-1-yl)phenyl)boronic acid (MS: [M+H]$^+$=714).

Synthesis Example 28

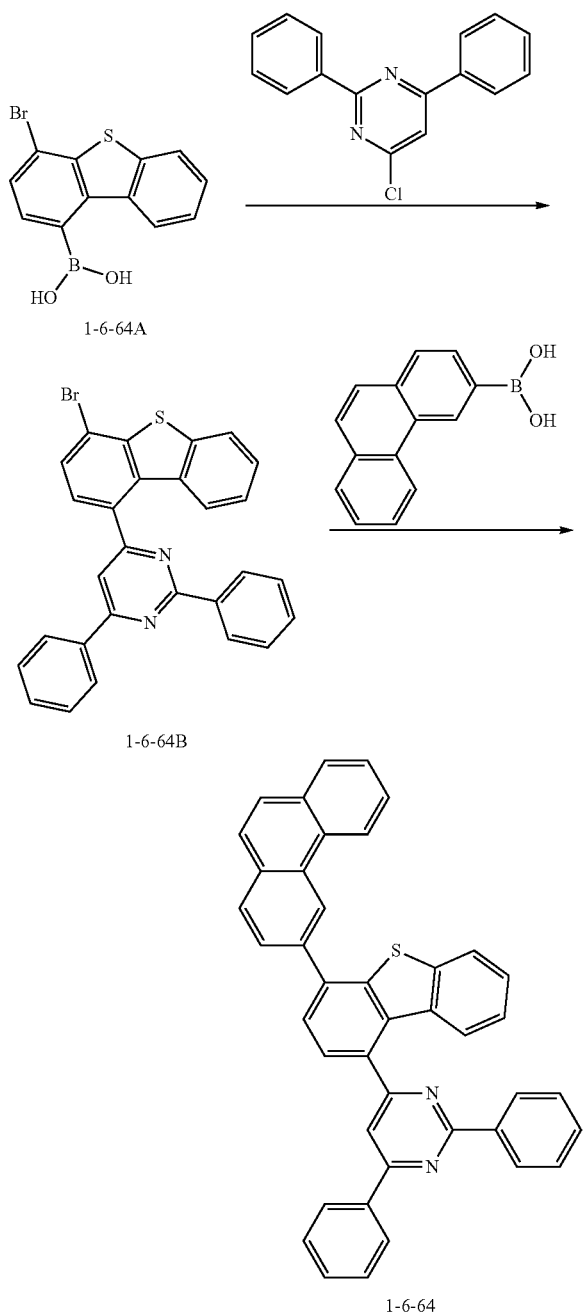

1-6-64A 1-6-64B 1-6-64

The compound 1-6-64B was prepared in the same manner as in the preparation of the compound 1-6-5B according to Synthesis Example 25, except that the compound 1-6-64A was used instead of the compound 1-6-5A and 4-chloro-2,6-diphenylpyrimidine was used instead of 2-chloro-4,6-diphenyl-1,3,5-triazine (MS: [M+H]$^+$=493).

The compound 1-6-64 was prepared in the same manner as in the preparation of the compound 1-6-5 according to Synthesis Example 25, except that the compound 1-6-64B was used instead of the compound 1-6-5B and phenanthren-3-ylboronic acid was used instead of (4-(naphthalen-1-yl)phenyl)boronic acid (MS: [M+H]$^+$=591).

Example 1

A glass substrate on which ITO (indium tin oxide) was coated as a thin film to a thickness of 1000 Å was put into distilled water in which a detergent was dissolved, and ultrasonically cleaned. In this case, a product manufactured by Fischer Co., was used as the detergent, and as the distilled water, distilled water filtered twice using a filter manufactured by Millipore Co., was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. The substrate was cleaned for 5 minutes using oxygen plasma, and then transferred to a vacuum depositor.

On the transparent ITO electrode prepared as above, the following compound [HI-A] was thermally vacuum-deposited to a thickness of 600 Å to form a hole injection layer. Hexaazatriphenylene (HAT) of the following chemical formula (50 Å) and the following compound [HT-A] (600 Å) were sequentially vacuum-deposited on the hole injection layer to form a hole transfer layer.

Subsequently, the following compounds [BH] and [BD] were vacuum-deposited in a weight ratio of 25:1 on the hole transfer layer to a film thickness of 200 Å to form a light emitting layer. The compound 1-1-1 and the following lithium quinolate [LiQ] compound were vacuum-deposited in a weight ratio of 1:1 on the light emitting layer to form an electron injection and transfer layer with a thickness of 350 Å. A cathode was formed on the electron injection and transfer layer by sequentially depositing lithium fluoride (LiF) to a thickness of 10 Å and aluminum to a thickness of 1000 Å.

In the above-mentioned process, the vapor deposition rate of the organic material was maintained at 0.4 to 0.9 Å/s, the vapor deposition rate of lithium fluoride of the cathode was maintained at 0.3 Å/s, the vapor deposition rate of aluminum was maintained at 2 Å/s, and the degree of vacuum during vapor deposition was maintained at $2 \times 10^{-7} \sim 5 \times 10^{-8}$ torr, thereby manufacturing an organic light emitting device.

HAT

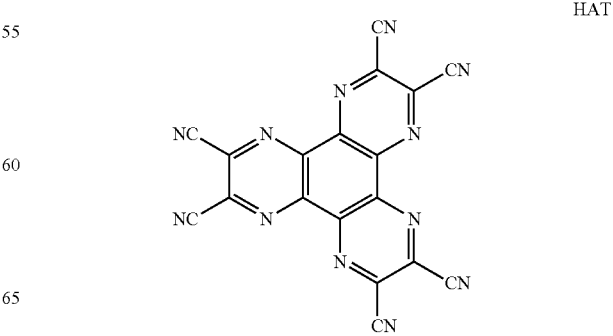

-continued

HI-A

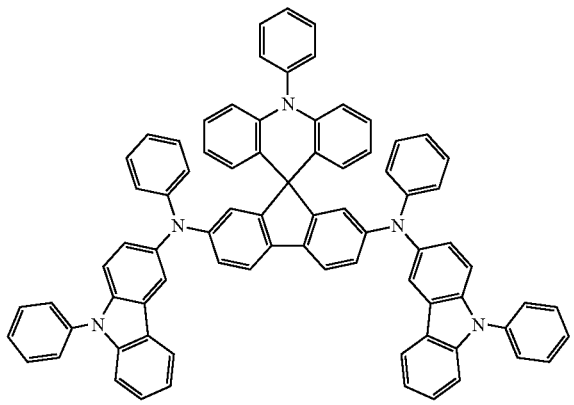

HT-A

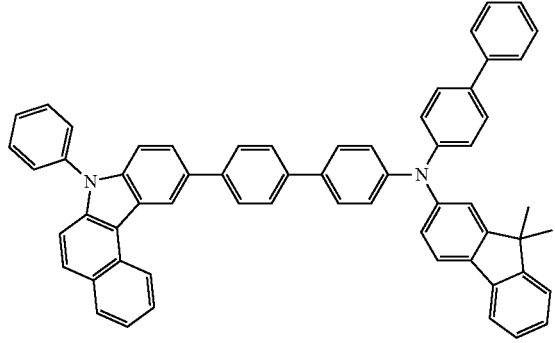

BH

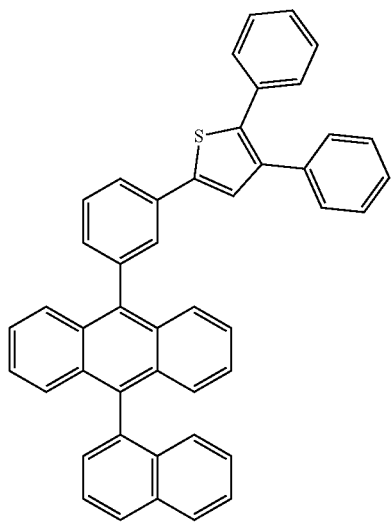

-continued

BD

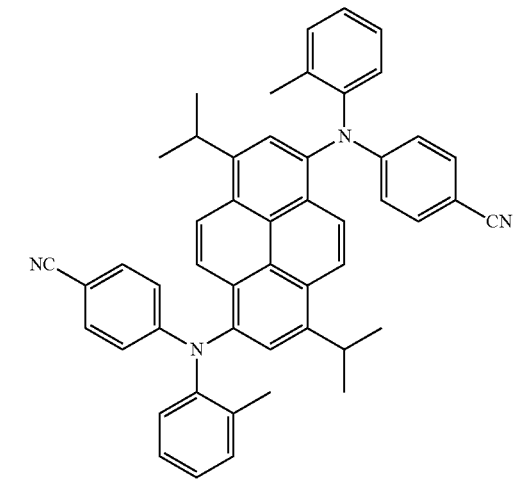

LiQ

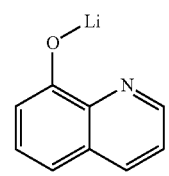

Examples 2 to 28

An organic light emitting device was manufactured in the same manner as in Example 1, except that the compounds described in the following Table 1 were used instead of the compound 1-1-1 of the electron transport layer in Example 1.

Comparative Example 1

An organic light emitting device was manufactured in the same manner as in Example 1, except that the following compound ET1 was used instead of the compound 1-1-1 of the electron transport layer in Example 1.

[ET1]

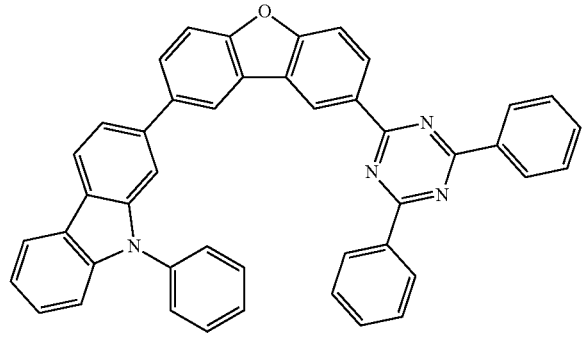

Comparative Example 2

An organic light emitting device was manufactured in the same manner as in Example 1, except that the following compound ET2 was used instead of the compound 1-1-1 of the electron transport layer in Example 1.

[ET2]

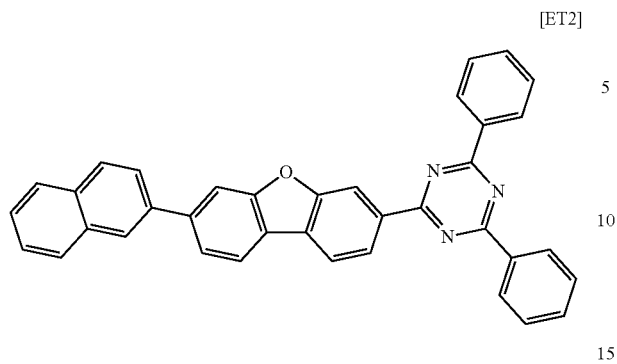

Comparative Example 3

An organic light emitting device was manufactured in the same manner as in Example 1, except that the following compound ET3 was used instead of the compound 1-1-1 of the electron transport layer in Example 1.

[ET4]

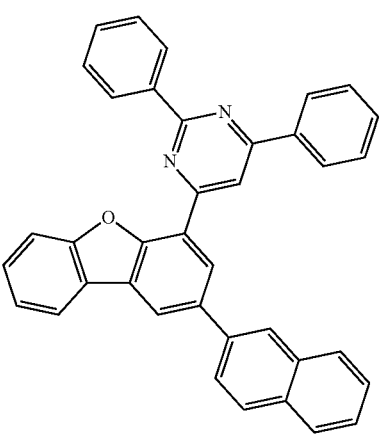

Comparative Example 5

An organic light emitting device was manufactured in the same manner as in Example 1, except that the following compound ET5 was used instead of the compound 1-1-1 of the electron transport layer in Example 1.

[ET3]

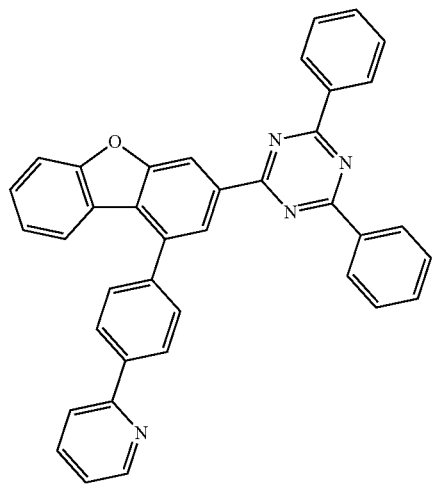

[ET5]

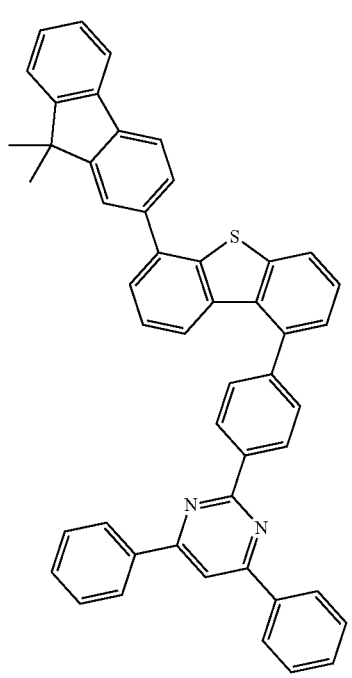

Comparative Example 4

An organic light emitting device was manufactured in the same manner as in Example 1, except that the following compound ET4 was used instead of the compound 1-1-1 of the electron transport layer in Example 1.

Comparative Example 6

An organic light emitting device was manufactured in the same manner as in Example 1, except that the following compound ET6 was used instead of the compound 1-1-1 of the electron transport layer in Example 1.

[ET6]

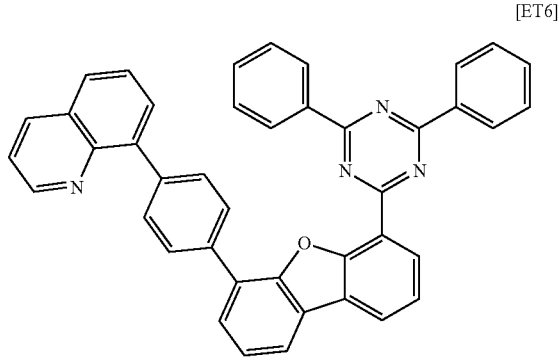 [SMILES: c1ccc(-c2nc(-c3ccccc3)nc(-c3cccc4c3oc3c(-c5ccc(-c6cccc7cccnc67)cc5)cccc34)n2)cc1]

Test Example

For the organic light emitting devices of Examples 1 to 28 and Comparative Examples 1 to 6 described above, a driving voltage and light emission efficiency were measured at a current density of 10 mA/cm$^2$, and time taken for the luminance to decrease to 90% compared to its initial value (LT90) was measured at a current density of 20 mA/cm$^2$. The results are shown in Table 1 below.

TABLE 1

| Compound | | Voltage (V @ 10 mA/cm$^2$) | Efficiency (cd/A @ 10 mA/cm$^2$) | Color coordinates (x, y) | LT90 (h, @ 20 mA/cm$^2$) |
|---|---|---|---|---|---|
| Example 1 | 1-1-1 | 3.68 | 5.29 | (0.142, 0.096) | 107 |
| Example 2 | 1-1-2 | 3.78 | 5.30 | (0.142, 0.097) | 103 |
| Example 3 | 1-1-3 | 3.73 | 5.35 | (0.142, 0.096) | 136 |
| Example 4 | 1-1-14 | 3.72 | 5.23 | (0.142, 0.097) | 115 |
| Example 5 | 1-1-23 | 3.70 | 5.26 | (0.142, 0.096) | 130 |
| Example 6 | 1-1-25 | 3.65 | 5.21 | (0.142, 0.097) | 121 |
| Example 7 | 1-1-30 | 3.82 | 5.12 | (0.142, 0.096) | 137 |
| Example 8 | 1-1-31 | 3.75 | 5.35 | (0.142, 0.096) | 108 |
| Example 9 | 1-1-52 | 3.83 | 5.12 | (0.142, 0.096) | 103 |
| Example 10 | 1-2-5 | 3.68 | 5.28 | (0.142, 0.096) | 109 |
| Example 11 | 1-2-27 | 3.63 | 5.31 | (0.142, 0.095) | 120 |
| Example 12 | 1-2-55 | 3.67 | 5.44 | (0.142, 0.096) | 134 |
| Example 13 | 1-2-63 | 3.76 | 5.15 | (0.142, 0.096) | 115 |
| Example 14 | 1-3-1 | 3.66 | 5.22 | (0.142, 0.097) | 117 |
| Example 15 | 1-3-6 | 3.76 | 5.25 | (0.142, 0.096) | 132 |
| Example 16 | 1-3-25 | 3.71 | 5.37 | (0.142, 0.096) | 121 |
| Example 17 | 1-3-52 | 3.86 | 5.11 | (0.142, 0.096) | 140 |
| Example 18 | 1-4-8 | 3.75 | 5.19 | (0.142, 0.097) | 127 |
| Example 19 | 1-4-56 | 3.79 | 5.22 | (0.142, 0.096) | 155 |
| Example 20 | 1-4-59 | 3.89 | 5.17 | (0.142, 0.096) | 122 |
| Example 21 | 1-5-29 | 3.73 | 5.48 | (0.142, 0.096) | 137 |
| Example 22 | 1-5-32 | 3.80 | 5.21 | (0.142, 0.096) | 114 |
| Example 23 | 1-5-51 | 3.72 | 5.28 | (0.142, 0.096) | 103 |
| Example 24 | 1-5-58 | 3.79 | 5.14 | (0.142, 0.096) | 119 |
| Example 25 | 1-6-5 | 3.65 | 5.21 | (0.142, 0.097) | 125 |
| Example 26 | 1-6-24 | 3.88 | 5.27 | (0.142, 0.097) | 122 |
| Example 27 | 1-6-49 | 3.76 | 5.33 | (0.142, 0.096) | 139 |
| Example 28 | 1-6-64 | 3.77 | 5.22 | (0.142, 0.096) | 118 |
| Comparative Example 1 | ET 1 | 4.82 | 4.21 | (0.142, 0.098) | 82 |
| Comparative Example 2 | ET 2 | 5.05 | 3.91 | (0.142, 0.096) | 90 |
| Comparative Example 3 | ET 3 | 4.98 | 4.18 | (0.142, 0.096) | 81 |
| Comparative Example 4 | ET 4 | 4.79 | 3.69 | (0.142, 0.096) | 83 |
| Comparative Example 5 | ET 5 | 5.09 | 3.68 | (0.142, 0.095) | 77 |
| Comparative Example 6 | ET 6 | 5.12 | 3.71 | (0.142, 0.096) | 79 |

Referring to Table 1 above, in the case of the organic light emitting devices manufactured by applying the compounds of the synthesis examples to the electron transport layer, they exhibited excellent characteristics in terms of efficiency, driving voltage, and/or stability in the organic light emitting device. In particular, the organic light emitting devices manufactured by applying the compounds of the synthesis examples to the electron transport layer exhibited lower voltage and higher efficiency characteristics than the organic light emitting devices of the comparative examples.

EXPLANATION OF SIGNS

1: substrate
2: anode
3: light emitting layer
4: cathode
5: hole injection layer
6: hole transport layer
7: light emitting layer
8: electron transport layer

The invention claimed is:
1. An organic electroluminescent device, comprising:
a first electrode;
a second electrode provided opposite to the first electrode; and
two or more organic material layers provided between the first electrode and the second electrode,
wherein:
one of the two or more organic material layers comprises a light emitting layer comprising a host material and a dopant material, the dopant material comprising a substituted or unsubstituted fused aromatic ring derivative including a pyrene, an anthracene, a chrysene, or a periflanthene, and comprising an arylamino group; and
one of the two or more organic material layers comprises an electron transport layer in contact with the light emitting layer, and the electron transport layer com- prises, in a weight ratio of 1:1, lithium quinolate and a compound of Chemical Formula 1-3:

[Chemical Formula 1-3]

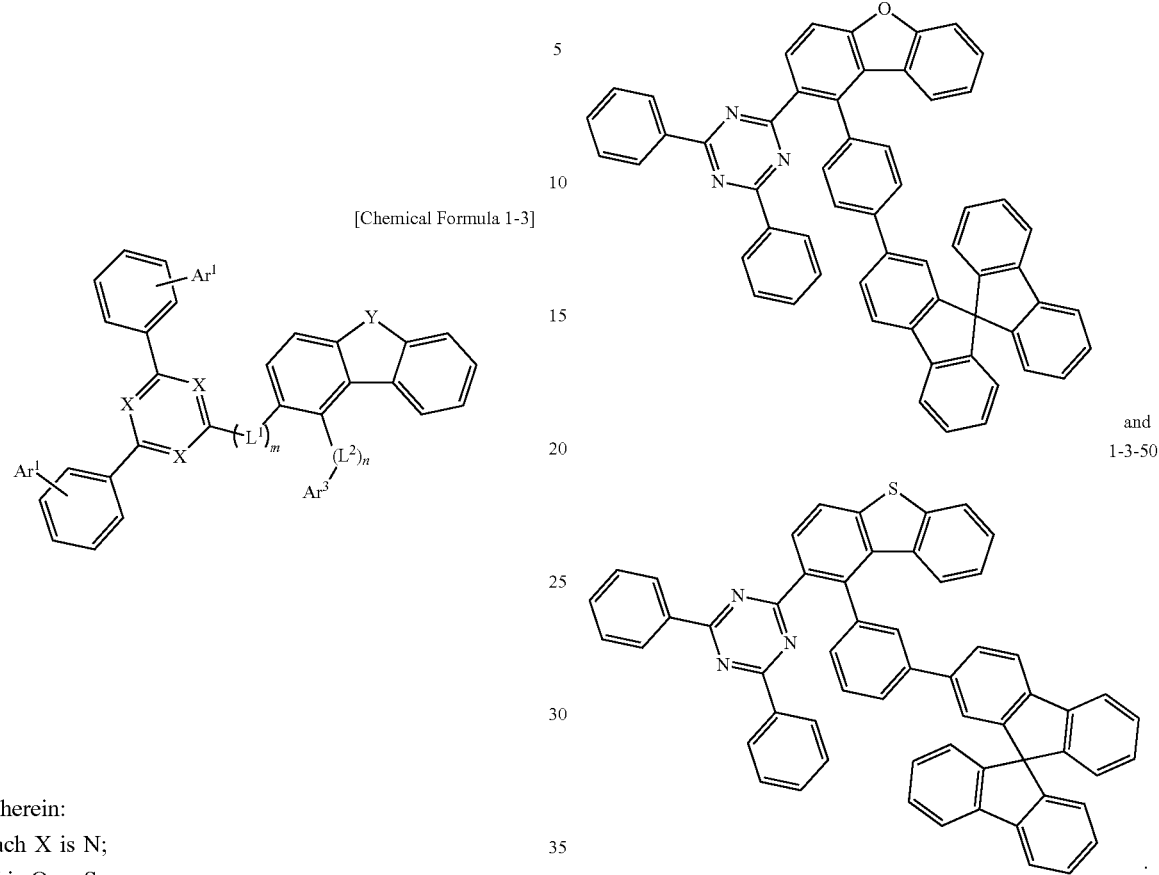

wherein:

each X is N;

Y is O or S;

$L^1$ is a direct bond, or a phenylene group which is unsubstituted or substituted by deuterium;

$L^2$ is a phenylene group which is unsubstituted or substituted by deuterium;

m and n are each independently an integer of 0 to 2, provided that when m=2, $L^1$ is not a direct bond;

$Ar^1$ and $Ar^2$ are each independently hydrogen or deuterium; and $Ar^3$ is

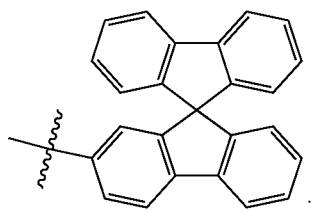 [SMILES: *c1ccc2c(c1)C1(c3ccccc3-c3ccccc31)c1ccccc1-2]

2. The organic electroluminescent device of claim 1, wherein m and n are each independently 0 or 1.

3. The organic electroluminescent device of claim 1, wherein $Ar^1$ and $Ar^2$ are each hydrogen.

4. The organic electroluminescent device of claim 1, wherein the compound of Chemical Formula 1-3 is selected from the group consisting of the following compounds:

5. The organic electroluminescent device of claim 1, wherein the two or more organic material layers further comprises one or more layers selected from among a hole injection layer, a hole transport layer, and an electron injection layer.

6. The organic electroluminescent device of claim 1, wherein the light emitting layer comprises the following compounds:

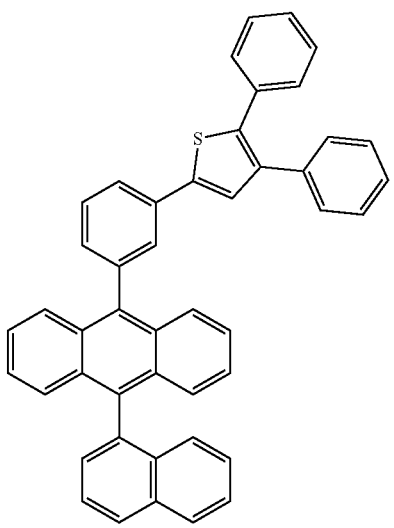

-continued
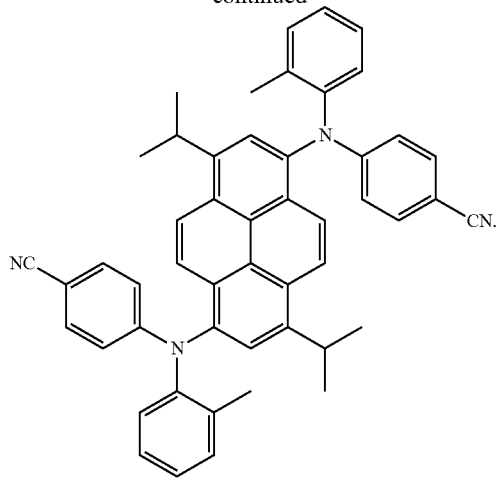
* * * * *